(12) United States Patent
Hasegawa et al.

(10) Patent No.: US 7,820,715 B2
(45) Date of Patent: Oct. 26, 2010

(54) CRYSTAL COMPRISING (2R)-2-PROPYLOCTANOIC ACID AND AMINE

(75) Inventors: Tomoyuki Hasegawa, Sakai (JP); Yasufumi Kawanaka, Sakai (JP); Eiji Kasamatsu, Sakai (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 1000 days.

(21) Appl. No.: 11/579,071

(22) PCT Filed: Apr. 27, 2005

(86) PCT No.: PCT/JP2005/008462

§ 371 (c)(1), (2), (4) Date: Oct. 27, 2006

(87) PCT Pub. No.: WO2005/105722

PCT Pub. Date: Nov. 10, 2005

(65) Prior Publication Data

US 2008/0090907 A1 Apr. 17, 2008

(30) Foreign Application Priority Data

Apr. 28, 2004 (JP) .................... P. 2004-134655

(51) Int. Cl.
*A61K 31/205* (2006.01)
*C07C 229/00* (2006.01)
*C07B 57/00* (2006.01)

(52) U.S. Cl. .................... 514/554; 554/103; 562/401

(58) Field of Classification Search ................ None
See application file for complete search history.

(56) References Cited

FOREIGN PATENT DOCUMENTS

| JP | 08291106 A | * 11/1995 |
| JP | 8-291106 A | 11/1996 |
| WO | WO 00/48982 A1 | 8/2000 |
| WO | WO 03/051852 A1 | 6/2003 |

* cited by examiner

*Primary Examiner*—Paul A Zucker
(74) *Attorney, Agent, or Firm*—Sughrue Mion, PLLC

(57) ABSTRACT

Crystals comprising (2R)-2-propyloctoic acid and an amine which retain the pharmacological effect of (2R)-2-propyloctoic acid and can be safely used as a medicinal raw drug for peroral solid preparations. Of these crystals, the crystals especially with dibenzylamine are advantageous because not only the crystals themselves are useful as a medicinal raw drug but also use of the crystals as an intermediate can yield (2R)-2-propyloctoic acid having an optical purity exceeding 99.5% e.e., which has not been obtained hitherto.

7 Claims, 60 Drawing Sheets

2,2,6,6,-tetramethyl-4-piperidinol

CRYSTAL COMPRISING (2R)-2-PROPYLOCTANOIC ACID AND AMINE

TECHNICAL FIELD

The present invention relates to crystals comprising (2R)-2-propyloctanoic acid and amines useful as bulk drugs for pharmaceuticals.

BACKGROUND ART

Orally administrable pharmaceuticals are mainly prescribed as oral solid pharmaceutical preparations such as tablets, powders, capsules, and the like. Among these preparations, tablets have been most often used at home and abroad because they can easily be administered and handled.

On the other hand, (2R)-2-propyloctanoic acid has been known to be a useful compound in a variety of diseases including cerebral apoplexy since it acts to improve the function of astrocytes (EP Patent 0632008 and EP-A-1174131). However, it was hard to formulate (2R)-2-propyloctanoic acid into such a formulation as tablets and to administer it to patients, because it is oil.

In general, it is considered preferable that the bulk drugs for pharmaceuticals, particularly the materials used as the bulk drugs for pharmaceuticals for oral solid preparations, are those obtained as crystals since the crystals allow a stable supply in large quantities and relatively easy formulation into such a form as tablets.

Accordingly, the materials which are intended to use as oral solid preparations are tried to crystallize by performing such an operation as formation of salts, when they are amorphous or liquid materials in a free state.

The above Patent Documents describe that (2R)-2-propyloctanoic acid may be formed into salts including salts with alkali metals (potassium, sodium, etc.), salts with alkaline earth metals (e.g., calcium, magnesium, etc.), ammonium salt, salts with organic amines (e.g., tetramethylammonium, triethylamine, methylamine, dimethylamine, cyclopentylamine, benzylamine, phenethylamine, piperidine, monoethanolamine, diethanolamine, tris(hydroxymethyl)amine, lysine, arginine, N-methyl-D-glucan, etc.), and the like.

The sodium salt of (2R)-2-propyloctanoic acid, i.e., alkali metal salt, however, was obtained not as crystals but as waxy solid in practical preparation; this was difficult to handle and had no desired physicochemical properties adaptable as a bulk drug for pharmaceuticals directed to oral solid preparations.

On the other hand, it is known that as for (2R)-2-propyloctanoic acid amine salts, a salt of (2R)-2-propyloctanoic acid with (R)-(+)-1-phenylethylamine can be obtained as a salt, which is used as an intermediate in production of optically highly pure (2R)-2-propyloctanoic acid (see: WO03/051852). The salts with other amines, however, have not yet been synthesized practically up to date; therefore, it was unclear whether it can be obtained as crystals and is endurable in use as a bulk drug for pharmaceuticals in oral solid preparations.

DISCLOSURE OF INVENTION

The problem to be solved by the present invention, accordingly, is to provide a crystal comprising (2R)-2-propyloctanoic acid and an amine, which can be used safely, for example, as a bulk drug for oral solid pharmaceutical preparations with keeping the pharmacological activity of (2R)-2-propyloctanoic acid.

In general, whether a compound formed by an acid and a base can be crystallized or not, depends on the combination of an acid and base, and further on the solvent used in crystallization. In other words, successful crystallization does not depend on the property of an acid or base itself. Therefore, even if combination of a certain acid and a certain base gives crystals successfully, the acid does not necessarily give crystals in combination with any kind of base.

The present inventors tried assiduously to obtain crystals comprising (2R)-2-propyloctanoic acid and an amine using a variety of amines and a variety of solvents. As a result, they succeeded in obtaining some crystals from a large number of combinations, which crystals can be used as bulk drugs for oral solid pharmaceutical preparations. Thus, the present invention was completed.

In addition, the present inventors found that among the resulting crystals a crystal comprising (2R)-2-propyloctanoic acid and dibenzylamine is also useful as an intermediate to obtain very highly optically pure (2R)-2-propyloctanoic acid.

That is, the present invention relates to the followings:

1. An isolated crystal comprising (2R)-2-propyloctanoic acid and amine, excluding (R)-(+)-1-phenylethylamine;
2. The crystal according to the above 1, wherein the amine is (+)-dehydroabietylamine, (R)-(−)-2-phenylglycinol, (S)-(+)-2-phenylglycinol, (−)-cis-myrtanylamine, (R)-(+)-1-(p-tolyl)ethylamine, (R)-(+)-1-(1-naphthyl)ethylamine, (S)-(−)-1-(1-naphthyl)ethylamine, L-tyrosinamide, (1S,2R)-(+)-2-amino-1,2-diphenylethanol, (1R,2S)-(−)-2-amino-1,2-diphenylethanol, (+)-cis-2-benzylaminocyclohexanemethanol, (−)-cis-2-benzylaminocyclohexanemethanol, (S)-(−)-2-amino-3-phenyl-1-propanol, (R)-(+)-2-amino-3-phenyl-1-propanol, (R-(+)-1-(4-bromophenyl)ethylamine, (R)-(+)-1-phenylpropylamine, dibenzylamine, 1,2-diphenylethylamine, benzhydrylamine, cyclohexylamine, dicyclohexylamine, cycloheptylamine, N-ethylcyclohexylamine, 2,2,6,6-tetramethyl-4-piperidinol, 2-(2-methoxyphenyl)ethylamine, 2-(3,4-dimethoxyphenyl)ethylamine, N-isopropylbenzylamine, or N-butylbenzylamine;
3. A pharmaceutical composition, comprising the crystal according to the above 2 as an active ingredient;
4. The pharmaceutical composition according to the above 3, which is an agent for prevention, treatment and/or suppression of symptom progression symptom progression for neurodegenerative diseases, nerupopathies or diseases in need of nerve regeneration;
5. A pharmaceutical composition, comprising the crystal according to the above 2 in combination with at least one selected from an anticonvulsant, an acetylcholinesterase inhibitor, a neurotrophic factor, an aldose reductase inhibitor, an antithrombotic, an oral anticoagulant, a synthetic antithrombin drug, an antiplatelet drug, a thrombolytic agent, a Factor Xa inhibitor, a Factor VIIa inhibitor, a cerebral blood flow and metabolism improver, an antioxidant, a glycerin preparation, a β-secretase inhibitor, a β-amyloid protein aggregation inhibitor, a cerebral function activator, a dopamine receptor agonist, a monoamine oxidase inhibitor, an anticholinergic drug, a COMT inhibitor, a therapeutic agent for amyotrophic lateral sclerosis, a therapeutic agent for hyperlipidemia, an apoptosis inhibitor, a nerve differentiation and regeneration promoter, a non-steroidal anti-inflammatory drug, a steroid drug, and a sexual hormone or its derivative;
6. A method for prevention, treatment and/or suppression of symptom progression symptom progression for neurodegenerative diseases, nerupopathies or diseases in need of nerve regeneration, which comprises administering to a mammal an effective amount of the crystal according to the above 2;

7. Use of the crystal according to the above 2 for the manufacture of an agent for prevention, treatment and/or suppression of symptom progression symptom progression for neurodegenerative diseases, nerurophathies or diseases in need of nerve regeneration;

8. An isolated crystal comprising 2-propyloctanoic acid and dibenzylamine;

9. The isolated crystal according to the above 2, wherein the 2-propyloctanoic acid is (2R)-2-propyloctanoic acid;

10. The isolated crystal according to the above 9, which has an optical purity of 97% e.e. or more;

11. The isolated crystal according to the above 9, which has a specific rotation of −3.6°;

12. A process for producing (2R)-2-propyloctanoic acid having an optical purity of 97% e.e. or more, which comprises:
dissolving (2R)-2-propyloctanoic acid having an optical purity of 70% e.e. or more and an optically inactive amine in a solvent to give a solution;
repeating the following steps (1)-(3) 0 to 3 times
(1) preferentially crystallizing a crystal comprising the (2R)-2-propyloctanoic acid with the optically inactive amine from the solution;
(2) separating and collecting the precipitated crystal;
(3) dissolving the crystal in a solvent to give a solution;
preferentially crystallizing a crystal comprising the (2R)-2-propyloctanoic acid with the optically inactive amine from the solution; and
separating and collecting the precipitated crystal to give a free (2R)-2-propyloctanoic acid;

13. The process according to the above 12, wherein the optically inactive amine is dibenzylamine;

14. (2R)-2-propyloctanoic acid having an optical purity of more than 99.5% e.e.;

15. The (2R)-2-propyloctanoic acid according to the above 14, which is obtainable by the process according to the above 13;

16. A pharmaceutical composition, comprising (2R)-2-propyloctanoic acid according to the above 14;

17. The pharmaceutical composition according to the above 16, which is an agent for prevention, treatment and/or suppression of symptom progression for neurodegenerative diseases, neuropathies or diseases in need of nerve regeneration;

18. The isolated crystal according to the above 9, which has a melting point of about 79.0 to about 80.2° C.;

19. The isolated crystal according to the above 9, which has diffraction angles (2θ) of 15.27, 17.03, 19.04, 19.99, 21.36, 22.91, 24.21, 26.09, 26.70, 28.42, 30.83, 34.06 in powdered X-ray diffraction spectrum;

20. The isolated crystal according to the above 9, wherein the powdered X-ray diffraction spectrum is powdered X-ray diffraction spectrum shown in FIG. 1;

21. The isolated crystal according to the above 9, which has absorptions at 3434, 3068, 3036, 2957, 2926, 2872, 2853, 2756, 2621, 2454, 1948, 1638, 1498, 1466, 1457, 1415, 1379, 1342, 1321, 1212, 1141, 1112, 1096, 1044, 989, 936, 905, 812, 763, 744, 694 cm$^{-1}$ in infrared absorption spectrum;

22. The isolated crystal according to the above 9, wherein the infrared absorption spectrum is infrared absorption spectrum shown in FIG. 2;

23. A production process of the crystal according to the above 1;

24. A method for improving the optical purity of (2R)-2-propyloctanoic acid, which comprises using dibenzylamine;
and the like.

DETAILED DESCRIPTION

Figure 1:
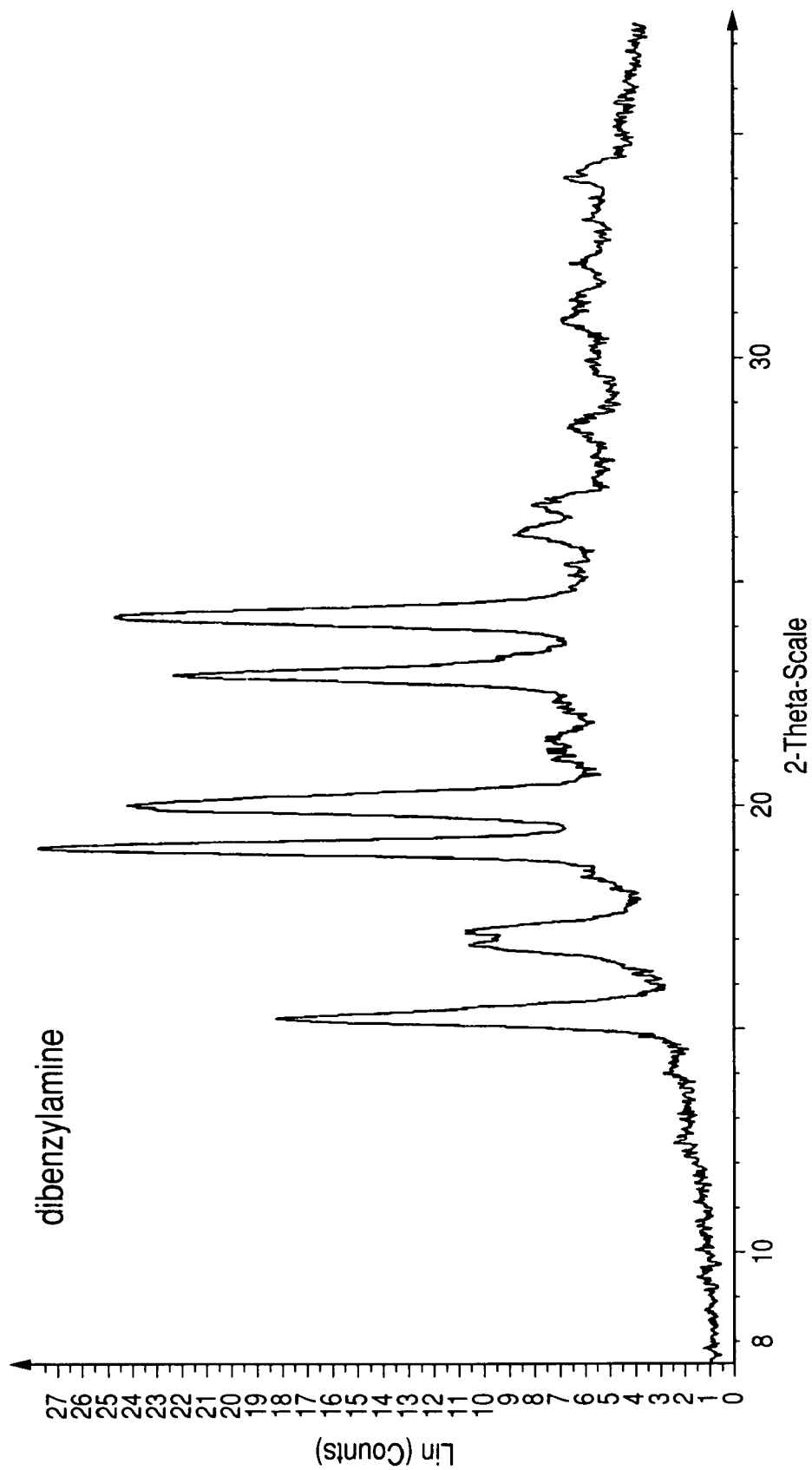
FIG. 1 shows a chart of powdered X-ray diffraction spectrum of a crystal comprising (2R)-2-propyloctanoic acid and dibenzylamine.

In the present invention, (2R)-2-propyloctanoic acid means a compound of formula (I):

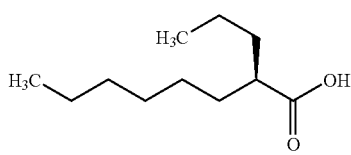

wherein ⫽ indicates a β-configuration.

In the present invention, (2R)-2-propyloctanoic acid is not limited to a practically pure single material but includes a mixture of (2R)-2-propyloctanoic acid and (2S)-2-propyloctanoic acid of formula (II):

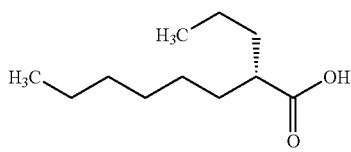

wherein ⋰ indicates an α-configuration, that is, as far as (2R)-2-propyloctanoic acid is preferentially contained, it is defined as (2R)-2-propyloctanoic acid. In addition, (2R)-2-propyloctanoic acid may contain, for example, impurities such as by-product, solvent, raw material, or degradation product.

The content of these impurities is variable depending on the kind of impurities contained and the subsequent intended use, and there is no limitation in the content, accordingly. When (2R)-2-propyloctanoic acid is used as a bulk drug for pharmaceuticals, the content is preferably, for example, about 20 ppm or lower for heavy metals, about 1.49% by mass or less for (2S)-2-propyloctanoic acid, about 5000 ppm or less in total for the residual solvent 2-propanol or heptane, and about 0.2% by mass or less for moisture.

(2R)-2-Propyloctanoic acid may be produced according to the per se known processes as described in, for example, JP Patent 3032447, JP Patent 3084345, EP Patent 0632008, EP Patent 1078921, U.S. Pat. No. 6,608,221, WO03/051852, WO03/097851, and WO04/110972; process as described in *Comprehensive Organic Transformations: A Guide to Functional Group Preparation,* 2nd Edition (Richard C. Larock, John Wiley & Sons Inc., 1999); for example, according to the process as described in Examples as mentioned below; or in proper combination of those processes. The resulting (2R)-2-propyloctanoic acid can be purified by a conventional purification method, for example, distillation under atmospheric pressure or reduced pressure, high performance liquid chromatography using silica gel or magnesium silicate, thin layer chromatography, or column chromatography or washing.

The present invention discloses such a crystal comprising (2R)-2-propyloctanoic acid and an amine. In this specification, the crystal means a solid material in which the constitutive molecules are arranged in three-dimensional periodism and which has approximately a definite melting point and definite constitution.

In this invention, the amine may be in any type including optically active amines and optically inactive amines, as far as it can form a crystal with (2R)-2-propyloctanoic acid. Herein, the optically active amine means those having an optical rotating power, and the optically inactive amine means those having no optical rotating power. This classification is not affected by the presence or absence of an asymmetric carbon. The racemates of amines are classified into an optically inactive amines in this invention.

As for the amines in the present invention, for example, the following amines are preferably used. All of those amines are known clearly as seen from the CAS number indicated in the parenthesis.

In the present invention, the optically active amine includes preferably, for example, (a-1) (+)-dehydroabietylamine [CAS: #1446-61-3], (a-2) (R)-(−)-2-phenylglycinol [CAS: #56613-80-0], (a-3) (S)-(+)-2-phenylglycinol [CAS: #20989-17-7], (a-4) (−)-cis-myrtanylamine [CAS: #38235-68-6], (a-5) (R)-(+)-1-(p-tolyl)ethylamine [CAS: #4187-38-6], (a-6) (R)-(+)-1-(1-naphthyl)ethylamine [CAS: #3886-70-2], (a-7) (S)-(−)-1-(1-naphthyl)ethylamine [CAS: #10420-89-0], (a-8) L-tyrosinamide [CAS. #4985-46-0], (a-9) (1S, 2R)-(+)-2-amino-1,2-diphenylethanol [CAS: #23364-44-5], (a-10) (1R,2S)-(−)-2-amino-1,2-diphenylethanol [CAS #23190-16-1], (a-11) (+)-cis-2-benzylaminocyclohexanemethanol [CAS: #71581-92-5], (a-12) (−)-cis-2-benzylaminocyclohexanemethanol [CAS: #71581-93-6], (a-13) (S)-(−)-2-amino-3-phenyl-1-propanol [CAS: #3182-95-6], (a-14) (R)-(+)-2-amino-3-phenyl-1-propanol [CAS: #5267-64-1], (a-15) (R)-(+)-1-(4-bromophenyl)ethylamine [CAS: #45791-36-4] and (a-16) (R)-(+)-1-phenylpropylamine [CAS: #3082-64-2].

In the present invention, the optically inactive amine includes preferably, for example, (b-1) dibenzylamine [CAS: #103-49-1], (b-2) 1,2-diphenylethylamine [CAS: #25611-78-3], (b-3) benzhydrylamine [CAS: #911-00-9], (b-4) cyclohexylamine [CAS: #108-91-8], (b-5) dicyclohexylamine [CAS: #101-83-7], (b-6) cycloheptylamine [CAS: #5452-35-7], (b-7) N-ethylcyclohexylamine [CAS: #5459-93-8], (b-8) 2,2,6,6-tetramethyl-4-piperidinol [CAS: #2403-88-5], (b-9) 2-(2-methoxyphenyl)ethylamine [CAS: #2045-79-6], (b-10) 2-(3,4-dimethoxyphenyl)ethylamine [CAS: #120-20-7], (b-11) N-isopropylbenzylamine [CAS: #102-97-6] and (b-12) N-butylbenzylamine [CAS: #2403-22-7].

The preferred amines used in the present invention are low toxic amines contained in the pharmaceuticals approved by Food and Drug Administration (FDA) in USA, with which active ingredients can form salts.

The particularly preferred amine in the present invention includes dibenzylamine.

In the present invention, the crystal comprising (2R)-2-propyloctanoic acid and dibenzylamine (hereinafter sometimes referred to as "crystal with dibenzylamine") may be produced by a process as mentioned below. The crystal with dibenzylamine produced by such a process was a new crystal comprising 2 molecules of (2R)-2-propyloctanoic acid and 1 molecule of dibenzylamine, as seen clearly from the results of elemental analysis as mentioned in Example below.

The crystal with dibenzylamine can be characterized by the following data. Specifically, the crystal is characterized by a chart (FIG. 1) of powdered X-ray diffraction spectrum obtained by irradiation of Cu—Kα ray or the diffraction angle (2θ) as shown in Table 1 below, the half width and relative intensity. In the present invention, the relative intensity is represented by the rate of the peaks to the highest peak which is regarded as 100%.

TABLE 1

Crystal with dibenzylamine

| Diffraction angle (2θ) (degree) | Half width (Å) | Relative intensity (%) |
|---|---|---|
| 15.27 | 5.80 | 64.9 |
| 17.03 | 5.20 | 34.5 |
| 19.04 | 4.66 | 100.0 |
| 19.99 | 4.44 | 85.7 |
| 21.36 | 4.16 | 25.8 |
| 22.91 | 3.88 | 80.4 |
| 24.21 | 3.67 | 89.1 |
| 26.09 | 3.41 | 30.7 |
| 26.70 | 3.34 | 28.9 |
| 28.42 | 3.14 | 23.8 |
| 30.83 | 2.90 | 24.6 |
| 34.06 | 2.63 | 22.3 |

The crystal with dibenzylamine can be characterized by a chart of infrared absorption (1R) spectrum measured by the KBr method (FIG. 2) or absorption peaks of 3434, 3068, 3036, 2957, 2926, 2872, 2853, 2756, 2621, 2454, 1948, 1638, 1498, 1466, 1457, 1415, 1379, 1342, 1321, 1212, 1141, 1112, 1096, 1044, 989, 936, 905, 812, 763, 744 and 694 cm$^{-1}$.

Further, the crystal with dibenzylamine is also characterized by a chart (FIG. 3) of differential scanning calorimetry (DSC) or by an endothermic peak at approximately 81.8° C.

The crystal with dibenzylamine is also characterized in that the specific rotation $[\alpha]_D^{20}$ is about −3.6 (c=2.00; ethanol) when the optical purity of the crystal is about 99.8% e.e.

The crystal with dibenzylamine disclosed in the present invention is characterized by the physicochemical properties as described herein, but the data such as respective spectra or specific rotation should not be construed strictly because they are somewhat variable substantially.

For example, in the powdered X-ray diffraction spectra in confirming the identity of crystals, the diffraction angle (2θ) or their overall patterns are important, and the relative intensity is somewhat variable depending on direction of crystal growth, size of particle, and the condition of measurement. In IR spectra in confirming the identity of crystals, the overall patterns are important but somewhat variable depending on the condition of measurement. Further, in DSC in confirming the identity of crystals, the overall patterns are important but somewhat variable depending on the condition of measurement.

In addition, for example, the specific rotation is also variable depending on the optical purity of crystal, concentration, solvent used in measurement, temperature, the presence or absence of impurities, and so on.

Therefore, any crystal in which the data or chart pattern in the powdered X-ray diffraction spectrum, IR spectrum and/or DSC are generally the same as that of the crystal with dibenzylamine or shows the same specific rotation, is included in the crystal with dibenzylamine of the present invention.

In the present invention, the crystal comprising (2R)-2-propyloctanoic acid and an amine of the above (a-1) to (a-16) or (b-2) to (b-12) may be produced according to the process as mentioned below. The crystals with amines produced according to such a process, all are new crystals.

These crystals can be characterized by the following data. Specifically, the crystal is characterized by a chart of powdered X-ray diffraction spectrum obtained by irradiation of Cu—Kα ray (FIG. 4, FIG. 6, FIG. 8, FIG. 10, FIG. 12, FIG. 14, FIG. 16, FIG. 18, FIG. 20, FIG. 22, FIG. 24, FIG. 26, FIG. 28, FIG. 30, FIG. 32, FIG. 34, FIG. 36, FIG. 38, FIG. 40, FIG. 42, FIG. 46, FIG. 48, FIG. 50, FIG. 52, FIG. 54, FIG. 56, FIG. 58) or the diffraction angle (2θ) as shown in Table 2 to Table 25 below, the half width and relative intensity.

TABLE 2

Crystal with (+)-dehydroabietylamine

| Diffraction angle (2θ) (degree) | Half width (Å) | Relative intensity (%) |
|---|---|---|
| 12.16 | 7.27 | 15.2 |
| 12.90 | 6.86 | 14.2 |
| 14.04 | 6.30 | 17.1 |
| 15.15 | 5.84 | 88.6 |
| 15.70 | 5.64 | 40.2 |
| 16.46 | 5.38 | 32.4 |
| 17.08 | 5.19 | 63.7 |
| 18.35 | 4.83 | 100.0 |
| 18.96 | 4.68 | 44.3 |
| 19.45 | 4.56 | 44.2 |
| 20.56 | 4.32 | 67.1 |
| 22.31 | 3.98 | 26.9 |
| 23.35 | 3.81 | 25.5 |
| 24.44 | 3.64 | 37.5 |
| 25.65 | 3.47 | 24.8 |

TABLE 3

Crystal with (−)-cis-myrtanylamine

| Diffraction angle (2θ) (degree) | Half width (Å) | Relative intensity (%) |
|---|---|---|
| 11.23 | 7.88 | 6.3 |
| 14.53 | 6.09 | 19.6 |
| 15.43 | 5.74 | 21.4 |
| 16.55 | 5.35 | 87.6 |
| 17.74 | 5.00 | 100.0 |
| 18.71 | 4.74 | 56.0 |
| 19.57 | 4.53 | 56.4 |
| 21.44 | 4.14 | 45.9 |
| 22.45 | 3.96 | 22.2 |
| 23.29 | 3.82 | 11.2 |
| 24.45 | 3.64 | 16.1 |
| 25.60 | 3.48 | 18.7 |
| 26.57 | 3.35 | 14.1 |
| 27.20 | 3.28 | 16.4 |
| 27.50 | 3.24 | 16.0 |
| 29.74 | 3.00 | 13.6 |
| 31.20 | 2.86 | 16.1 |
| 32.92 | 2.72 | 12.6 |
| 34.22 | 2.62 | 12.1 |
| 35.79 | 2.51 | 8.7 |
| 36.59 | 2.45 | 9.7 |

TABLE 4

Crystal with (R)-(+)-1-(p-tolyl)ethylamine

| Diffraction angle (2θ) (degree) | Half width (Å) | Relative intensity (%) |
|---|---|---|
| 11.34 | 7.79 | 24.4 |
| 12.01 | 7.36 | 8.7 |
| 12.81 | 6.91 | 31.7 |
| 13.69 | 6.46 | 6.7 |
| 15.08 | 5.87 | 8.8 |
| 16.15 | 5.48 | 45.5 |
| 17.47 | 5.07 | 20.9 |
| 18.84 | 4.71 | 100.0 |
| 20.08 | 4.42 | 28.2 |
| 20.68 | 4.29 | 71.7 |
| 22.03 | 4.03 | 19.3 |
| 23.00 | 3.86 | 89.2 |
| 24.14 | 3.68 | 27.1 |
| 25.65 | 3.47 | 54.2 |
| 27.41 | 3.25 | 29.2 |

TABLE 4-continued

Crystal with (R)-(+)-1-(p-tolyl)ethylamine

| Diffraction angle (2θ) (degree) | Half width (Å) | Relative intensity (%) |
|---|---|---|
| 28.22 | 3.16 | 17.1 |
| 29.92 | 2.98 | 14.6 |
| 30.99 | 2.88 | 14.0 |
| 32.64 | 2.74 | 15.6 |
| 33.22 | 2.70 | 14.6 |
| 34.46 | 2.60 | 12.3 |

TABLE 5

Crystal with (R)-(+)-1-(1-naphthyl)ethylamine

| Diffraction angle (2θ) (degree) | Half width (Å) | Relative intensity (%) |
|---|---|---|
| 10.97 | 8.06 | 14.4 |
| 13.38 | 6.61 | 58.1 |
| 15.84 | 5.59 | 48.9 |
| 16.91 | 5.24 | 31.0 |
| 17.67 | 5.02 | 40.8 |
| 19.31 | 4.59 | 54.2 |
| 20.46 | 4.34 | 34.3 |
| 21.52 | 4.13 | 43.2 |
| 22.21 | 4.00 | 100.0 |
| 23.49 | 3.78 | 67.5 |
| 24.41 | 3.64 | 24.2 |
| 25.11 | 3.54 | 24.1 |
| 26.78 | 3.33 | 22.7 |
| 28.12 | 3.17 | 14.7 |
| 28.96 | 3.08 | 21.3 |
| 31.28 | 2.86 | 20.6 |
| 33.79 | 2.65 | 13.8 |
| 35.87 | 2.50 | 12.9 |
| 36.77 | 2.44 | 12.4 |

TABLE 6

Crystal with (S)-(−)-1-(1-naphthyl)ethylamine

| Diffraction angle (2θ) (degree) | Half width (Å) | Relative intensity (%) |
|---|---|---|
| 12.41 | 7.13 | 22.8 |
| 13.71 | 6.45 | 24.6 |
| 14.05 | 6.30 | 20.6 |
| 15.12 | 5.86 | 41.4 |
| 16.27 | 5.45 | 35.1 |
| 16.80 | 5.27 | 54.0 |
| 17.57 | 5.04 | 57.3 |
| 18.72 | 4.74 | 53.3 |
| 19.35 | 4.58 | 94.0 |
| 19.96 | 4.45 | 57.4 |
| 21.00 | 4.23 | 74.1 |
| 21.50 | 4.13 | 57.6 |
| 22.41 | 3.96 | 100.0 |
| 23.56 | 3.77 | 27.5 |
| 23.95 | 3.71 | 28.0 |
| 25.55 | 3.48 | 49.7 |
| 26.21 | 3.40 | 41.1 |
| 27.79 | 3.21 | 32.9 |
| 28.56 | 3.12 | 25.9 |
| 30.92 | 2.89 | 26.0 |

TABLE 7

Crystal with L-tyrosinamide

| Diffraction angle (2θ) (degree) | Half width (Å) | Relative intensity (%) |
|---|---|---|
| 12.10 | 7.31 | 10.7 |
| 12.83 | 6.89 | 8.7 |
| 14.67 | 6.03 | 15.3 |
| 15.44 | 5.73 | 17.4 |
| 16.46 | 5.38 | 57.5 |
| 17.08 | 5.19 | 100.0 |
| 18.19 | 4.87 | 40.7 |
| 19.89 | 4.46 | 91.5 |
| 21.30 | 4.17 | 66.1 |
| 22.12 | 4.02 | 40.1 |
| 23.31 | 3.81 | 61.6 |
| 24.15 | 3.68 | 48.1 |
| 25.81 | 3.45 | 37.5 |
| 27.36 | 3.26 | 43.0 |
| 28.66 | 3.11 | 20.8 |
| 29.85 | 2.99 | 19.7 |
| 30.95 | 2.89 | 23.2 |
| 32.97 | 2.71 | 29.2 |
| 33.48 | 2.67 | 21.9 |
| 35.00 | 2.56 | 17.7 |
| 36.64 | 2.45 | 20.7 |

TABLE 8

Crystal with (1S,2R)-(+)-2-amino-1,2-diphenylethanol

| Diffraction angle (2θ) (degree) | Half width (Å) | Relative intensity (%) |
|---|---|---|
| 13.60 | 6.51 | 25.5 |
| 14.18 | 6.24 | 20.4 |
| 15.96 | 5.55 | 100.0 |
| 17.33 | 5.11 | 44.1 |
| 18.35 | 4.83 | 22.5 |
| 19.47 | 4.56 | 62.7 |
| 20.46 | 4.34 | 82.6 |
| 21.41 | 4.15 | 59.3 |
| 22.45 | 3.96 | 37.5 |
| 23.55 | 3.77 | 64.9 |
| 24.78 | 3.59 | 61.9 |
| 25.97 | 3.43 | 25.8 |
| 27.53 | 3.24 | 22.8 |
| 28.63 | 3.12 | 19.6 |
| 29.79 | 3.00 | 24.1 |
| 32.31 | 2.77 | 16.5 |
| 33.54 | 2.67 | 20.2 |
| 35.51 | 2.53 | 21.9 |

TABLE 9

Crystal with (1R,2S)-(−)-2-amino-1,2-diphenylethanol

| Diffraction angle (2θ) (degree) | Half width (Å) | Relative intensity (%) |
|---|---|---|
| 10.06 | 8.79 | 8.9 |
| 11.94 | 7.41 | 21.5 |
| 12.88 | 6.87 | 8.8 |
| 15.11 | 5.86 | 37.0 |
| 15.97 | 5.54 | 73.4 |
| 16.52 | 5.36 | 44.3 |
| 17.91 | 4.95 | 89.4 |
| 19.15 | 4.63 | 55.9 |
| 19.77 | 4.49 | 80.0 |
| 21.29 | 4.17 | 83.6 |
| 23.04 | 3.86 | 100.0 |
| 24.07 | 3.69 | 36.8 |
| 25.40 | 3.50 | 59.4 |
| 25.76 | 3.46 | 58.2 |

TABLE 9-continued

Crystal with (1R,2S)-(−)-2-amino-1,2-diphenylethanol

| Diffraction angle (2θ) (degree) | Half width (Å) | Relative intensity (%) |
|---|---|---|
| 28.44 | 3.14 | 27.0 |
| 29.57 | 3.02 | 23.2 |
| 30.70 | 2.91 | 27.4 |
| 35.72 | 2.51 | 26.0 |

TABLE 10

Crystal with (+)-cis-2-benzylaminocyclohexanemethanol

| Diffraction angle (2θ) (degree) | Half width (Å) | Relative intensity (%) |
|---|---|---|
| 10.49 | 8.43 | 6.5 |
| 12.01 | 7.36 | 9.8 |
| 13.37 | 6.62 | 5.2 |
| 15.92 | 5.56 | 14.1 |
| 16.68 | 5.31 | 18.7 |
| 17.90 | 4.95 | 100.0 |
| 19.83 | 4.47 | 28.8 |
| 21.16 | 4.20 | 34.2 |
| 22.75 | 3.91 | 13.9 |
| 24.34 | 3.65 | 9.4 |
| 26.06 | 3.42 | 12.5 |
| 27.68 | 3.22 | 13.5 |
| 28.56 | 3.12 | 10.8 |
| 30.37 | 2.94 | 9.9 |
| 32.05 | 2.79 | 11.1 |

TABLE 11

Crystal with (−)-cis-2-benzylaminocyclohexanemethanol

| Diffraction angle (2θ) (degree) | Half width (Å) | Relative intensity (%) |
|---|---|---|
| 10.01 | 8.83 | 6.9 |
| 12.38 | 7.15 | 28.3 |
| 15.35 | 5.77 | 24.7 |
| 16.29 | 5.44 | 27.7 |
| 17.99 | 4.93 | 100.0 |
| 19.02 | 4.66 | 39.6 |
| 20.00 | 4.44 | 68.1 |
| 21.52 | 4.13 | 23.5 |
| 21.85 | 4.06 | 28.8 |
| 22.84 | 3.89 | 24.8 |
| 23.93 | 3.71 | 15.3 |
| 24.87 | 3.58 | 21.4 |
| 25.46 | 3.50 | 27.2 |
| 28.03 | 3.18 | 21.2 |
| 29.91 | 2.99 | 17.5 |
| 31.21 | 2.86 | 16.7 |
| 35.00 | 2.56 | 11.3 |
| 35.89 | 2.50 | 13.1 |

TABLE 12

Crystal with (R)-(+)-2-amino-3-phenyl-1-propanol

| Diffraction angle (2θ) (degree) | Half width (Å) | Relative intensity (%) |
|---|---|---|
| 8.29 | 10.66 | 5.1 |
| 10.15 | 8.71 | 5.2 |
| 13.33 | 6.64 | 12.0 |
| 15.94 | 5.56 | 31.2 |
| 16.61 | 5.33 | 24.8 |
| 17.87 | 4.96 | 23.1 |

TABLE 12-continued

Crystal with (R)-(+)-2-amino-3-phenyl-1-propanol

| Diffraction angle (2θ) (degree) | Half width (Å) | Relative intensity (%) |
|---|---|---|
| 19.83 | 4.47 | 100.0 |
| 21.48 | 4.13 | 41.0 |
| 24.51 | 3.63 | 14.7 |
| 26.22 | 3.40 | 27.5 |
| 27.48 | 3.24 | 17.4 |
| 30.09 | 2.97 | 19.8 |
| 32.33 | 2.77 | 11.6 |
| 33.73 | 2.66 | 10.6 |
| 36.36 | 2.47 | 10.8 |

TABLE 13

Crystal with (R)-(+)-1-(4-bromophenyl)ethylamine

| Diffraction angle (2θ) (degree) | Half width (Å) | Relative intensity (%) |
|---|---|---|
| 9.47 | 9.33 | 16.2 |
| 11.43 | 7.74 | 23.8 |
| 12.02 | 7.36 | 27.5 |
| 15.06 | 5.88 | 33.5 |
| 16.10 | 5.50 | 23.1 |
| 17.45 | 5.08 | 21.5 |
| 19.00 | 4.67 | 100.0 |
| 20.17 | 4.40 | 47.4 |
| 20.69 | 4.29 | 34.0 |
| 22.01 | 4.04 | 51.5 |
| 23.12 | 3.84 | 82.2 |
| 24.11 | 3.69 | 68.3 |
| 25.55 | 3.48 | 46.5 |
| 27.43 | 3.25 | 62.7 |
| 29.75 | 3.00 | 44.1 |
| 32.38 | 2.76 | 35.8 |
| 34.67 | 2.59 | 32.7 |
| 35.94 | 2.50 | 31.5 |

TABLE 14

Crystal with (R)-(+)-1-phenylpropylamine

| Diffraction angle (2θ) (degree) | Half width (Å) | Relative intensity (%) |
|---|---|---|
| 12.49 | 7.08 | 28.2 |
| 13.98 | 6.33 | 17.6 |
| 14.44 | 6.13 | 42.9 |
| 15.63 | 5.66 | 15.1 |
| 16.38 | 5.41 | 15.1 |
| 18.50 | 4.79 | 24.7 |
| 19.18 | 4.62 | 51.2 |
| 20.53 | 4.32 | 20.6 |
| 21.17 | 4.19 | 72.8 |
| 21.76 | 4.08 | 100.0 |
| 22.61 | 3.93 | 39.7 |
| 23.35 | 3.81 | 36.6 |
| 24.23 | 3.67 | 52.0 |
| 25.36 | 3.51 | 52.3 |
| 26.46 | 3.37 | 16.1 |
| 28.22 | 3.16 | 13.3 |
| 28.81 | 3.10 | 18.7 |
| 29.75 | 3.00 | 17.2 |
| 30.62 | 2.92 | 15.6 |
| 31.41 | 2.85 | 12.3 |
| 32.45 | 2.76 | 13.2 |
| 33.49 | 2.67 | 11.5 |
| 35.16 | 2.55 | 14.7 |
| 35.72 | 2.51 | 15.0 |

TABLE 15

Crystal with 1,2-diphenylethylamine

| Diffraction angle (2θ) (degree) | Half width (Å) | Relative intensity (%) |
|---|---|---|
| 12.38 | 7.14 | 12.3 |
| 13.37 | 6.62 | 25.1 |
| 14.04 | 6.30 | 18.2 |
| 16.50 | 5.37 | 56.3 |
| 17.73 | 5.00 | 100.0 |
| 18.80 | 4.72 | 77.8 |
| 19.83 | 4.47 | 77.3 |
| 21.17 | 4.19 | 34.2 |
| 22.80 | 3.90 | 44.5 |
| 24.07 | 3.69 | 41.2 |
| 25.14 | 3.54 | 40.0 |
| 27.06 | 3.29 | 29.8 |
| 28.35 | 3.15 | 20.0 |
| 29.25 | 3.05 | 18.5 |
| 30.66 | 2.91 | 18.6 |

TABLE 16

Crystal with benzhydrylamine

| Diffraction angle (2θ) (degree) | Half width (Å) | Relative intensity (%) |
|---|---|---|
| 13.58 | 6.52 | 8.6 |
| 14.50 | 6.11 | 13.5 |
| 16.05 | 5.52 | 15.4 |
| 16.85 | 5.26 | 43.4 |
| 18.38 | 4.82 | 42.9 |
| 19.27 | 4.60 | 60.7 |
| 21.28 | 4.17 | 100.0 |
| 21.63 | 4.10 | 76.2 |
| 22.70 | 3.91 | 42.5 |
| 23.46 | 3.79 | 52.0 |
| 24.59 | 3.62 | 21.2 |
| 25.85 | 3.44 | 35.0 |
| 26.48 | 3.36 | 40.7 |
| 26.93 | 3.31 | 27.8 |
| 28.31 | 3.15 | 19.5 |
| 30.03 | 2.97 | 15.9 |
| 31.38 | 2.85 | 17.5 |
| 33.55 | 2.67 | 15.8 |
| 36.60 | 2.45 | 15.3 |

TABLE 17

Crystal with cyclohexylamine

| Diffraction angle (2θ) (degree) | Half width (Å) | Relative intensity (%) |
|---|---|---|
| 10.98 | 8.05 | 8.9 |
| 11.37 | 7.77 | 11.6 |
| 12.84 | 6.89 | 18.0 |
| 14.68 | 6.03 | 15.2 |
| 15.86 | 5.58 | 33.3 |
| 17.03 | 5.20 | 39.0 |
| 17.62 | 5.03 | 42.1 |
| 18.82 | 4.71 | 100.0 |
| 20.09 | 4.42 | 54.8 |
| 20.90 | 4.25 | 71.7 |
| 21.83 | 4.07 | 75.9 |
| 22.54 | 3.94 | 35.6 |
| 25.40 | 3.50 | 25.2 |
| 25.98 | 3.43 | 26.5 |
| 27.91 | 3.19 | 19.8 |
| 29.07 | 3.07 | 21.4 |
| 30.03 | 2.97 | 21.5 |
| 31.64 | 2.83 | 18.8 |

TABLE 17-continued

Crystal with cyclohexylamine

| Diffraction angle (2θ) (degree) | Half width (Å) | Relative intensity (%) |
|---|---|---|
| 33.24 | 2.69 | 16.0 |
| 35.89 | 2.50 | 17.5 |

TABLE 18

Crystal with dicyclohexylamine

| Diffraction angle (2θ) (degree) | Half width (Å) | Relative intensity (%) |
|---|---|---|
| 11.16 | 7.92 | 12.3 |
| 12.22 | 7.24 | 5.9 |
| 14.59 | 6.07 | 8.6 |
| 15.30 | 5.78 | 14.6 |
| 16.75 | 5.29 | 19.1 |
| 18.28 | 4.85 | 35.2 |
| 19.13 | 4.64 | 100.0 |
| 19.80 | 4.48 | 38.1 |
| 21.27 | 4.17 | 25.0 |
| 22.42 | 3.96 | 26.1 |
| 23.51 | 3.78 | 25.9 |
| 25.20 | 3.53 | 20.3 |
| 30.38 | 2.94 | 12.4 |
| 31.17 | 2.87 | 15.4 |
| 33.03 | 2.71 | 12.9 |

TABLE 19

Crystal with cycloheptylamine

| Diffraction angle (2θ) (degree) | Half width (Å) | Relative intensity (%) |
|---|---|---|
| 7.98 | 11.07 | 26.6 |
| 12.29 | 7.20 | 20.7 |
| 14.68 | 6.03 | 22.2 |
| 16.19 | 5.47 | 16.3 |
| 17.39 | 5.10 | 29.1 |
| 18.34 | 4.83 | 71.6 |
| 19.07 | 4.65 | 86.4 |
| 20.01 | 4.43 | 100.0 |
| 20.98 | 4.23 | 28.7 |
| 22.05 | 4.03 | 22.8 |
| 24.19 | 3.68 | 21.5 |
| 25.56 | 3.48 | 21.7 |
| 27.02 | 3.30 | 22.0 |
| 30.80 | 2.90 | 21.4 |
| 32.65 | 2.74 | 23.1 |

TABLE 20

Crystal with N-ethylcyclohexylamine

| Diffraction angle (2θ) (degree) | Half width (Å) | Relative intensity (%) |
|---|---|---|
| 7.70 | 11.47 | 100.0 |
| 9.27 | 9.53 | 8.9 |
| 12.09 | 7.31 | 8.4 |
| 14.09 | 6.28 | 7.7 |
| 14.60 | 6.06 | 10.7 |
| 15.21 | 5.82 | 7.2 |
| 16.62 | 5.33 | 5.2 |
| 17.85 | 4.96 | 15.0 |
| 18.19 | 4.87 | 8.5 |
| 19.82 | 4.48 | 23.2 |
| 20.78 | 4.27 | 16.6 |

TABLE 20-continued

Crystal with N-ethylcyclohexylamine

| Diffraction angle (2θ) (degree) | Half width (Å) | Relative intensity (%) |
|---|---|---|
| 21.74 | 4.09 | 10.6 |
| 22.61 | 3.93 | 9.4 |
| 23.42 | 3.80 | 8.8 |
| 25.09 | 3.55 | 8.2 |

TABLE 21

Crystal with 2,2,6,6-tetramethyl-4-piperidinol

| Diffraction angle (2θ) (degree) | Half width (Å) | Relative intensity (%) |
|---|---|---|
| 9.11 | 9.70 | 100.0 |
| 13.47 | 6.57 | 16.3 |
| 14.84 | 5.96 | 9.2 |
| 17.25 | 5.14 | 25.8 |
| 18.18 | 4.88 | 17.9 |
| 19.93 | 4.45 | 21.8 |
| 21.24 | 4.18 | 19.7 |
| 22.30 | 3.98 | 14.6 |
| 23.80 | 3.74 | 11.8 |
| 24.78 | 3.59 | 11.0 |
| 25.96 | 3.43 | 11.5 |
| 30.28 | 2.95 | 8.5 |

TABLE 22

Crystal with 2-(2-methoxyphenyl)ethylamine

| Diffraction angle (2θ) (degree) | Half width (Å) | Relative intensity (%) |
|---|---|---|
| 9.56 | 9.25 | 16.1 |
| 12.26 | 7.21 | 30.0 |
| 13.28 | 6.66 | 18.3 |
| 13.93 | 6.35 | 27.0 |
| 15.34 | 5.77 | 53.4 |
| 15.99 | 5.54 | 35.3 |
| 16.50 | 5.37 | 32.5 |
| 17.31 | 5.12 | 23.5 |
| 18.57 | 4.77 | 32.3 |
| 19.15 | 4.63 | 58.6 |
| 20.04 | 4.43 | 100.0 |
| 20.74 | 4.28 | 90.6 |
| 21.65 | 4.10 | 69.2 |
| 23.52 | 3.78 | 44.1 |
| 24.48 | 3.63 | 35.2 |
| 25.76 | 3.46 | 37.7 |
| 26.35 | 3.38 | 45.4 |
| 27.52 | 3.24 | 28.1 |
| 29.20 | 3.06 | 34.4 |
| 30.87 | 2.89 | 16.7 |
| 32.10 | 2.79 | 17.0 |
| 35.28 | 2.54 | 17.1 |

TABLE 23

Crystal with 2-(3,4-dimethoxyphenyl)ethylamine

| Diffraction angle (2θ) (degree) | Half width (Å) | Relative intensity (%) |
|---|---|---|
| 8.56 | 10.32 | 15.3 |
| 10.44 | 8.47 | 17.8 |
| 11.98 | 7.38 | 7.7 |
| 14.64 | 6.05 | 15.0 |
| 15.34 | 5.77 | 23.6 |

TABLE 23-continued

Crystal with 2-(3,4-dimethoxyphenyl)ethylamine

| Diffraction angle (2θ) (degree) | Half width (Å) | Relative intensity (%) |
|---|---|---|
| 16.88 | 5.25 | 28.3 |
| 18.73 | 4.73 | 11.9 |
| 19.17 | 4.63 | 10.3 |
| 20.57 | 4.31 | 96.5 |
| 22.05 | 4.03 | 21.6 |
| 22.95 | 3.87 | 100.0 |
| 25.22 | 3.53 | 19.2 |
| 27.65 | 3.22 | 9.5 |
| 29.07 | 3.07 | 8.0 |
| 32.33 | 2.77 | 7.8 |

TABLE 24

Crystal with N-isopropylbenzylamine

| Diffraction angle (2θ) (degree) | Half width (Å) | Relative intensity (%) |
|---|---|---|
| 7.97 | 11.08 | 100.0 |
| 11.34 | 7.80 | 19.8 |
| 12.91 | 6.85 | 11.8 |
| 13.36 | 6.62 | 7.8 |
| 15.27 | 5.80 | 16.1 |
| 17.21 | 5.15 | 30.1 |
| 17.68 | 5.01 | 18.8 |
| 18.83 | 4.71 | 39.2 |
| 20.06 | 4.42 | 19.3 |
| 21.88 | 4.06 | 44.2 |
| 23.29 | 3.82 | 21.2 |
| 24.01 | 3.70 | 15.9 |
| 26.76 | 3.33 | 11.4 |
| 27.67 | 3.22 | 9.5 |
| 31.83 | 2.81 | 8.8 |
| 32.94 | 2.72 | 9.1 |

TABLE 25

Crystal with N-butylbenzylamine

| Diffraction angle (2θ) (degree) | Half width (Å) | Relative intensity (%) |
|---|---|---|
| 11.71 | 7.55 | 10.1 |
| 13.84 | 6.39 | 12.8 |
| 19.81 | 4.48 | 38.2 |
| 20.67 | 4.29 | 100.0 |
| 24.64 | 3.61 | 22.3 |

These crystals are characterized by the chart of IR spectra measured by the ATR method (FIG. 5, FIG. 7, FIG. 9, FIG. 11, FIG. 13, FIG. 15, FIG. 17, FIG. 19, FIG. 21, FIG. 23, FIG. 25, FIG. 27, FIG. 29, FIG. 31, FIG. 33, FIG. 35, FIG. 37, FIG. 39, FIG. 41, FIG. 43, FIG. 47, FIG. 49, FIG. 51, FIG. 53, FIG. 55, FIG. 57, FIG. 59) and the following absorption peaks.

(a-1) Crystal with (+)-dehydroabietylamine:
2954, 2925, 2850, 2663, 2197, 1560, 1534, 1497, 1456, 1436, 1394, 1360, 1298, 1210, 1173, 1147, 1109, 1056, 1005, 911, 883, 854, 822, 777, 752, 726, 674, 630 cm$^{-1}$.

(a-2) Crystal with (R)-(−)-2-phenylglycinol:
3034, 2953, 2926, 2854, 2668, 2509, 2143, 1640, 1605, 1522, 1457, 1400, 1376, 1339, 1316, 1281, 1228, 1207, 1186, 1119, 1065, 1049, 994, 919, 891, 854, 787, 758, 700, 537 cm$^{-1}$.

(a-3) Crystal with (S)-(+)-2-phenylglycinol:
3033, 2953, 2925, 2870, 2850, 2670, 2516, 2155, 1641, 1567, 1524, 1496, 1457, 1433, 1393, 1308, 1208, 1182, 1149, 1112, 1067, 1054, 1030, 1000, 920, 893, 860, 801, 758, 701 cm$^{-1}$.

(a-4) Crystal with (−)-cis-myrtanylamine:
2989, 2952, 2919, 2869, 2852, 2611, 2196, 1626, 1517, 1458, 1397, 1363, 1320, 1230, 1214, 1139, 1116, 1035, 1005, 978, 919, 874, 848, 809, 779, 747, 721, 637 cm$^{-1}$.

(a-5) Crystal with (R)-(+)-1-(p-tolyl)ethylamine:
2954, 2925, 2856, 2702, 2536, 2210, 1621, 1567, 1518, 1464, 1440, 1405, 1381, 1315, 1306, 1231, 1172, 1111, 1090, 1021, 993, 898, 868, 849, 813, 779, 744, 722, 685 cm$^{-1}$.

(a-6) Crystal with (R)-(+)-1-(1-naphthyl)ethylamine:
2952, 2924, 2854, 2759, 2582, 2180, 1629, 1571, 1509, 1467, 1454, 1433, 1402, 1389, 1378, 1335, 1305, 1275, 1253, 1231, 1173, 1110, 1076, 1004, 950, 900, 860, 801, 774 cm$^{-1}$.

(a-7) Crystal with (S)-(−)-1-(1-naphthyl)ethylamine:
2952, 2922, 2850, 2219, 1624, 1601, 1557, 1514, 1467, 1454, 1395, 1377, 1317, 1279, 1223, 1177, 1108, 1075, 1030, 1002, 950, 923, 898, 860, 849, 799, 775, 749 cm$^{-1}$.

(a-8) Crystal with L-tyrosinamide:
3430, 2953, 2923, 2856, 1673, 1559, 1512, 1449, 1407, 1376, 1349, 1324, 1266, 1242, 1210, 1175, 1108, 1078, 1037, 997, 850, 830, 785, 736, 645 cm$^{-1}$.

(a-9) Crystal with (1S,2R)-(+)-2-amino-1,2-diphenylethanol:
2925, 2851, 1617, 1559, 1507, 1455, 1406, 1320, 1272, 1204, 1134, 1081, 1047, 1007, 919, 848, 782, 765, 742, 699, 567 cm$^{-1}$.

(a-10) Crystal with (1R,2S)-(−)-2-amino-1,2-diphenylethanol:
3275, 2953, 2925, 2856, 2605, 1617, 1560, 1542, 1508, 1455, 1408, 1307, 1277, 1239, 1205, 1132, 1110, 1081, 1046, 1006, 921, 907, 849, 811, 783, 765, 742, 700 cm$^{-1}$.

(a-11) Crystal with (+)-cis-2-benzylaminocyclohexanemethanol:
3034, 2951, 2926, 2853, 1622, 1526, 1498, 1450, 1406, 1341, 1310, 1261, 1218, 1141, 1117, 1087, 1063, 1051, 1034, 1013, 974, 914, 862, 841, 812, 785, 750, 696, 645 cm$^{-1}$.

(a-12) Crystal with (−)-cis-2-benzylaminocyclohexanemethanol:
3033, 2949, 2925, 2854, 1622, 1524, 1497, 1454, 1397, 1341, 1324, 1261, 1219, 1115, 1087, 1075, 1061, 1037, 1010, 975, 914, 781, 750, 697, 634 cm$^{-1}$.

(a-13) Crystal with (S)-(−)-2-amino-3-phenyl-1-propanol:
3241, 3029, 2953, 2925, 2853, 2546, 2163, 1623, 1576, 1541, 1497, 1456, 1398, 1374, 1338, 1285, 1206, 1175, 1113, 1093, 1065, 1031, 997, 944, 915, 850, 806, 740, 697 cm$^{-1}$.

(a-14) Crystal with (R)-(+)-2-amino-3-phenyl-1-propanol:
3255, 3065, 3030, 2954, 2925, 2854, 2547, 2153, 1622, 1574, 1541, 1496, 1456, 1395, 1375, 1338, 1309, 1279, 1207, 1175, 1113, 1093, 1065, 1031, 997, 945, 913, 850, 787, 740, 697 cm$^{-1}$.

(a-15) Crystal with R)-(+)-1-(4-bromophenyl)ethylamine:
2954, 2925, 2855, 2703, 2195, 1621, 1571, 1515, 1491, 1466, 1440, 1404, 1381, 1306, 1281, 1231, 1186, 1110, 1090, 1011, 898, 850, 832, 819, 779, 742, 725, 716, 686 cm$^{-1}$.

(a-16) Crystal with (R)-(+)-1-phenylpropylamine:
2950, 2926, 2855, 2665, 2215, 1622, 1561, 1525, 1457, 1436, 1400, 1380, 1329, 1297, 1274, 1214, 1185, 1153, 1110, 1032, 998, 913, 892, 849, 778, 760, 750, 741, 695, 673 cm$^{-1}$.

(b-2) Crystal with 1,2-diphenylethylamine:
3030, 2953, 2925, 2852, 2663, 2176, 1627, 1536, 1497, 1467, 1455, 1431, 1396, 1338, 1310, 1275, 1232, 1110, 1074, 1024, 976, 935, 910, 846, 795, 775, 758, 740, 697 cm$^{-1}$.

(b-3) Crystal with benzhydrylamine:
2995, 2925, 2853, 2614, 2194, 1617, 1573, 1519, 1497, 1457, 1446, 1395, 1303, 1226, 1198, 1151, 1075, 1032, 1010, 998, 917, 837, 809, 755, 735, 695, 641, 542 cm$^{-1}$.

(b-4) Crystal with cyclohexylamine:
2922, 2855, 2625, 2569, 2224, 1634, 1525, 1455, 1399, 1340, 1313, 1285, 1246, 1140, 1115, 1073, 1050, 920, 891, 849, 801, 780, 748, 641, 554 cm$^{-1}$.

(b-5) Crystal with dicyclohexylamine:
2926, 2853, 1622, 1524, 1488, 1455, 1401, 1352, 1306, 1253, 1186, 1113, 1084, 1064, 1037, 980, 921, 887, 849, 805, 758, 640, 596 cm$^{-1}$.

(b-6) Crystal with cycloheptylamine:
2924, 1624, 1523, 1457, 1396 cm$^{-1}$.

(b-7) Crystal with N-ethylcyclohexylamine:
2925, 1622, 1531, 1449, 1402 cm$^{-1}$.

(b-8) Crystal with 2,2,6,6-tetramethyl-4-piperidinol:
3272, 2927, 1605, 1522 cm$^{-1}$.

(b-9) Crystal with 2-(2-methoxyphenyl)ethylamine:
2921, 1634, 1494, 1242 cm$^{-1}$.

(b-10) Crystal with 2-(3,4-dimethoxyphenyl)ethylamine:
2920, 1515, 1449, 1402, 1237 cm$^{-1}$.

(b-11) Crystal with N-isopropylbenzylamine:
2926, 1529, 1442, 1401 cm$^{-1}$.

(b-12) Crystal with N-butylbenzylamine:
2925, 1545, 1458, 1398 cm$^{-1}$.

The crystals with the above (a-1) to (a-16) or (b-2) to (b-12) are also characterized by their physicochemical properties as described herein in the same way as in the above crystal with dibenzylamine, but the spectral data should not be construed strictly because they are somewhat variable substantially.

The crystal comprising (2R)-2-propyloctanoic acid and an amine obtained in the present invention is per se excellent in availability as a bulk drug of pharmaceuticals since it is (1) stable as a material, (2) possible to stably supply in large quantities, and/or (3) relatively readily convertible into a pharmaceutical preparation such as tablets.

Pharmaceutical compositions in which these crystals can be used as bulk drugs include, for example, solid compositions for oral administration, liquid compositions for oral administration, injections, agents for external use and suppositories for parenteral administration, and the like. Particularly, solid compositions such as solid compositions for oral administration, agents for external use and suppositories are preferable by utilizing such characterization that solids as crystals can be obtained.

Solid compositions for oral administration include tablets, pills, capsules, dispersible powders, granules and the like. Capsules include hard capsules and soft capsules.

The solid composition for oral administration is used by formulating a crystal comprising (2R)-2-propyloctanoic acid and amine (hereinafter referred to as "active compounds") as it is or as a mixture with an excipient (e.g., lactose, mannitol, glucose, microcrystalline cellulose, starch, etc.), a binding agent (e.g., hydroxypropylcellulose, polyvinylpyrrolidone, magnesium aluminometasilicate, etc.), a disintegrating agent (e.g., calcium disodium ethylenediaminetetraacetate, etc.), a lubricant (e.g., magnesium stearate, etc.), a stabilizer (e.g., antioxidant (e.g., sulfite, sodium pyrosulfife, ascorbic acid, etc.), etc.), a solubilizer (e.g., glutamic acid, aspartic acid, polysorbates (e.g., POLYSORBATE 20, POLYSORBATE 60, POLYSORBATE 65, POLYSORBATE 80, etc.), macrogols (e.g., MACROGOL 200, MACROGOL 400, MACROGOL 1000, MACROGOL 1500, MACROGOL 4000, MACROGOL 6000, MACROGOL 20000, etc.), ethanol, glycerine, carboxymethyl cellulose, etc.) or the like according to the generally used methods. Also, if necessary, they may be coated with a coating agent (e.g., sugar, gelatin, hydroxypropyl cellulose, hydroxypropylmethyl cellulose phthalate, etc.), or be coated with two or more films. Moreover, capsules of absorbable materials such as gelatin are included.

Liquid compositions for oral administration include pharmaceutically acceptable solutions, suspensions, emulsions, syrups, elixirs and the like. In such liquid compositions, one or more of the active compounds may be dissolved, suspended or emulsified into diluent(s) commonly used in the art (such as purified water, ethanol, a mixture thereof, etc.). Besides such liquid forms may also comprise some additives, such as wetting agents, suspending agents, emulsifying agents, sweetening agents, flavoring agents, aroma, preservative or buffering agent.

Injections for parenteral administration include solutions, suspensions and emulsions, solid injections which are to be dissolved or suspended in solvents upon use, and the like. The injections are prepared by dissolving, suspending or emulsifying the active substances in a solvent. Examples of the solvent include distilled water for injection, physiological saline, plant oil, alcohols such as propylene glycol, polyethylene glycol and ethanol, combinations thereof, and the like. Further, the injection may contain a stabilizer (e.g., antioxidant (e.g., sulfite, sodium pyrosulfife, ascorbic acid, etc.), etc.), a solubilizer (e.g., glutamic acid, arpartic acid, polysorbates (e.g., POLYSORBATE 20, POLYSORBATE 60, POLYSORBATE 65, POLYSORBATE 80, etc.), macrogols (e.g., MACROGOL 200, MACROGOL 400, MACROGOL 1000, MACROGOL 1500, MACROGOL 4000, MACROGOL 6000, MACROGOL 20000, etc.), ethanol, glycerine, carboxymethyl cellulose, etc.), a solubilizing auxiliary agent such as glutamic acid, aspartic acid and POLYSORBATE 80 (registered trade mark) etc.), a pH adjusting agent (e.g., hydrochloric acid, citric acid, sodium citrate, acetic acid, tartaric acid, succinic acid, arginine, monoethanolamine, monoethanolamine, triethanolamine, meglumine, sodium hydroxide, potassium hydroxide, sodium bicarbonate, sodium carbonate, etc.), a suspending agent, an emulsifying agent, a soothing agent (e.g., chlorobutanol, creatinine, inositol, etc.), a buffering agent (e.g., phosphoric acid, trisodium phosphate, dibasic sodium phosphate, dibasic potassium phosphate, potassium dihydrogen phosphate, sodium dihydrogen phosphate, etc.), a preservative agent (e.g., methyl parahydroxybenzoate, ethyl parahydroxybenzoate, propyl parahydroxybenzoate, butyl methyl parahydroxybenzoate, etc.) and the like. The injection may be sterilized in the final step of the preparation process or the whole preparation process may be prepared under sterile conditions. The liquid injection may be used as it is or may be used by dissolving it in an appropriate solvent (e.g., distilled water for injection, physiological saline, various infusions, etc.). Also, the solid injection (e.g., freeze-dry product, etc.) is used by dissolving it in a solvent (e.g., distilled water for injection, physiological saline, carbohydrate solution, etc.) upon use, and if desired, by further diluting it by an appropriate medium for dilution (e.g., distilled water for injection, physiological saline, various infusions, etc.).

The agents for external use for parenteral administration include, for example, ointments, gels, creams, poultices, adhesive preparations, liniments, air sprays, inhalants, sprays, eye-drops, nasal-drops and the like. The agents for external use can be prepared by formulating the active substance by a known method or a generally used formulation method.

Other compositions for parenteral administration include suppositories for intrarectal administration, pessaries for intravaginal administration, and the like. These preparations can be prepared by formulating the active substance by a known method or a generally used formulation method.

Process for Production of the Compounds of the Present Invention:

The crystal comprising (2R)-2-propyloctanoic acid and an amine in the present invention (hereinafter abbreviated to crystal of the present invention) can be produced by the process as mentioned below, or its relative process, or the process as described in Examples.

The crystal of the present invention can be produced by dissolving (2R)-2-propyloctanoic acid in water and/or an organic solvent [for example, alcohol solvent (e.g., methanol, ethanol, isopropyl alcohol, etc.), ether solvent (e.g., diethyl ether, methyl t-butyl ether, dimethoxyethane, diethylene glycol dimethyl ether, tetrahydrofuran, 1,4-dioxane, etc.), ketone solvent (e.g., acetone, 2-butanone, etc.), ester solvent (e.g., ethyl acetate, diethyl carbonate, etc.), nitrile solvent (e.g., acetonitrile, etc.), aliphatic hydrocarbon solvent (e.g., n-hexane, n-heptane, cyclohexane, etc.), aromatic hydrocarbon solvent (e.g., benzene, toluene, xylene, etc.) and the like, and a mixture of them at an optional ratio], adding about 0.5-about 1.1 equivalent of the above amine, then stirring the resulting mixture at a temperature of about 40 to about 100° C. for a period of about 5 minutes to about 60 minutes, then cooling it at a temperature of about −20 to about 20° C., and stirring it at the same temperature for a period of about 5 to about 60 minutes to yield precipitate. The precipitated crystals are collected by filtration, washed with the above solvent, and dried to give the objective crystals.

Since (2R)-2-propyloctanoic acid is an oil, this is mixed with the above amine without using any solvent, and the mixture is treated in the same manner as described above to give the objective crystal of the present invention.

The (2R)-2-propyloctanoic acid used in production of the crystal as a starting material in the present invention is a known compound, and can be produced by the known processes as described in, for example, JP Patent 3032447, JP Patent 3084345, EP Patent 0632008, EP Patent 1078921, U.S. Pat. No. 6,608,221, WO03/051852, WO03/097851, and WO04/110972; or according to the process as described in Examples as mentioned below; or in proper combination of those processes.

Furthermore, in the present invention, a process for producing an optically highly pure (2R)-2-propyloctanoic acid is disclosed. In such a process, the crystal with dibenzylamine, among the crystals comprising (2R)-2-propyloctanoic acid and amines, may be used. That is, the crystal is per se useful as a bulk drug in production of pharmaceuticals as mentioned above, and also useful as an intermediate for obtaining optically highly pure (2R)-2-propyloctanoic acid.

Such a process, i.e. process for producing optically highly pure (2R)-2-propyloctanoic acid using the crystal with dibenzylamine as an intermediate, may be carried out as follows.

That is, (2R)-2-propyloctanoic acid as a starting material and an optically inactive amine (for example, dibenzylamine) are dissolved in a solvent to give a solution, which is applied to the following steps (1) to (3):

(1) a step of preferentially crystallizing the crystal comprising (2R)-2-propyloctanoic acid and an optically inactive amine out of the solution;

(2) a step of separating and collecting the precipitated crystal;

(3) a step of dissolving the crystal in a solvent to give a solution.

This process is repeated with optional frequency to preferentially crystallizing the crystal comprising (2R)-2-propyloctanoic acid and the optically inactive amine, from which crystal (2R)-2-propyloctanoic acid is recovered in a free form. When the steps (1) to (3) are repeated in optional frequency, such an operation is sometimes regarded as recrystallization. The recrystallization may be repeated again and again, but in view of efficiency it may preferably be repeated 0 to 5 times, more preferably 0 to 3 times and particularly 0 to 1 time.

One specific example of these steps is described in Example below, but in general, the step may be carried out as follows. In this connection, all the step specifically not indicated below may be carried out according to the known process.

First, the procedure for dissolving (2R)-2-propyloctanoic acid as a starting material and an optically inactive amine (e.g., dibenzylamine) in a solvent to give a solution, may be carried out as mentioned above by dissolving (2R)-2-propyloctanoic acid as a starting material and about 0.5 to about 1.1 equivalent of an optically inactive amine (e.g., dibenzylamine) in water and/or an organic solvent [for example, alcohol solvent (e.g., methanol, ethanol, isopropyl alcohol, etc.), ether solvent (e.g., diethyl ether, methyl t-butyl ether, dimethoxyethane, diethylene glycol dimethyl ether, tetrahydrofuran, 1,4-dioxane, etc.), ketone solvent (e.g., acetone, 2-butanone, etc.), ester solvent (e.g., ethyl acetate, diethyl carbonate, etc.), nitrile solvent (e.g., acetonitrile, etc.), aliphatic hydrocarbon solvent (e.g., n-hexane, n-heptane, cyclohexane, etc.), aromatic hydrocarbon solvent (e.g., benzene, toluene, xylene, etc.) or a mixture of these solvents at an optional rate]. The (2R)-2-propyloctanoic acid used as a starting material may be used in an optical purity of about 50% e.e. or more. Preferably, (2R)-2-propyloctanoic acid may be used in an optical purity of about 70% e.e. or more, more preferably in about 80% e.e. or more, particularly, about 90% e.e. or more.

The step of preferentially crystallizing the crystal out of the solution is carried out in the same manner as above by stirring the solution at a temperature of about 40 to about 100° C. for a period of about 5 to about 60 minutes, followed by cooling to about −20° C. to 20° C. and continuing the stirring for about 5 to about 60 minutes. When dibenzylamine is used as an amine, in this step, the crystal comprising (2R)-2-propyloctanoic acid and dibenzylamine can be crystallized preferentially to the crystal comprising (2S)-2-propyloctanoic acid and dibenzylamine (preferential crystallization). Thus, much more optically pure (2R)-2-propyloctanoic acid, preferably of the optical purity of over 99.5% e.e., than the starting (2R)-2-propyloctanoic acid, can be obtained by separating a free form of (2R)-2-propyloctanoic acid.

Separation of the free form of (2R)-2-propyloctanoic acid from the isolated crystal of (2R)-2-propyloctanoic acid with an amine (e.g., dibenzylamine) may be conducted, for example, according to the following known method.

That is, an aqueous solution of about 1 to about 5 equivalent of inorganic base (e.g., potassium hydroxide, sodium hydroxide, lithium hydroxide, calcium hydroxide, etc.) is added to the crystal, and the mixture is stirred for a period of about 5 to about 30 minutes and then back-extracted with addition of an organic solvent [for example, ether solvent (e.g., diethyl ether, methyl t-butyl ether, etc.), ester solvent (e.g., ethyl acetate, isopropyl acetate, diethyl carbonate, etc.), aliphatic hydrocarbon solvent (e.g., n-hexane, n-heptane, cyclohexane, etc.), or a mixture of them at an optional rate]. The resulting aqueous layer is acidified with addition of an inorganic acid (e.g., hydrochloric acid, sulfuric acid, etc.) at about 0 to about 20° C. and extracted with an extraction solvent [for example, ether solvent (e.g., diethyl ether, methyl t-butyl ether, etc.), ester solvent (e.g., ethyl acetate, isopropyl acetate, diethyl carbonate, etc.), aliphatic hydrocarbon solvent (e.g., n-hexane, n-heptane, cyclohexane, etc.), or a mixture of them at an optional rate]. Thus resulting organic layer is washed, concentrated, and purified to give a free form of (2R)-2-propyloctanoic acid.

It is very important to obtain an optically highly pure compound (bulk drug) in development of pharmaceuticals, and the purity is required to be close to 100% without limit. Therefore, it is a very important problem in development of pharmaceuticals to find a process for enhancing the optical purity and an intermediate for use in such a process.

In general, it is well known that a carboxyl-containing compound which contains its racemate or its R-isomer or S-isomer preferentially can be crystallized with an optically active amine to increase the optical purity. For example, (2R)-2-propyloctanoic acid is known to be optically purified by using an optically active (R)-(+)-1-phenylethylamine (see: WO03/051852 pamphlet). It cannot be expected by a person skilled in the art, however, to increase the optical purity of a material using an optically inactive amine as shown in the present invention, that is, to increase the optical purity of a 2-propyloctanoic acid containing preferentially an R-isomer, i.e., (2R)-2-propyloctanoic acid, up to 99.5% e.e. or more by preferential crystallization with an optically inactive amine.

Moreover, as shown in Example below, the effect of improving the optical purity of (2R)-2-propyloctanoic acid of 95.0% e.e. was examined with (R)-(+)-1-phenylethylamine and dibenzylamine for comparison; as a result, it was found that (R)-(+)-1-phenylethylamine required 7 times recrystallization to give (2R)-2-propyloctanoic acid with the optical purity of 99.5% e.e., but dibenzylamine required only twice recrystallization. Further, in comparison of their total yield, (R)-(+)-1-phenylethylamine gives the product in 40% yield, and on the other hand, dibenzylamine does in 61% yield.

That is, though dibenzylamine is an optically inactive amine, it can work to enhance the optical purity of (2R)-2-propyloctanoic acid, and the effect of improving the optical purity is excellent in both of yield and efficiency.

Thus, the process for increasing the optical purity of a material using an optically inactive amine can be applied to large scale treatment and is convenient and inexpensive in comparison with the above process using an optically active amine. Thus, this process is industrially excellent.

Application to Pharmaceuticals:

The crystals of the present invention, as they contain a crystal comprising (2R)-2-propyloctanoic acid as an active ingredient and an amine, are useful in prevention, treatment and/or suppression of, for example, neurodegenerative disease, neuropathy, or disease in need of nerve regeneration, or their progress, in a mammal (for example, human, non-human animal, e.g., monkey, sheep, bovine, equine, dog, cat, rabbit, rat, mouse, etc.).

The term neurodegenerative disease includes all of diseases accompanied by degeneration of nerve cell, and is not limited by its cause. The neurodegenerative disease in the present invention also includes neuropathy or disease in need of nerve regeneration. The nerve cell may be any type of nerve cells in the living body, including, for example, central nerves (e.g., cerebral nerves, spinal nerves, etc.), peripheral nerves (e.g., autonomic nervous system (e.g., sympathetic nerve, parasympathetic nerve, etc.), etc.) and so on. The neurodegenerative disease is, for example, a disease of central nerve, including Parkinson's disease, Parkinson syndrome, Alzheimer's disease, Down's disease, amyotrophic lateral sclerosis, familial amyotrophic lateral sclerosis, progressive supranuclear palsy, Huntington's disease, spinocerebellar ataxia, dentatorubral-pallidoluysian atrophy, olivopontocerebellar atrophy, cortical basal degeneration, familial dementia, frontal temporal dementia, senile dementia, diffuse Lewy body disease, striatonigral degeneration, chorea athetosis, dystonia, Meigs's syndrome, late cortical cerebellar atrophy, familial spastic paraplegia, motor neuron disease, Machado-Joseph disease, Pick's disease, nervous dysfunction after cerebral apoplexy (for example, brain hemorrhage (e.g., hypertensive intracerebral bleeding, etc.), cerebral infarction (e.g., cerebral thrombosis, cerebral embolus, etc.), transient ischemic attack, subarachnoid hemorrhage, etc.), nervous dysfunction after spinal damage, demyelinating disease (for example, multiple sclerosis, Guillain-Barre syndrome, acute disseminated encephalomyelitis, acute cerebellitis, transverse myelitis, etc.), brain tumor (for example, astrocytoma, etc.), cerebrospinal disease caused by infection (for example, meningitis, cerebral abscess, Creutzfeldt-Jakob disease, AIDS dementia, etc.), mental disease (schizophrenia, manic-depressive psychosis, neurosis, psychosomatic disease, epilepsy, etc.) and the like. The neurodegenerative disease is more preferably Parkinson's disease, Parkinson syndrome, Alzheimer's disease, amyotrophic lateral sclerosis, familial amyotrophic lateral sclerosis, or the like.

The neuropathy includes all of the nervous dysfunction. That is, the neuropathy generally includes disorders recognized as a symptom during disease. For example, Parkinson's disease or Parkinson syndrome is accompanied by for example tremor, myospasm (rigidity), bradypragia, postural disturbance, dysautonomia, pulsion phenomenon, gait disorder, mental symptom, and so on. For example, Alzheimer disease is accompanied by dementia symptom; the amyotrophic lateral sclerosis or familial amyotrophic lateral sclerosis is accompanied by muscle atrophy, muscle weakness, dysfunction of upper extremity, gait disorder, dysarthria, dysphagia, respiration disorder, and so on.

The disease in need of nerve regeneration is means those in which the absolute number of the neurocytes are reduced by lack of neurocytes to spoil normal neural function, including, for example, the above neurodegenerative disease in such a state. In such a disease, a cell capable of generating normal nerves (for example, nerve stem cell, nerve precursor cell, nerve cell, other stem cell, glia cell, etc.) is transplanted surgically or an intrinsic cell of them is activated to regenerate the nerve for therapy. The crystal of the present invention may be administered temporarily or continuously at the time of transplantation of the above cell or of activation of the intrinsic cell to accelerate nerve regeneration.

Further, the crystal of the present invention is also useful as a nerve regeneration accelerator or S100β-increase inhibitor. The crystal of the present invention may be formulated into the above pharmaceutical preparations for administration to the living body with the aim of prevention, treatment and/or suppression of progress of the above-mentioned diseases. In the present invention, the term "prevention" means to prevent the onset of disease itself; "treatment" means to lead the state of disease to cure; and "suppression of progress" means to suppress the deterioration or stop the progress of the state.

The dosage depends on age, body weight, condition, therapeutic effect, method of administration, time of treatment, and so on, though it may be administered orally at a dose of 1 mg to 5000 mg for an adult once or several times a day, or parenterally (preferably intravenously) at a dose of 1 mg to 1200 mg once or several times a day, or infused intravenously continuously for 1 hour to 24 hours a day.

As mentioned above, however, the dosage is variable depending on various conditions, and accordingly the dosage may be lower than or over the above defined dosage in some cases.

In addition, naturally, (2R)-2-propyloctanoic acid with the optical purity over 99.5% e.e. in. the present invention is effective in prevention, treatment and/or suppression of progress of the above diseases. Such (2R)-2-propyloctanoic acid may be formulated into a pharmaceutical preparation as mentioned above; as it has a property of oil, it is preferably formulated into injection or filled in soft capsules, utilizing the characteristics of liquid. For example, in a soft capsule, the dosage may be the same as mentioned above, but a daily dosage is preferably about 50 to about 5000 mg, particularly about 100 to about 1200 mg. The dosage as injection is variable depending on the degree of symptom; age of the subject, gender, body weight; timing of administration, or intervals of administration, and there is no particular limitation; for example, it may be in the same range as mentioned above, or it may be intravenously injected as infusion, for example, as an agent for neurodegenerative disease such as cerebral infaction at a daily dose of about 2 to about 12 mg per kg body weight of a patient. More preferably, it may be administered at a daily dose of about 2 mg, about 4 mg, about 6 mg, about 8 mg, about 10 mg, or about 12 mg per kg body weight of a patient. Even more preferably, it may be administered at a daily dose of about 4 mg, about 6 mg, about 8 mg, or about 10 mg per kg body weight of a patient. Particularly, the daily dose is about 4 mg or about 8 mg per kg body weight of a patient.

The pharmaceutical composition containing the crystal of the present invention or (2R)-2-propyloctanoic acid having an optical purity of more than 99.5% e.e. as active ingredient may be also combined with, for example, an anticonvulsant (e.g., phenobarbital, mephobarbital, metharbital, primidone, phenyloin, ethotoin, trimethadione, ethosuximide, acetylphenetride, carbamazepine, acetazolamide, diazepam, sodium valproate, etc.), an acetylcholinesterase inhibitor (e.g., donepezil hydrochloride, TAK-147, rivastigmine, galantamine, etc.), a neurotrophic factor (e.g., ABS-205, etc.), an aldose reductase inhibitor, an antithrombotic (e.g., t-PA, heparin), an oral anticoagulant (e.g., warfarin, etc.), a synthetic antithrombin drug (e.g., gabexate mesylate, nafamostat mesylate, argatroban, etc.), an antiplatelet drug (e.g., aspirin, dipyridamole, ticlopidine hydrochloride, beraprost sodium, cilostazol, sodium ozagrel, etc.), a thrombolytic agent (e.g., urokinase, tisokinase, alteprase, etc.), a Factor Xa inhibitor, a Factor VIIa inhibitor, a cerebral blood flow and metabolism improver (e.g., idebenone, calcium hopantenate, amantadine hydrochloride, meclofenoxate hydrochloride, dihydroergotoxine mesylate, pyrithioxin hydrochloride, γ-aminobutyric acid, bifemelane hydrochloride, lisuride maleate, indeloxazine hydrochloride, nicergoline, propentofylline, etc.), an antioxidant (e.g., edaravone, etc.), a glycerin preparation (e.g., glyceol, etc.), a β-secretase inhibitor (e.g., 6-(4-biphenylyl)methoxy-2-[2-(N,N-dimethylamino)ethyl]tetraline, 6-(4-biphenylyl)methoxy-2-(N,N-dimethylamino)methyltetraline, 6-(4-biphenylyl)methoxy-2-(N,N-dipropylamino) methyltetraline, 2-(N,N-dimethylamino)methyl-6-(4'-methoxybiphenyl-4-yl)methoxytetraline, 6-(4-biphenylyl) methoxy-2-[2-(N,N-diethylamino)ethyl]tetraline, 2-[2-(N,N-dimethylamino)ethyl]-6-(4'-methylbiphenyl-4-yl) methoxytetraline, 2-[2-(N,N-dimethylamino)ethyl]-6-(4'-methoxybiphenyl-4-yl)methoxytetraline, 6-(2',4'-dimethoxybiphenyl-4-yl)methoxy-2-[2-(N,N-dimethylamino)ethyl]tetraline, 6-[4-(1,3-benzodioxol-5-yl) phenyl]methoxy-2-[2-(N,N-dimethylamino)ethyl]tetraline, 6-(3',4'-dimethoxybiphenyl-4-yl)methoxy-2-[2-(N,N-dimethylamino)ethyl]tetraline, and optical isomers, salts and hydrates thereof, OM99-2 (WO 01/00663), etc.), β-amyloid protein aggregation inhibitor (e.g., PTI-00703, ALZHEMED (NC-531), PPI-368 (JP-T-11-514333), PPI-558 (JP-T-2001-500852), SKF-74652 (*Biochem. J*, 340(1), 283-289 (1999)), etc.), a cerebral function activator (e.g., aniracetam, nicergoline, etc.), a dopamine receptor agonist (e.g., L-dopa, bromocriptine, pergolide, talipexole, pramipexole, cabergoline, amantadine, etc.), a monoamine oxidase (MAO) inhibitor (e.g., safrazine, deprenyl, selegiline, ramacemide, riluzole, etc.), an anticholinergic drug (e.g., trihexyphenidyl, biperiden, etc.), a COMT inhibitor (e.g., entacapone, etc.), a therapeutic agent for amyotrophic lateral sclerosis (e.g., riluzole, a neurotrophic factor, etc.), a statin-based therapeutic agent for hyperlipidemia (e.g., sodium pravastatin, atorvastatin, simvastatin, rosuvastatin, etc.), a fibrate-based therapeutic agent for hyperlipidemia (e.g., clofibrate, etc.), an apoptosis inhibitor (e.g., CPI-1189, IDN-6556, CEP-1347, etc.), a nerve differentiation and regeneration promoter (e.g., leteprinim, xaliproden (SR-57746-A), SB-216763, etc.), a nonsteroidal anti-inflammatory drug (e.g., meloxicam, tenoxicam, indomethacin, ibuprofen, celecoxib, rofecoxib, aspirin, indomethacin, etc.), a steroid drug (e.g., dexamethasone, hexestrol, cortisone acetate, etc.), a sexual hormone or derivatives thereof (e.g., progesterone, estradiol, estradiol benzoate, etc.), or the like. Furthermore, it may be also combined with a nicotinic receptor regulator, a γ-secretase inhibitor, a β-amyloid vaccine, a β-amyloid protease, a squalene synthetase inhibiting agent, a therapeutic agent for the abnormal behavior, wandering or the like associated with progress of dementia, a hypotensor, a therapeutic agent for diabetes mellitus, an antidepressant, an antianxiety agent, a disease-modifying antirheumatoid agent, an anticytokine agent (e.g., a TNF inhibitor, a MAP kinase inhibitor, etc.), a parathyroid hormone (PTH), a calcium receptor antagonist or the like.

These combination medicaments are only exemplary and are not limited to these.

Other medicaments may be administered in any combination of two or more. Furthermore, the medicaments for combined use include those that have been discovered as well as those that are to be discovered afterward, based on the mechanism described above.

Pharmacological Activity:

It can be confirmed by a known method, for example, a method described in the specification of EP Patent 0632008, EP-A-1174131 or the like that the crystal of the present invention has high pharmacological activity similar to (2R)-2-propyloctanoic acid.

Toxicity:

Toxicity of (2R)-2-propyloctanoic acid or a salt thereof is very low, and it is considered to be sufficiently safe for the use as a pharmaceutical drug.

Effect of the Invention:

According to the present invention, crystals comprising (2R)-2-propyloctanoic acid and an amine, which can be used as bulk drugs for safely orally administrable solid preparations with keeping the pharmacological effect, are provided. Among these crystals, the crystal with dibenzylamine per se is particularly useful not only as bulk drug for pharmaceuticals but also as an intermediate to produce (2R)-2-propyloctanoic acid having a remarkably high optical purity of more than 99.5% e.e.

Best Mode For Carrying Out The Invention

Hereinafter, the present invention will be explained in detail by way of Examples, which are not intended as a limitation thereof. They may be changed within the scope of the present invention as far as they do not departure from the scope of the present invention.

REFERENCE EXAMPLE 1

(1S)-1-Propylheptyl 4-methylbenzenesulfonate

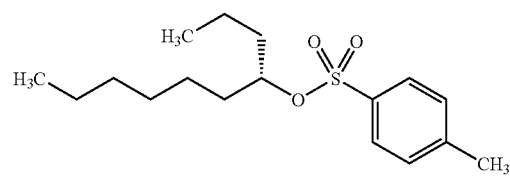

Under an argon atmosphere, cuprous chloride (4.6 g) was added to a solution of (2R)-2-hexyloxirane (300 g) in tetrahydrofuran (642 mL), and then ethylmagnesium chloride tetrahydrofuran solution (2.1 mol/L, 1309 g) was added dropwise at −40 to −20° C. (inner temperature). The reaction mixture was stirred at −30 to −20° C. (inner temperature) for about 30 minutes, and then tosyl chloride (491 g) was added, and the mixture was stirred at 0-20° C. (inner temperature) for about 4 hours. To the reaction mixture was then added 10 v/v % sulfuric acid (conc. sulfuric acid:water=65 mL:650 mL), aqueous sodium chloride (13.6 g) solution (272 mL) and ethyl acetate (1.5 L) for extraction. The resulting organic layer was washed with (1) a solution of sodium chloride (32 g) in water (636 mL), (2) a mixture of a solution of potassium carbonate (73 g) in water (730 mg) and a saturated brine (200 mL), and (3) a saturated brine (600 mL) in order, and then concentrated to give the title compound (758.7 g; yield 89%).

TLC: Rf 0.44 (hexane:ethyl acetate=10:1);

NMR (CDCl$_3$): δ 0.83 (t, J=7.3 Hz, 3H), 0.85 (t, J=7.1 Hz, 3H), 1.24 (m, 10H), 1.56 (m, 4H), 2.44 (s, 3H), 4.56 (m, 1H), 7.32 (d, J=8.1 Hz, 2H), 7.79 (d, J=8.1 Hz, 2H).

REFERENCE EXAMPLE 2

(2R)-2-propyloctanenitrile

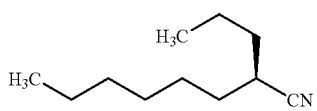

Under an argon atmosphere, 1,3-dimethyl-2-imidazolidinone (624 mL) and acetone cyanohydrin (394 g) were added to a solution of the compound (758.7 g) produced in Reference Example 1 in tetrahydrofuran (1458 mL), and additionally lithium hydroxide (96.8 g) was added at room temperature, and the mixture was stirred at 50-55° C. (inner temperature) for about 14 hours. A solution of sodium chloride (400 g) in water (2.2 L) was added to the reaction mixture and extracted with a mixture of n-hexane and ethyl acetate (2:1) (1660 mL). The resulting organic layer was washed with a solution of sodium chloride (150 g) in water (830 mL) and concentrated. The residue was purified by distillation to give the title compound having the following physicochemical properties (335 g [92.1 area %], 97.1% e.e.; 89% yield).

The optical purity of the title compound was determined by gas chromatography.

TLC: Rf 0.54 (hexane:ethyl acetate=10:1);
NMR (CDCl$_3$): δ 0.89 (t, J=6.59 Hz, 3H), 0.95 (t, J=7.05 Hz, 3H), 1.46 (m, 14H), 2.52 (m, 1H).

REFERENCE EXAMPLE 3

(2R)-2-propyloctanamide

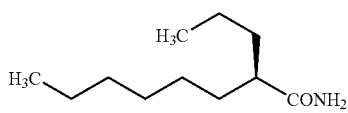

Under an argon atmosphere, dimethylsulfoxide (177 g) and potassium carbonate (16.5 g) were added to a solution of the compound (122 g [82.0 area %], 96.2% e.e.) produced in the same manner as in Reference Example 2, and 35% hydrogen peroxide (8.7 g) was added dropwise thereto at 50-70° C. (inner temperature), followed by stirring for about 1 hour. A solution of sulfurous acid (9.3 g) in water (720 mL) was added to the reaction mixture, cooled to about 10° C. (inner temperature) and stirred for 30 minutes. The reaction mixture was filtered, washed with an acetonitrile:water (1:2) mixture (435 mL) and with water (632 mL) to give crude crystals of the title compound (133 g [84.3 area %], 96.5% e.e., moisture content 15 w/w %). To the crude crystals (40 g) was added acetonitrile (240 mL) and water (160 mL), and the mixture was warmed up at 56-60° C. (inner temperature) to dissolve the crude crystals. The solution was cooled down to about 29° C. (inner temperature) at a cooling rate of 10-15° C./60 minutes, and after addition of water (80 mL) down to 15° C.-16° C. at a cooling rate of 10-15° C./60 minutes. The reaction mixture was stirred at this temperature for about 30 minutes, filtered, and washed with a acetonitril:water (1:2) mixture (80 mL) to give the crystals of the title compound having the following physicochemical properties (30.8 g [97.8 area %], 99.7% e.e., moisture content 11.6 w/w %).

The optical purity of the title compound was determined by liquid chromatography.

TLC: Rf 0.24 (hexane:ethyl acetate=1:1);
NMR (CDCl$_3$): δ 0.89 (m, 6H), 1.34 (m, 12H), 1.58 (m, 2H), 2.11 (m, 1H), 5.40 (brs., 1H), 5.51 (brs., 1H);
IR (KBr method): 3373, 3181, 2954, 2928, 2871, 2851, 1657, 1465, 1452, 1424, 1377, 1319, 1298, 1285, 1242, 1230, 1214, 1192, 1148, 1136, 1106, 987, 899, 830, 784, 762, 743, 729, 683, 627 cm$^{-1}$.

REFERENCE EXAMPLE 4

(2R)-2-propyloctanoic acid

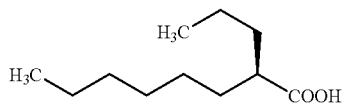

Under an argon atmosphere, the compound (100 g) produced in Reference Example 3 was dissolved in acetic acid (230 mL) at about 40° C. (inner temperature). A solution of methanesulfonic acid (130 g) in water (182 mL) was added to the above solution, then stirred at about 105-112° C. (inner temperature) for about 13 hours, and cooled to about 28° C. (inner temperature). Then, water (400 mL) and a mixture of n-heptane: isopropyl acetate (5:1) (500 mL) were added and the mixture was extracted. The organic layer was washed twice with water (400 mL) and concentrated to give (2R)-2-propyloctanoic acid having the following physicochemical properties (103 g, 99.3% e.e.).

The optical purity was determined by liquid chromatography after conversion into the phenacyl ester.

TLC: Rf 0.54 (hexane:ethyl acetate=7:3);
NMR (CDCl$_3$): δ 0.86-0.93 (m, 6H), 1.25-1.50 (m, 2H), 2.36 (m, 1H).

EXAMPLE 1

Crystal comprising (2R)-2-propyloctanoic acid and dibenzylamine

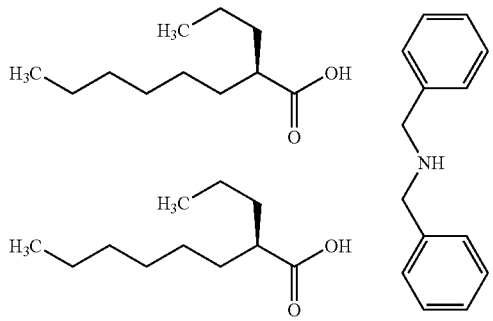

To (2R)-2-propyloctanoic acid (103 g) produced in Reference Example 4 was added acetonitrile (1.5 L) and dibenzylamine (58.6 g), and the mixture was stirred at about 60° C. (inner temperature) for 10-25 minutes, then cooled to 10-20° C. (inner temperature) at a cooling rate of 10° C./60 minutes, then stirred for about 30 minutes, and filtered. The resulting crystals were washed with acetonitrile (200 mL) and dried in vacuo at about 40° C. to give the compound of the present invention having the following physicochemical properties (136 g, 99.8% e.e.; yield 88%). The resulting compound of the present invention was crystals.

The optical purity of the compound of the present invention was determined by liquid chromatography as a phenacyl ester derived from the compound of the present invention through the free form according to the method as shown in Example 2 below.

NMR (CDCl$_3$): δ 0.87 (t, J=6.78 Hz, 6H), 0.91 (t, J=7.23 Hz, 6H), 1.35 (m, 24H), 1.60 (m, 4H), 2.33 (tt, J=8.79, 5.22 Hz, 2H), 3.87 (s, 4H), 7.30 (m, 10H);

Melting point: 79.5-79.7° C.

Figure 2:
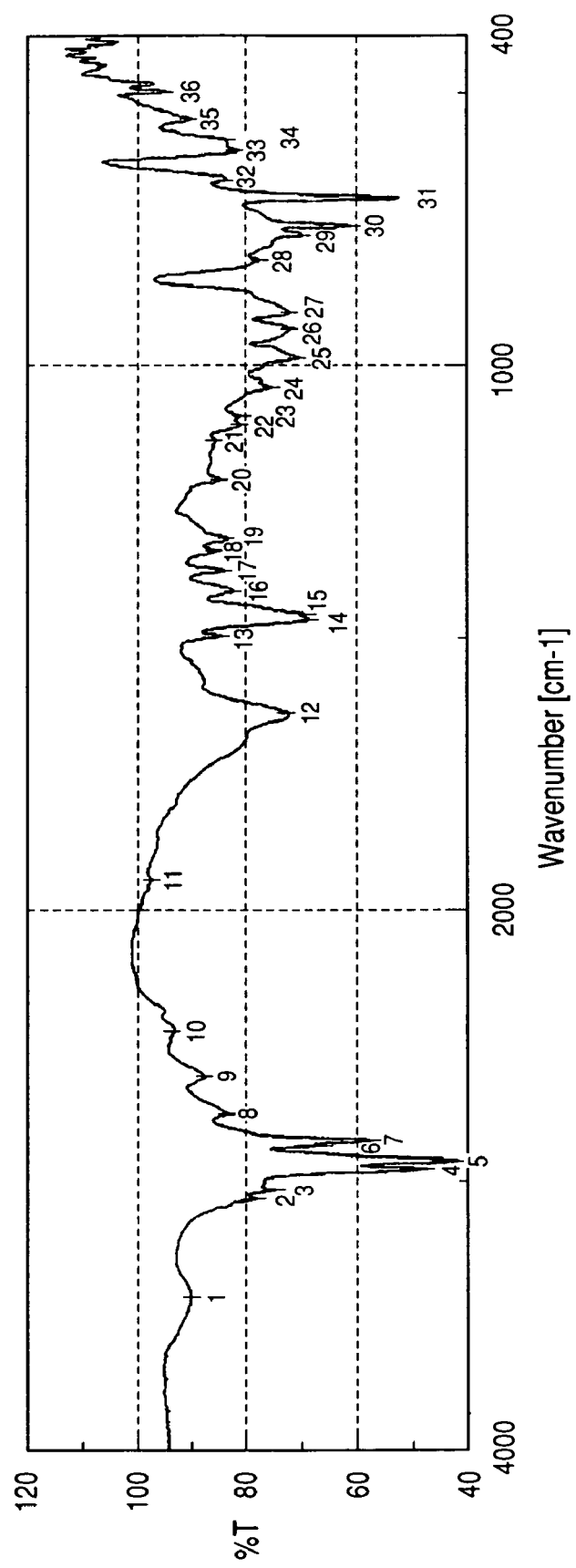
FIG. 2 shows a chart of infrared absorption spectrum (1R) of a crystal comprising (2R)-2-propyloctanoic acid and dibenzylamine.
Figure 3:
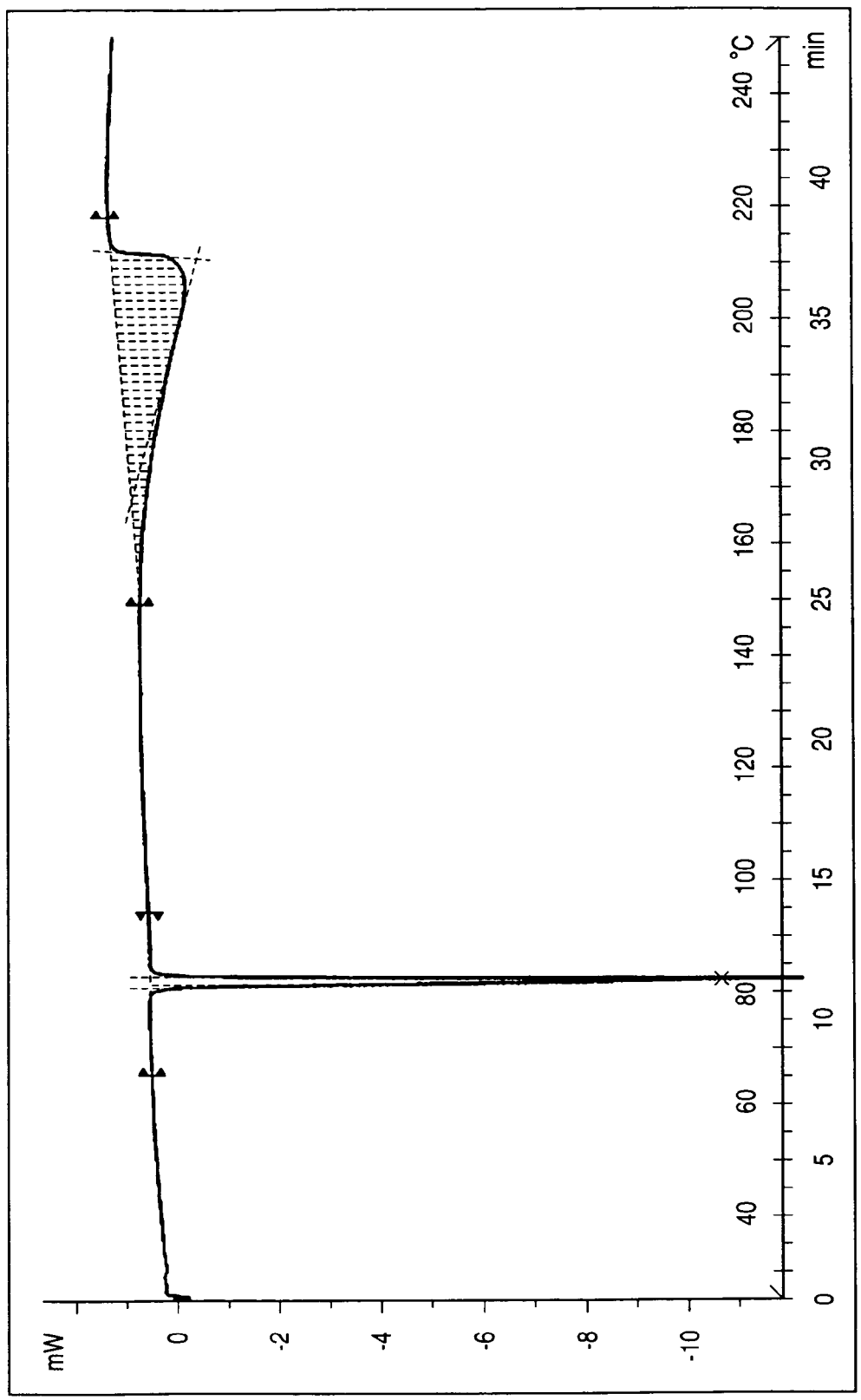
FIG. 3 shows a chart of differential scanning calorimetry (DSC) of a crystal comprising (2R)-2-propyloctanoic acid and dibenzylamine.
Figure 4:
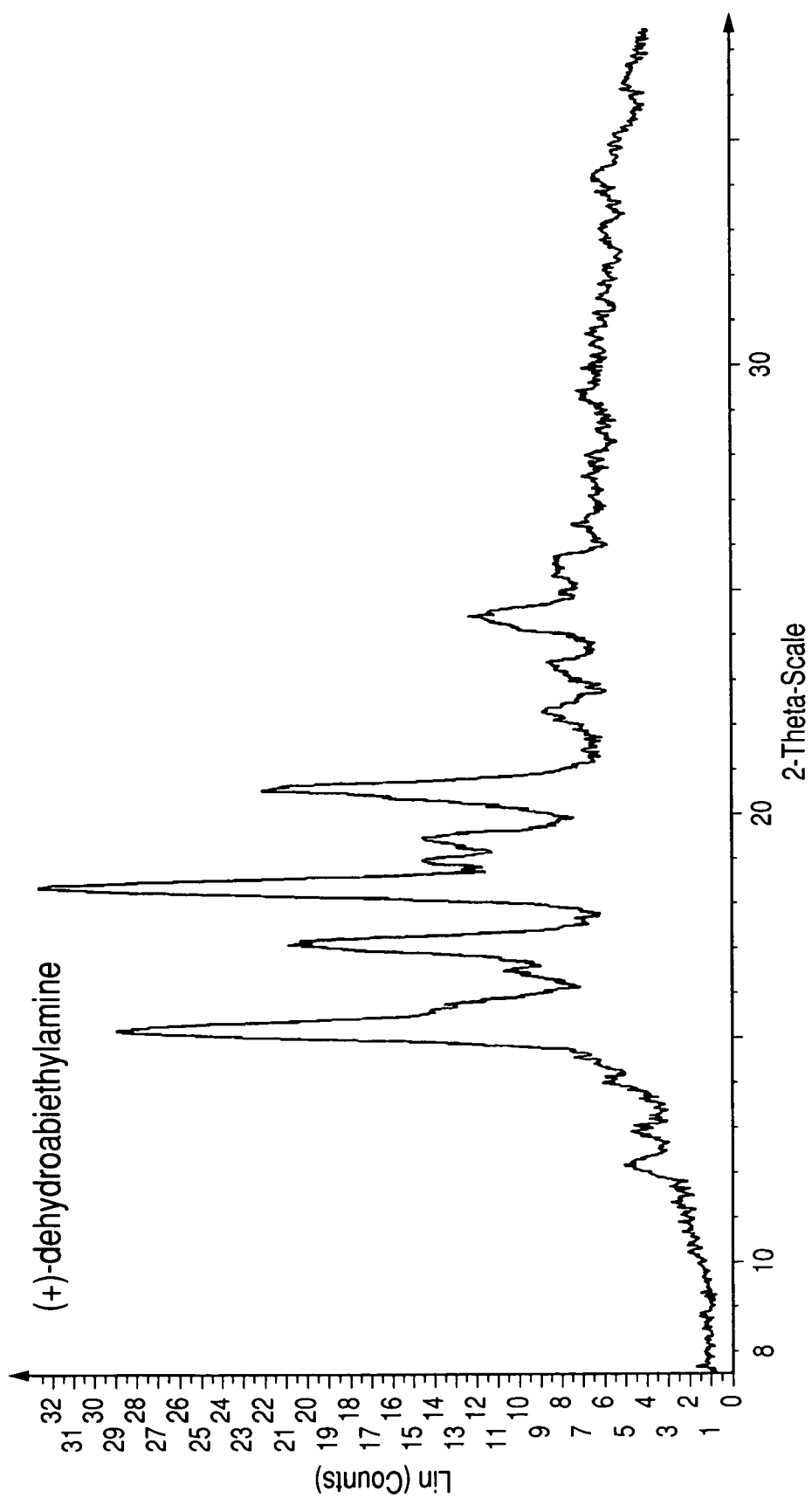
FIG. 4 shows a chart of powdered X-ray diffraction spectrum of a crystal comprising (2R)-2-propyloctanoic acid and (+)-dehydroabietylamine.
Figure 5:
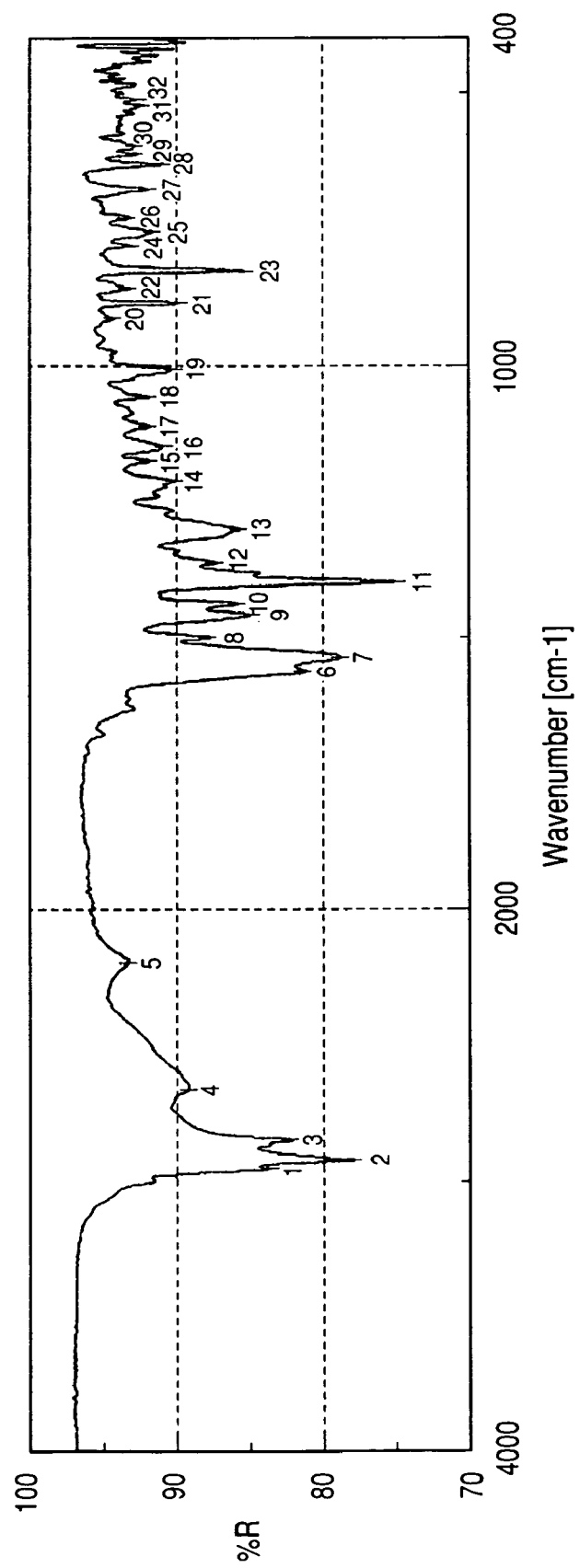
FIG. 5 shows a chart of infrared absorption spectrum (1R) of a crystal comprising (2R)-2-propyloctanoic acid and (+)-dehydroabietylamine.
Figure 6:
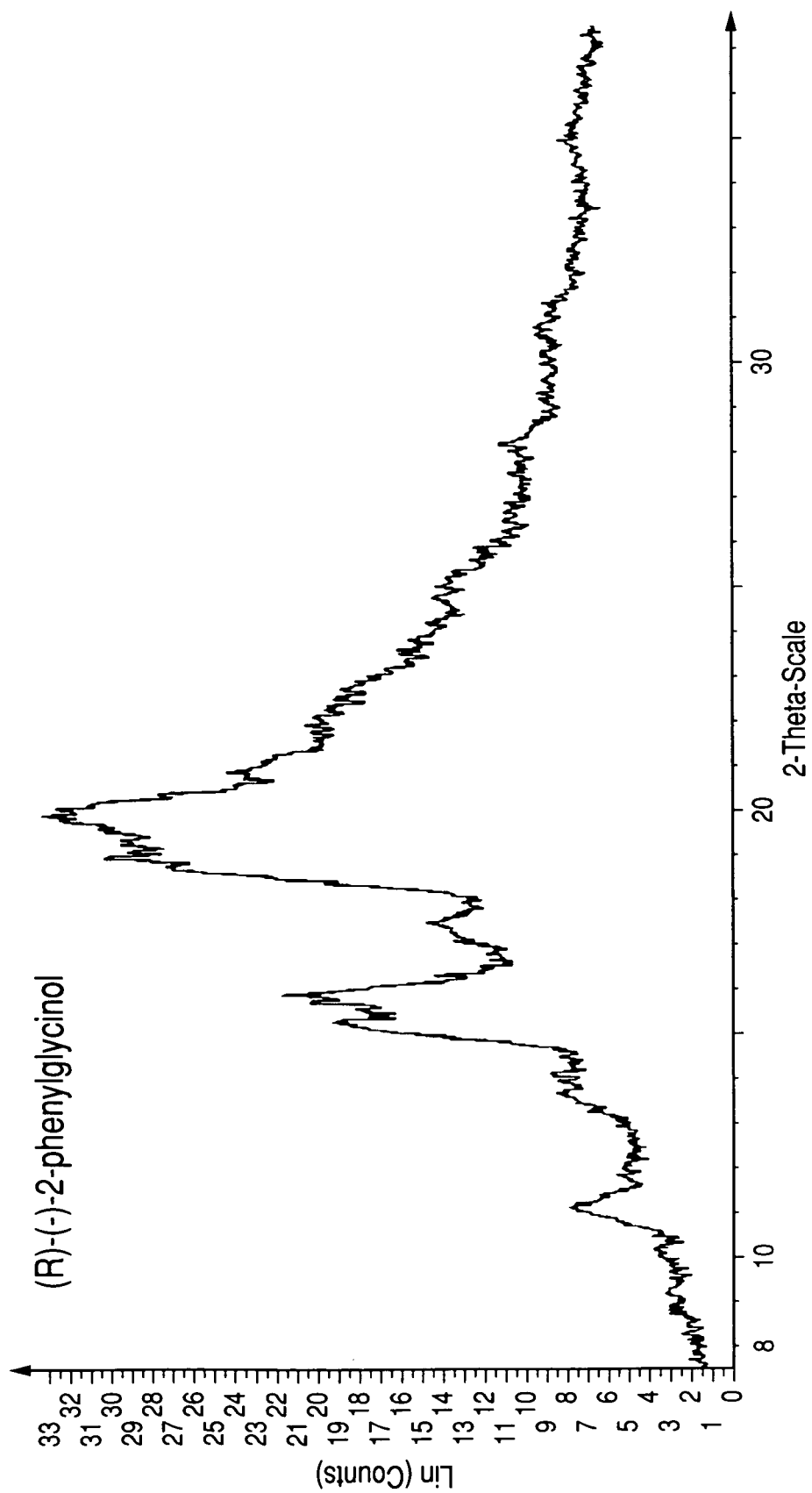
FIG. 6 shows a chart of powdered X-ray diffraction spectrum of a crystal comprising (2R)-2-propyloctanoic acid and (R)-(−)-2-phenylglycinol.
Figure 7:
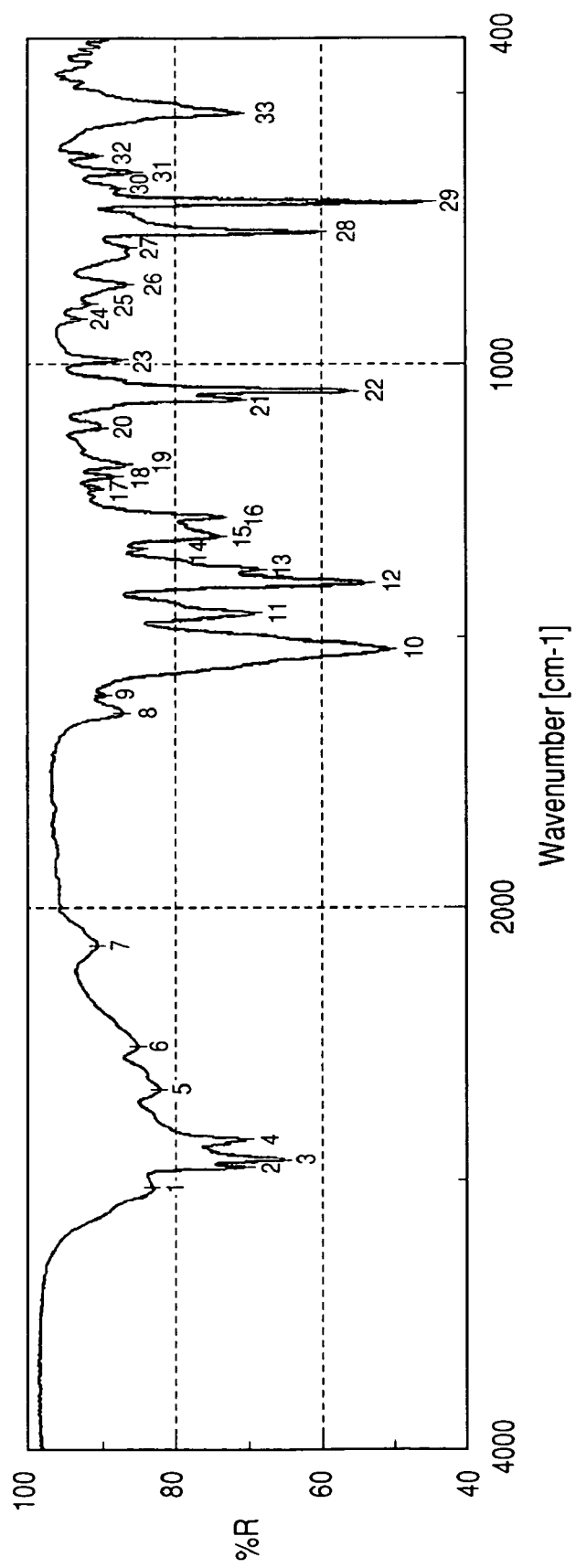
FIG. 7 shows a chart of infrared absorption spectrum (1R) of a crystal comprising (2R)-2-propyloctanoic acid and (R)-(−)-2-phenylglycinol.
Figure 8:
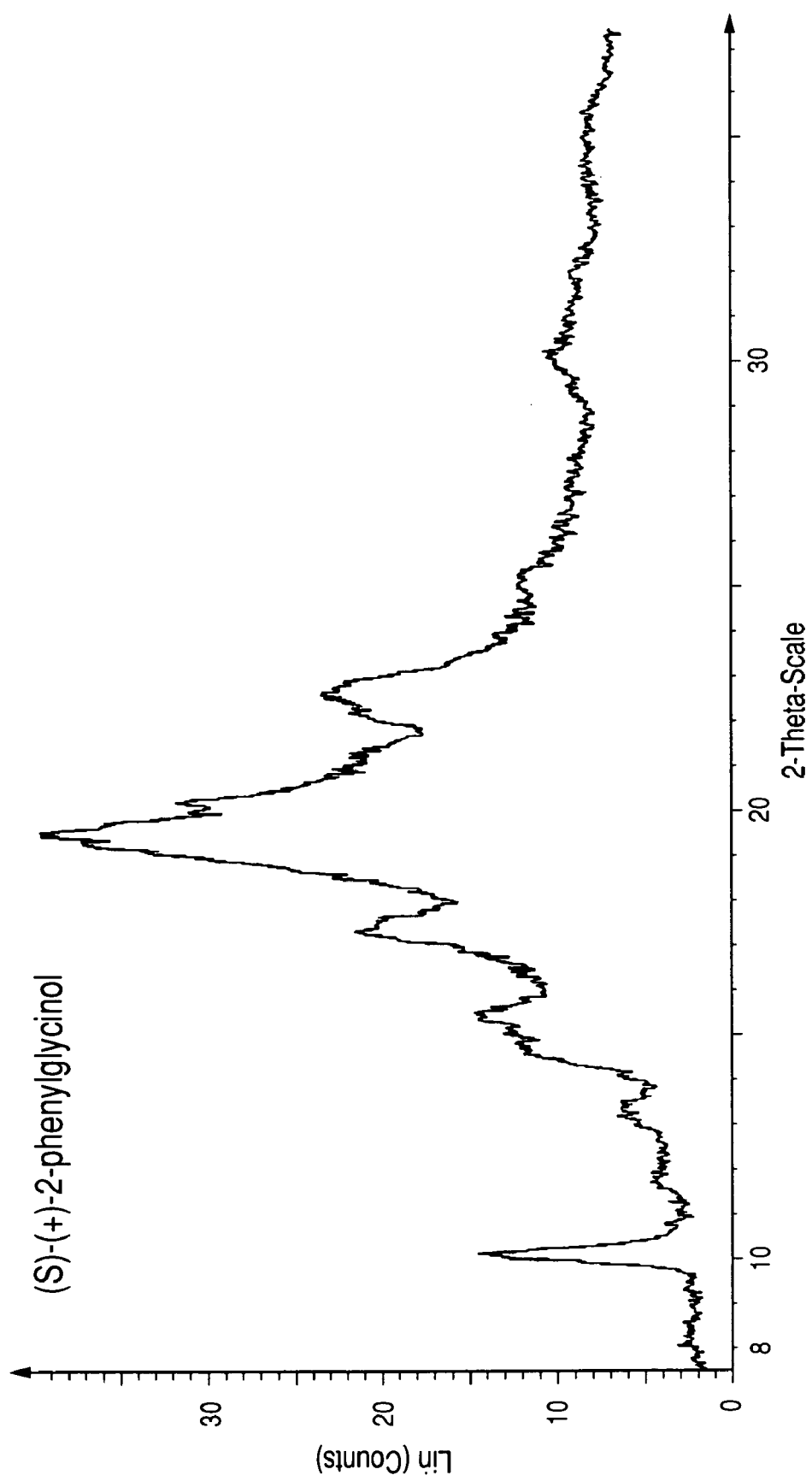
FIG. 8 shows a chart of powdered X-ray diffraction spectrum of a crystal comprising (2R)-2-propyloctanoic acid and (S)-(+)-2-phenylglycinol.
Figure 9:
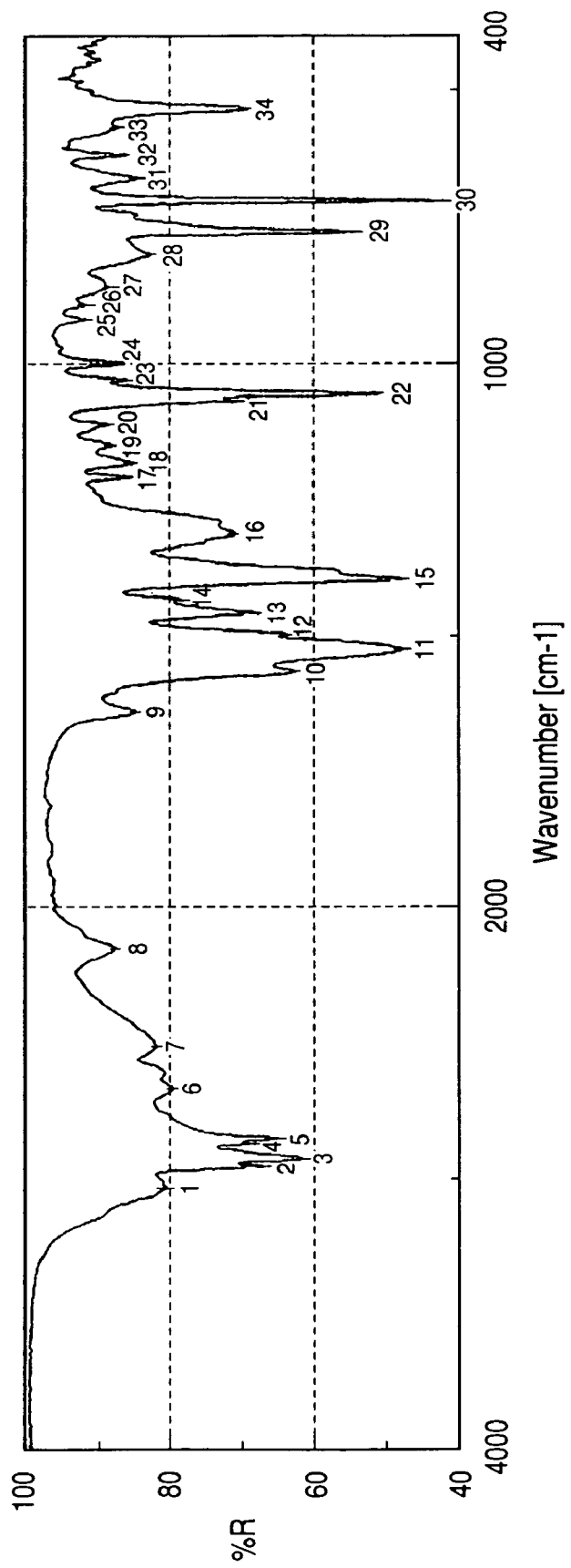
FIG. 9 shows a chart of infrared absorption spectrum (1R) of a crystal comprising (2R)-2-propyloctanoic acid and (S)-(+)-2-phenylglycinol.
Figure 10:
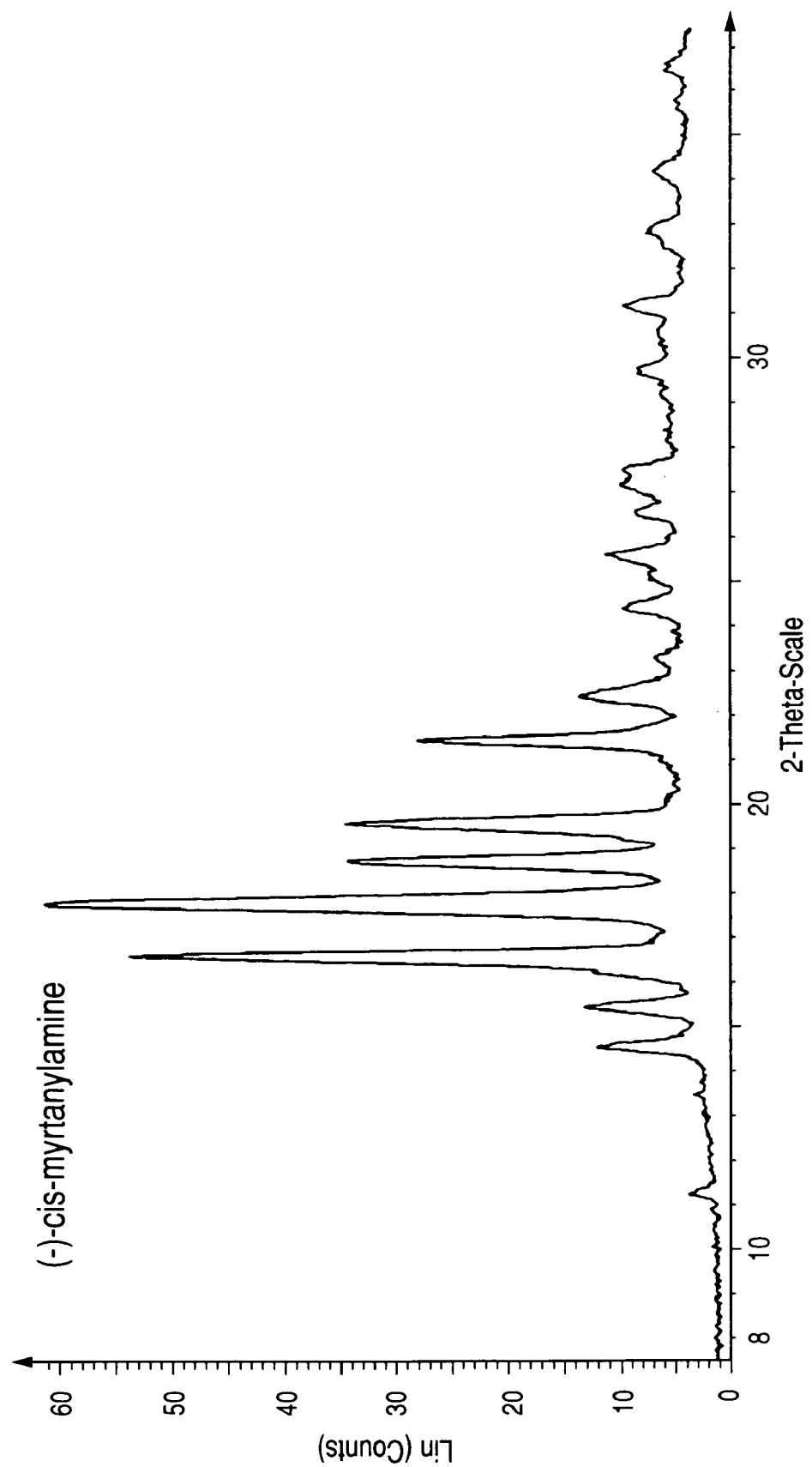
FIG. 10 shows a chart of powdered X-ray diffraction spectrum of a crystal comprising (2R)-2-propyloctanoic acid and (−)-cis-myrtanylamine.
Figure 11:
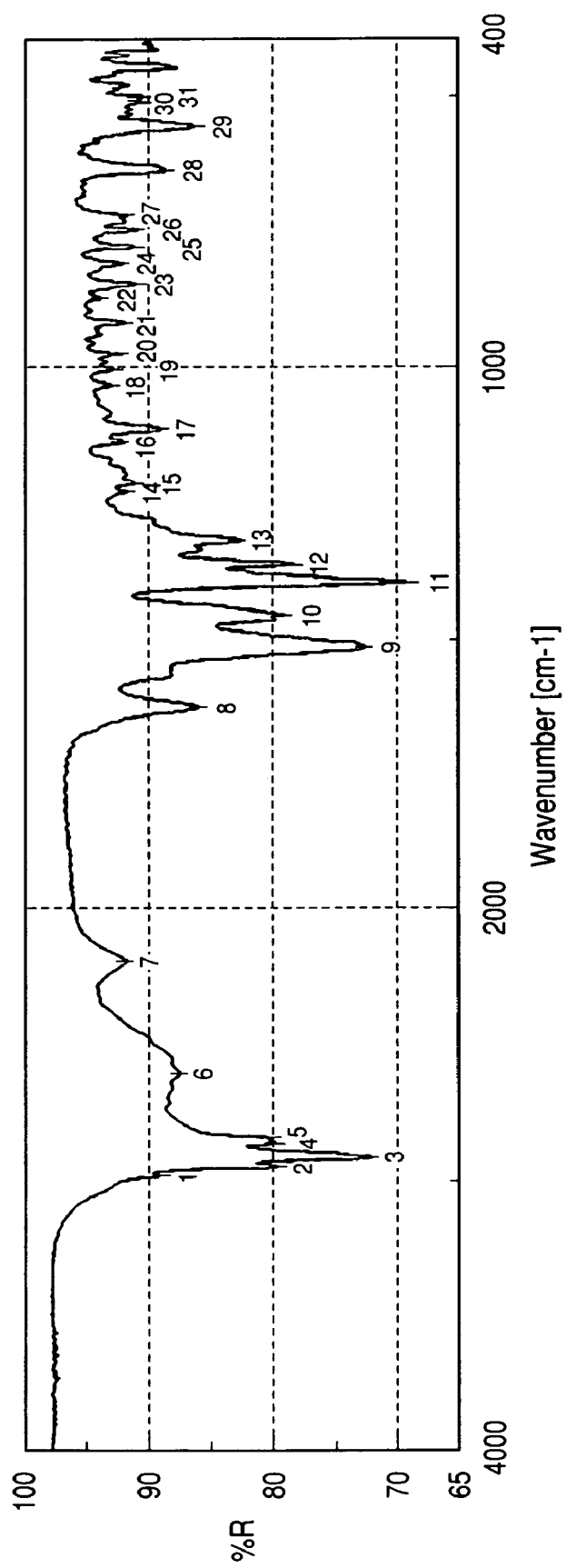
FIG. 11 shows a chart of infrared absorption spectrum (1R) of a crystal comprising (2R)-2-propyloctanoic acid and (−)-cis-myrtanylamine.
Figure 12:
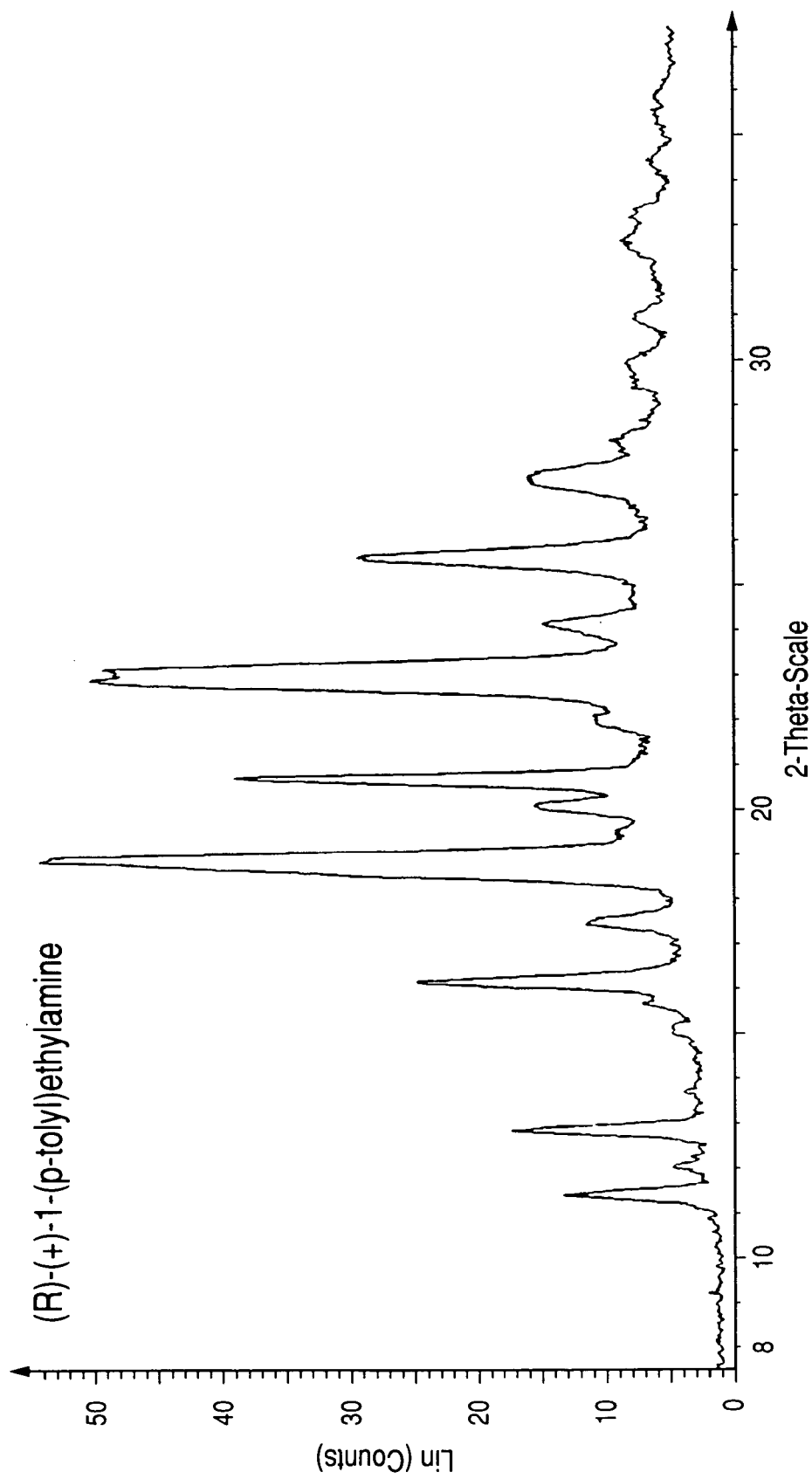
FIG. 12 shows a chart of powdered X-ray diffraction spectrum of a crystal comprising (2R)-2-propyloctanoic acid and (R)-(+)-1-(p-tolyl)ethylamine.
Figure 13:
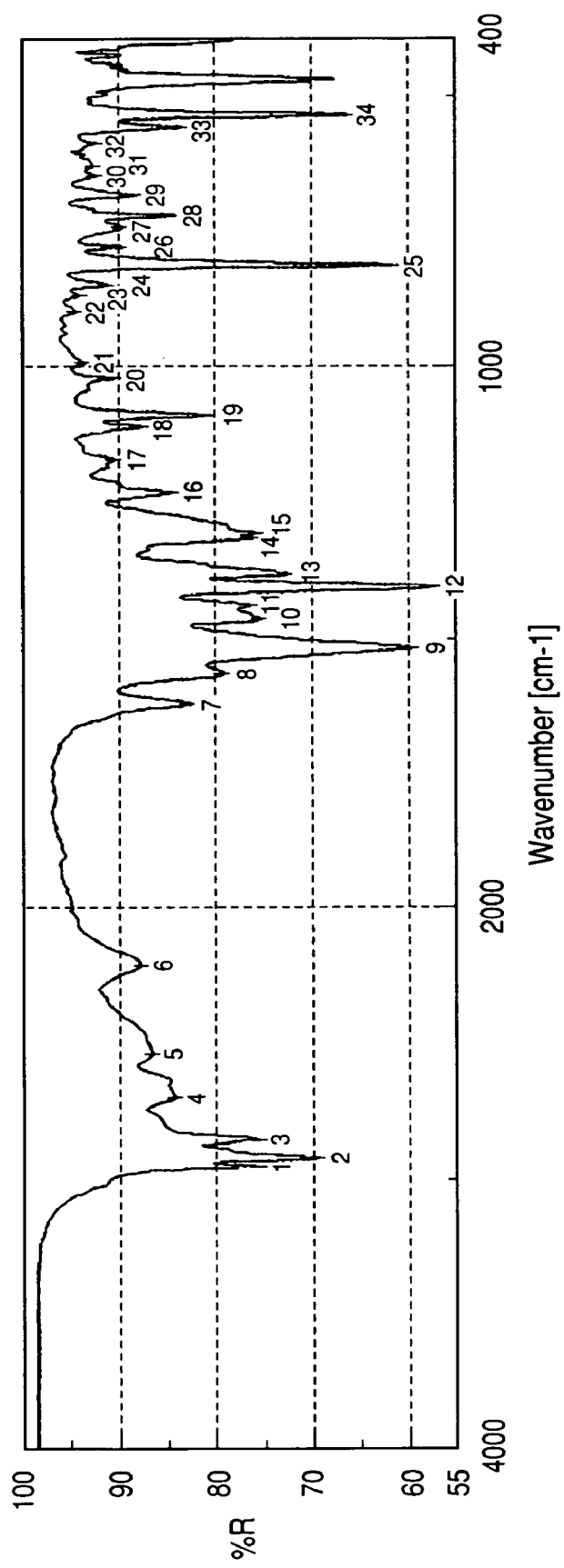
FIG. 13 shows a chart of infrared absorption spectrum (1R) of a crystal comprising (2R)-2-propyloctanoic acid and (R)-(+)-1-(p-tolyl)ethylamine.
Figure 14:
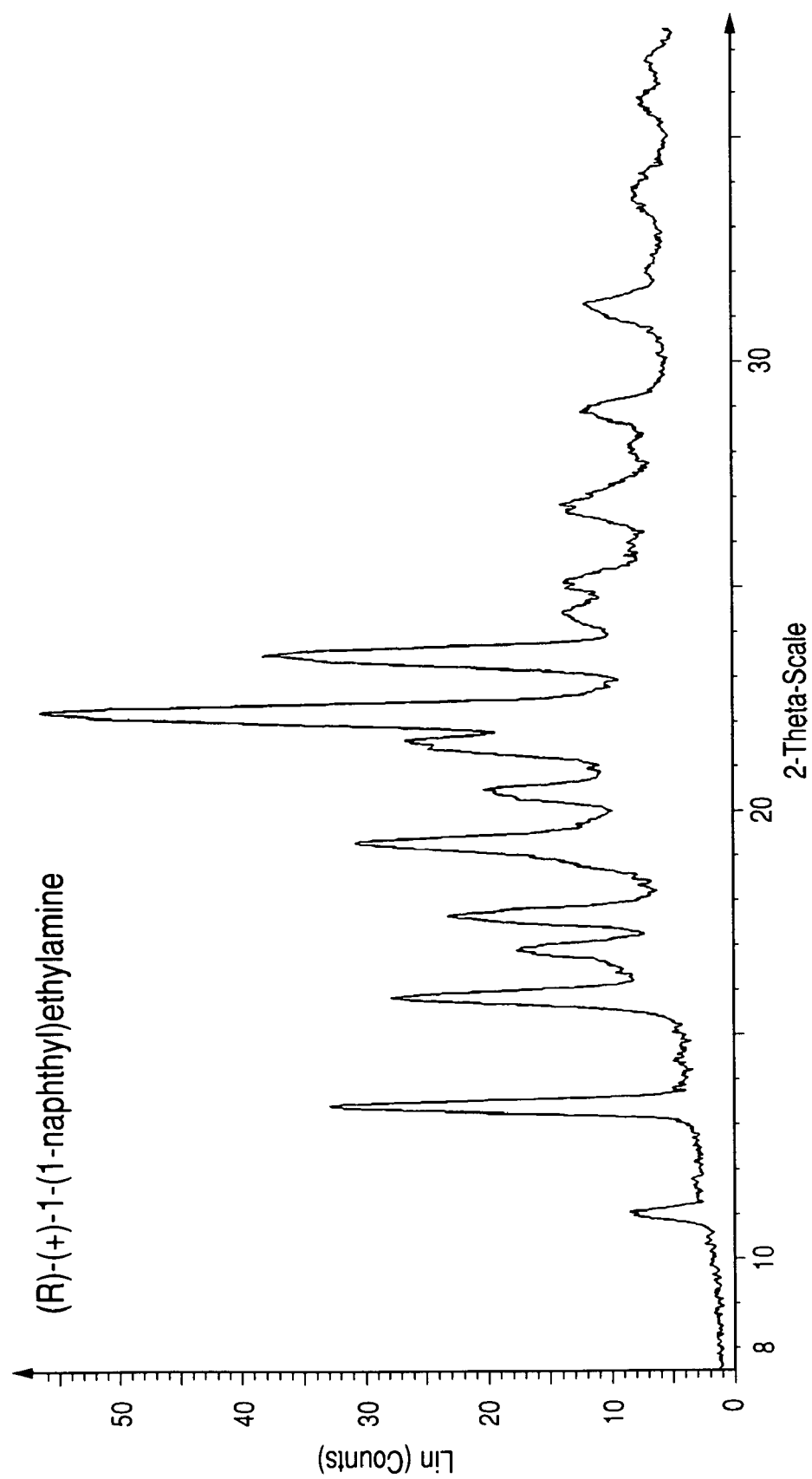
FIG. 14 shows a chart of powdered X-ray diffraction spectrum of a crystal comprising (2R)-2-propyloctanoic acid and (R)-(+)-1-(1-naphthyl)ethylamine.
Figure 15:
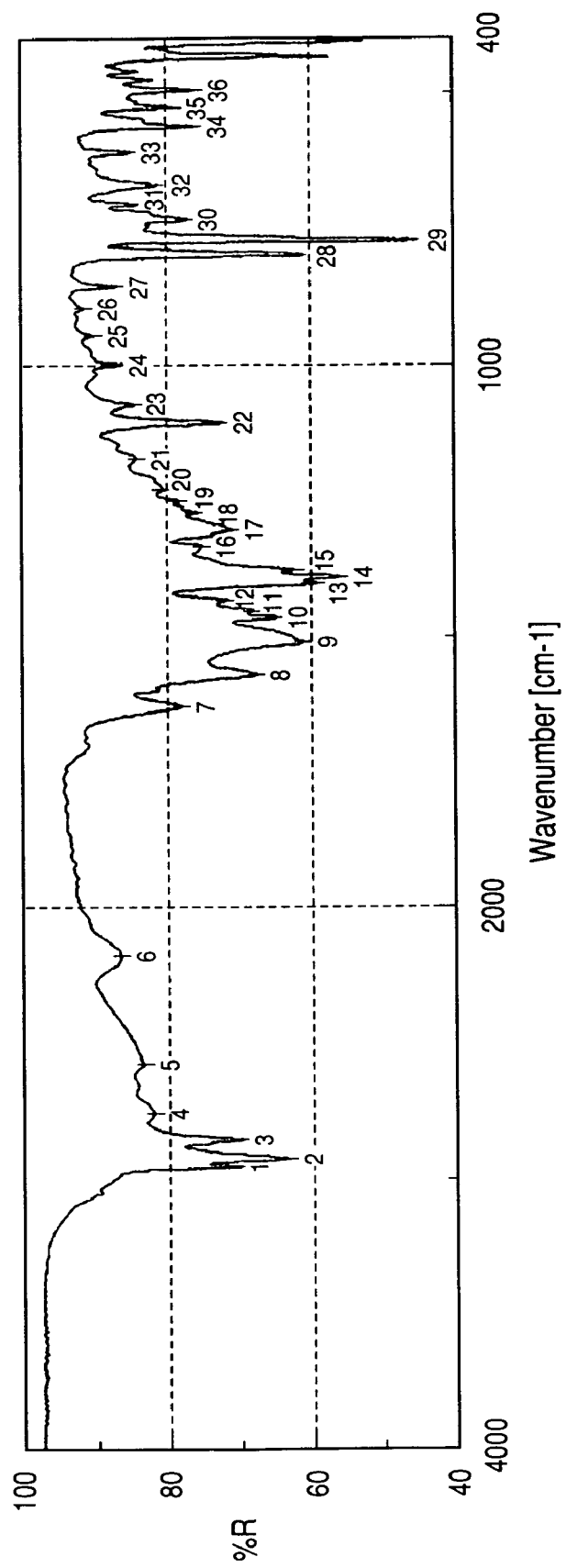
FIG. 15 shows a chart of infrared absorption spectrum (IR) of a crystal comprising (2R)-2-propyloctanoic acid and (R)-(+)-1-(1-naphthyl)ethylamine.
Figure 16:
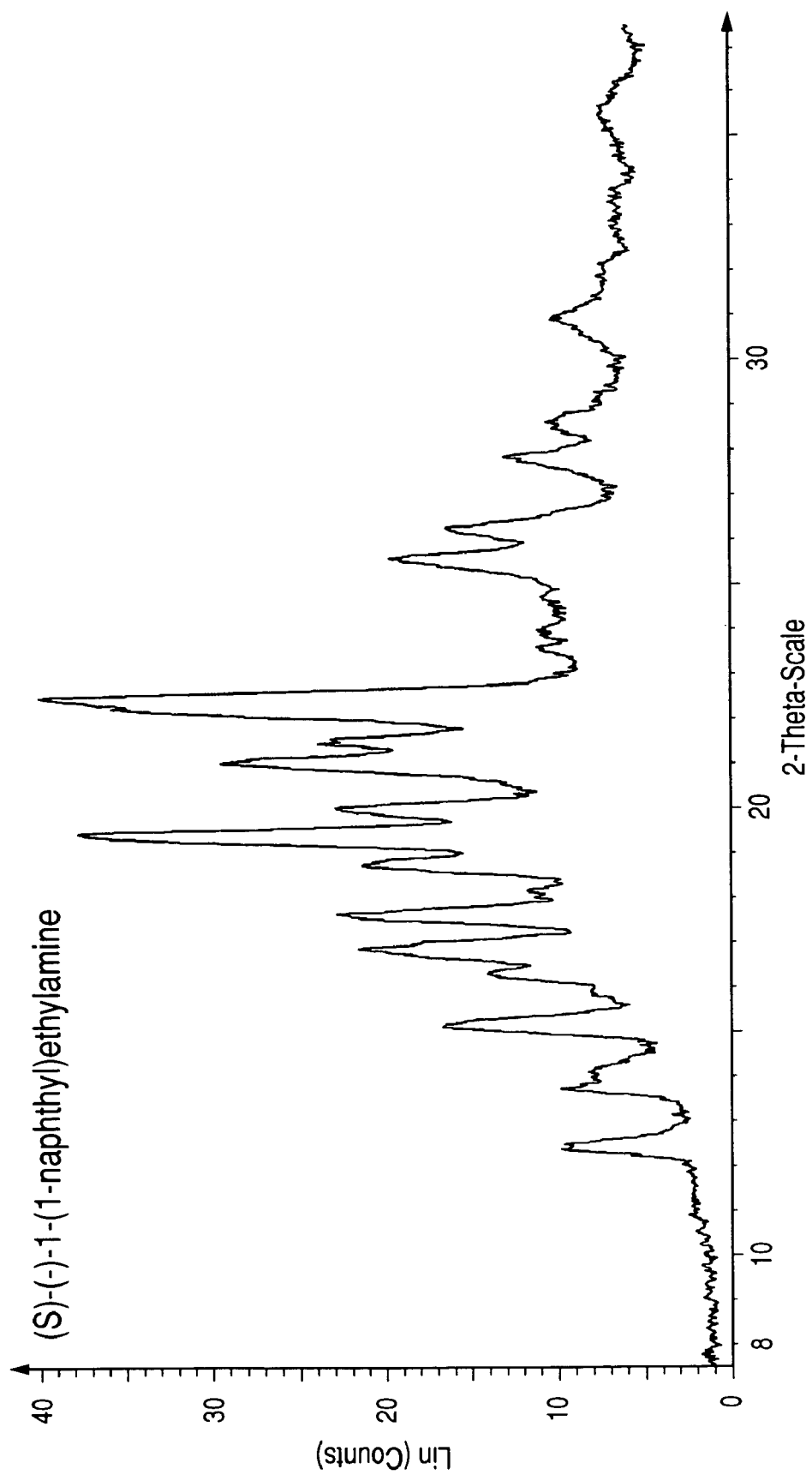
FIG. 16 shows a chart of powdered X-ray diffraction spectrum of a crystal comprising (2R)-2-propyloctanoic acid and (S)-(−)-1-(1-naphthyl)ethylamine.
Figure 17:
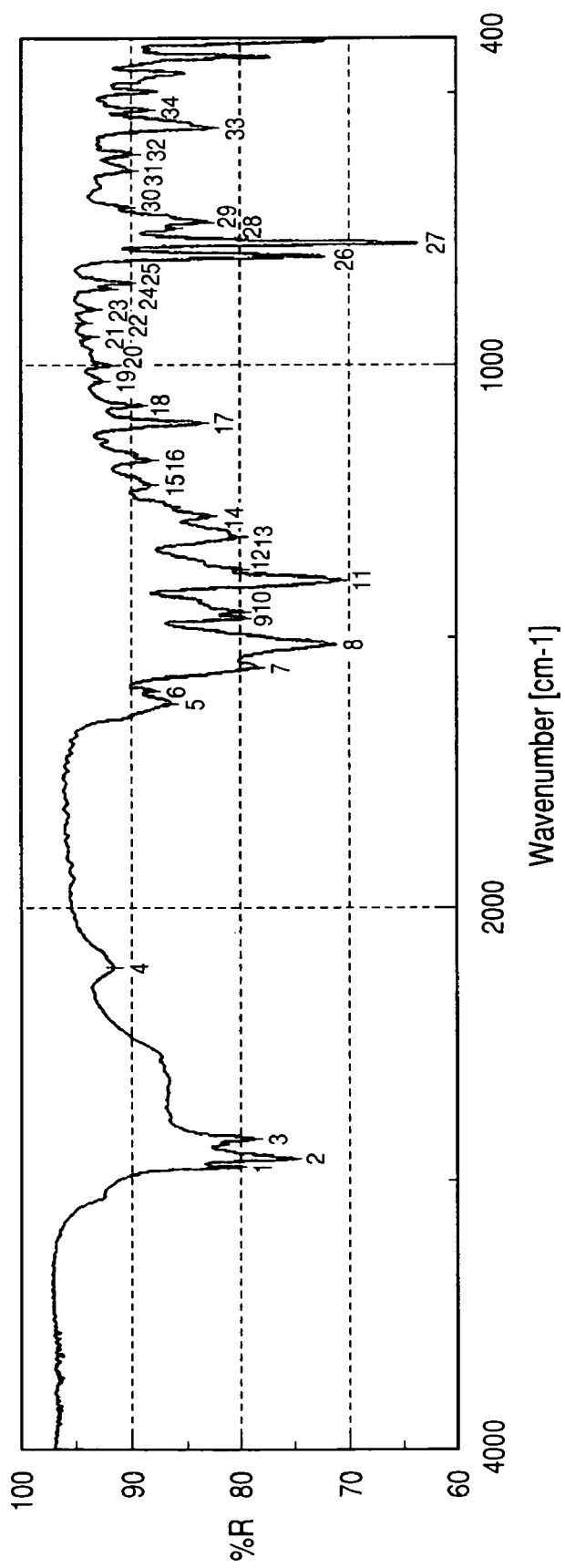
FIG. 17 shows a chart of infrared absorption spectrum (1R) of a crystal comprising (2R)-2-propyloctanoic acid and (S)-(−)-1-(1-naphthyl)ethylamine.
Figure 18:
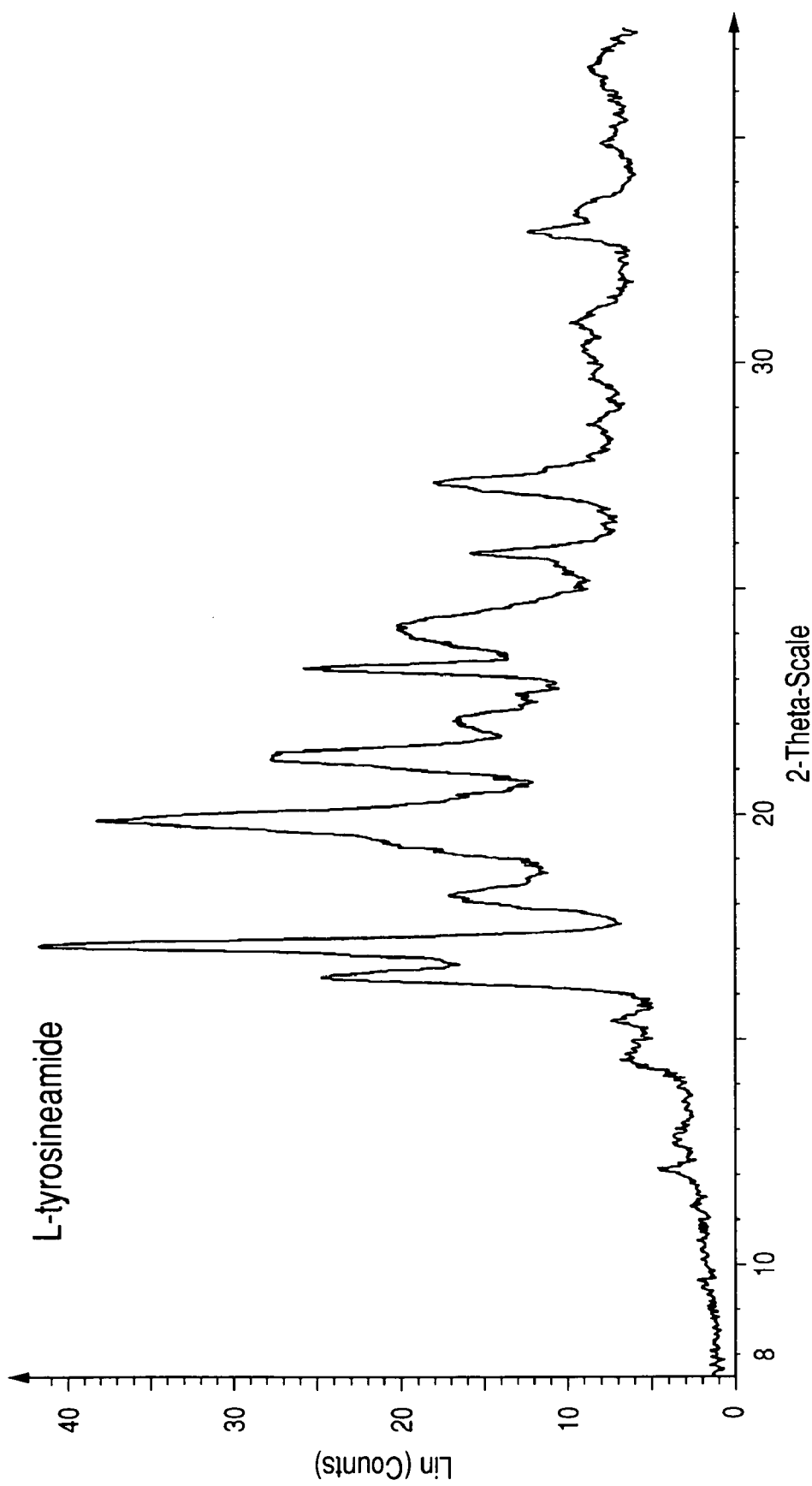
FIG. 18 shows a chart of powdered X-ray diffraction spectrum of a crystal comprising (2R)-2-propyloctanoic acid and L-tyrosinamide.
Figure 19:
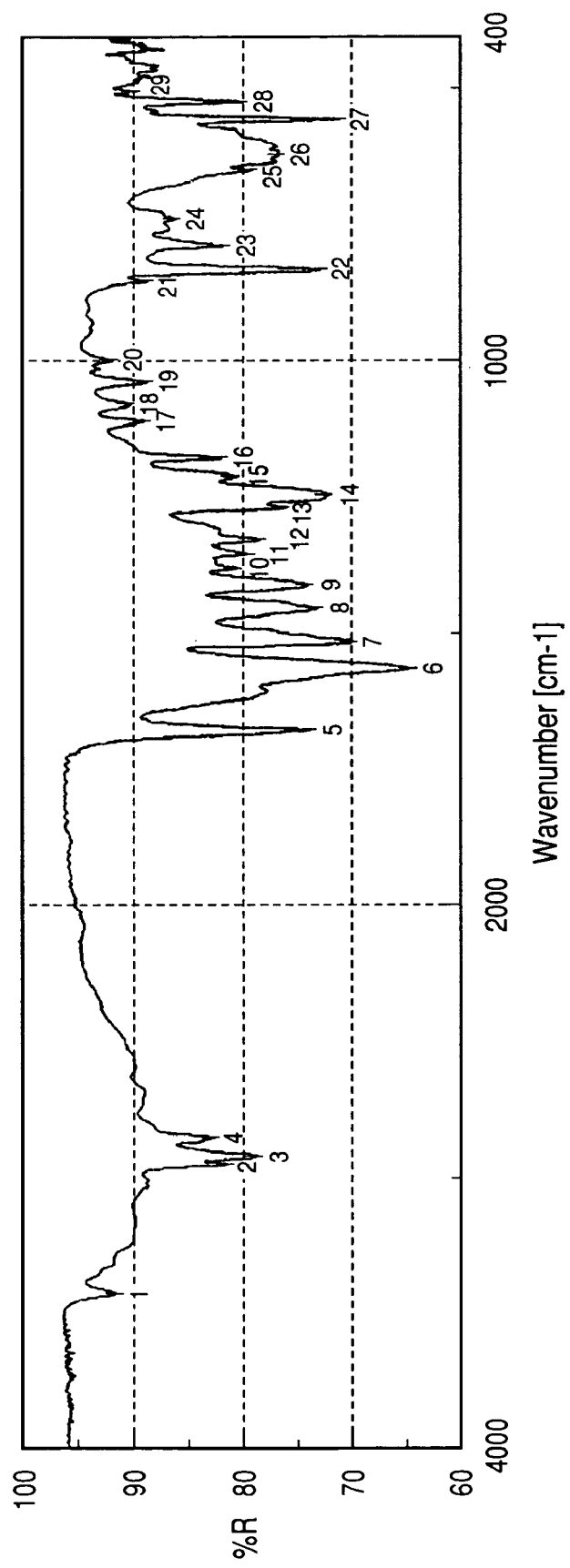
FIG. 19 shows a chart of infrared absorption spectrum (1R) of a crystal comprising (2R)-2-propyloctanoic acid and L-tyrosinamide.
Figure 20:
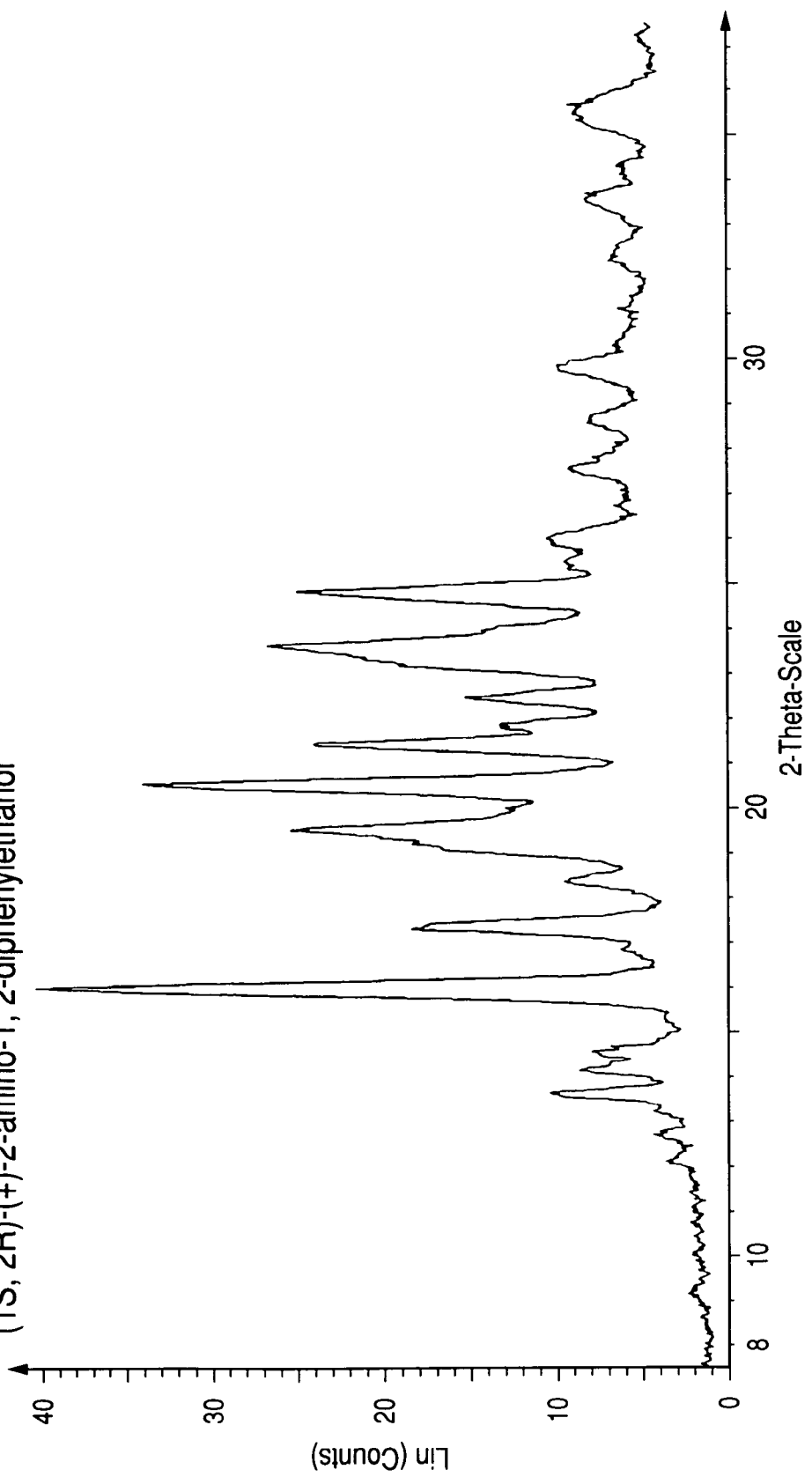
FIG. 20 shows a chart of powdered X-ray diffraction spectrum of a crystal comprising (2R)-2-propyloctanoic acid and (1S,2R)-(+)-2-amino-1,2-diphenylethanol.
Figure 21:
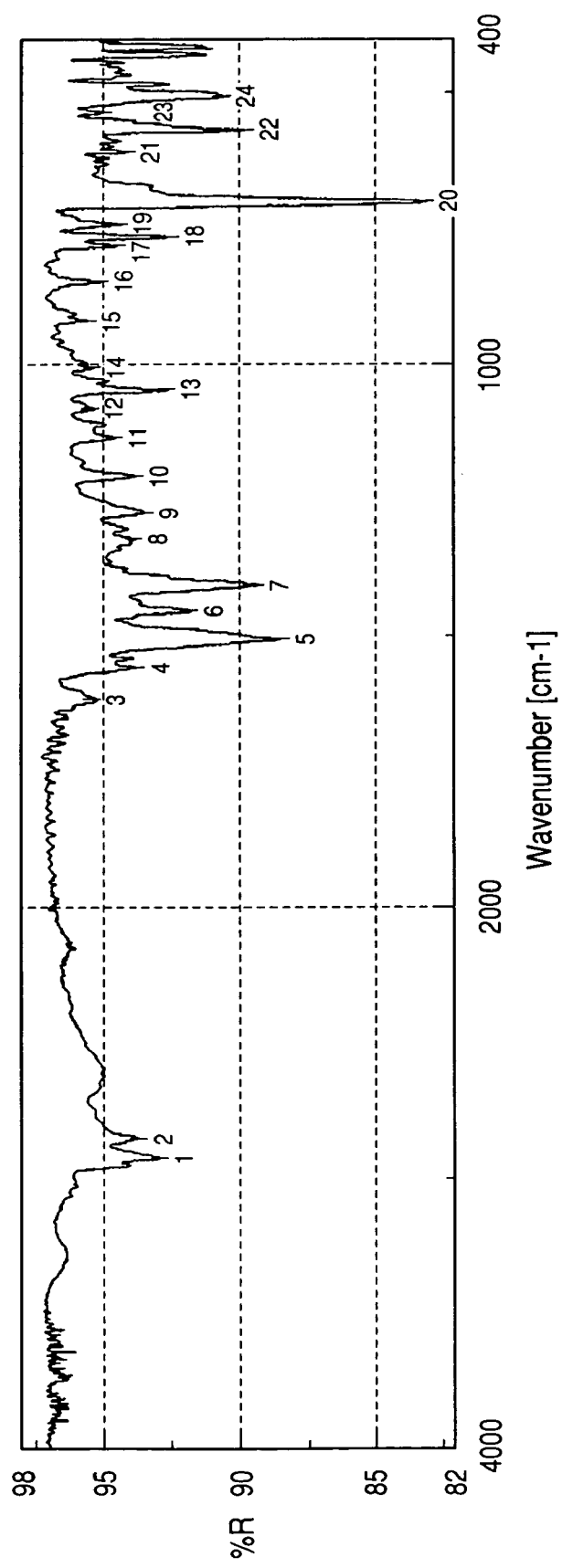
FIG. 21 shows a chart of infrared absorption spectrum (IR) of a crystal comprising (2R)-2-propyloctanoic acid and (1S, 2R)-(+)-2-amino-1,2-diphenylethanol.
Figure 22:
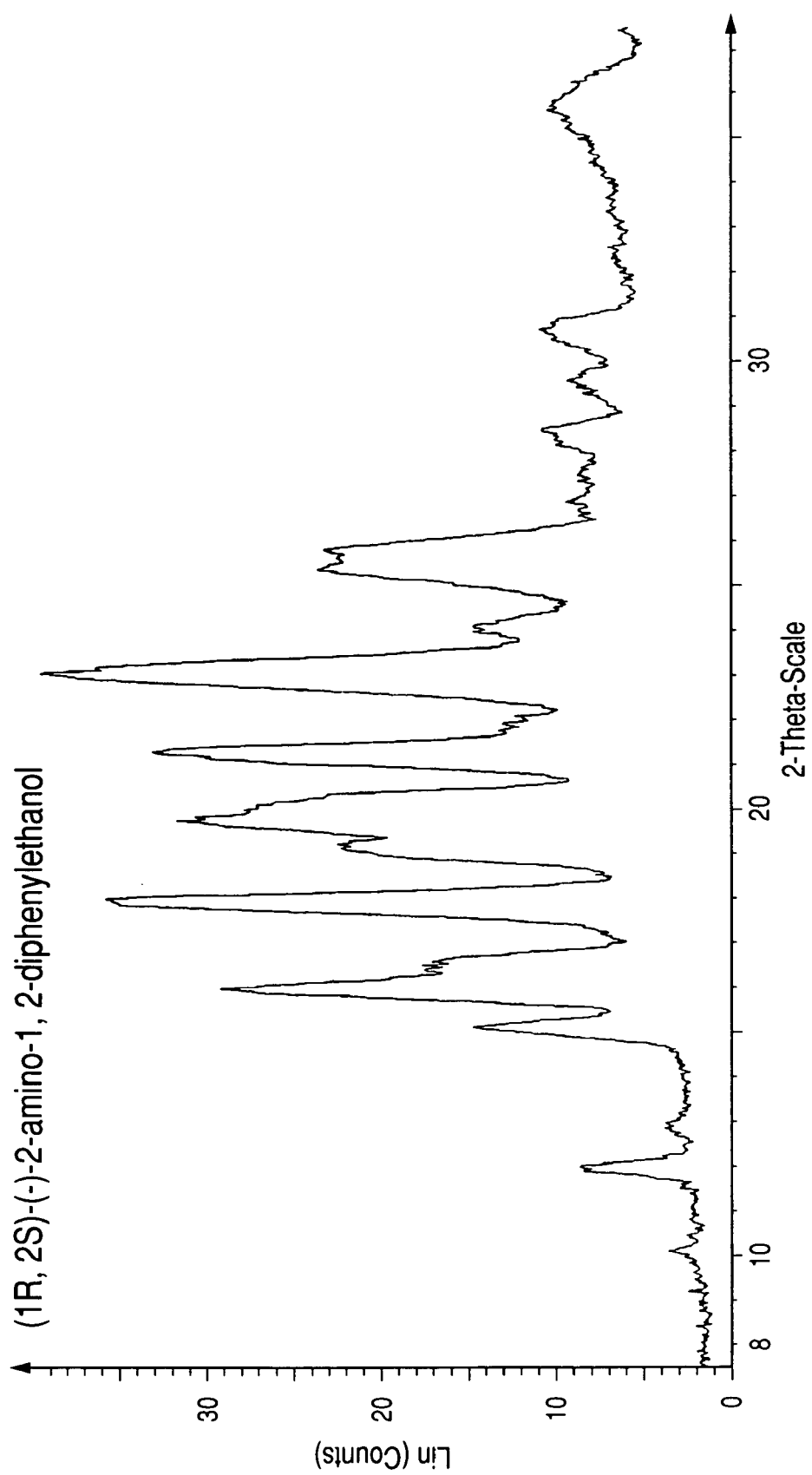
FIG. 22 shows a chart of powdered X-ray diffraction spectrum of a crystal comprising (2R)-2-propyloctanoic acid and (1R,2S)-(−)-2-amino-1,2-diphenylethanol.
Figure 23:
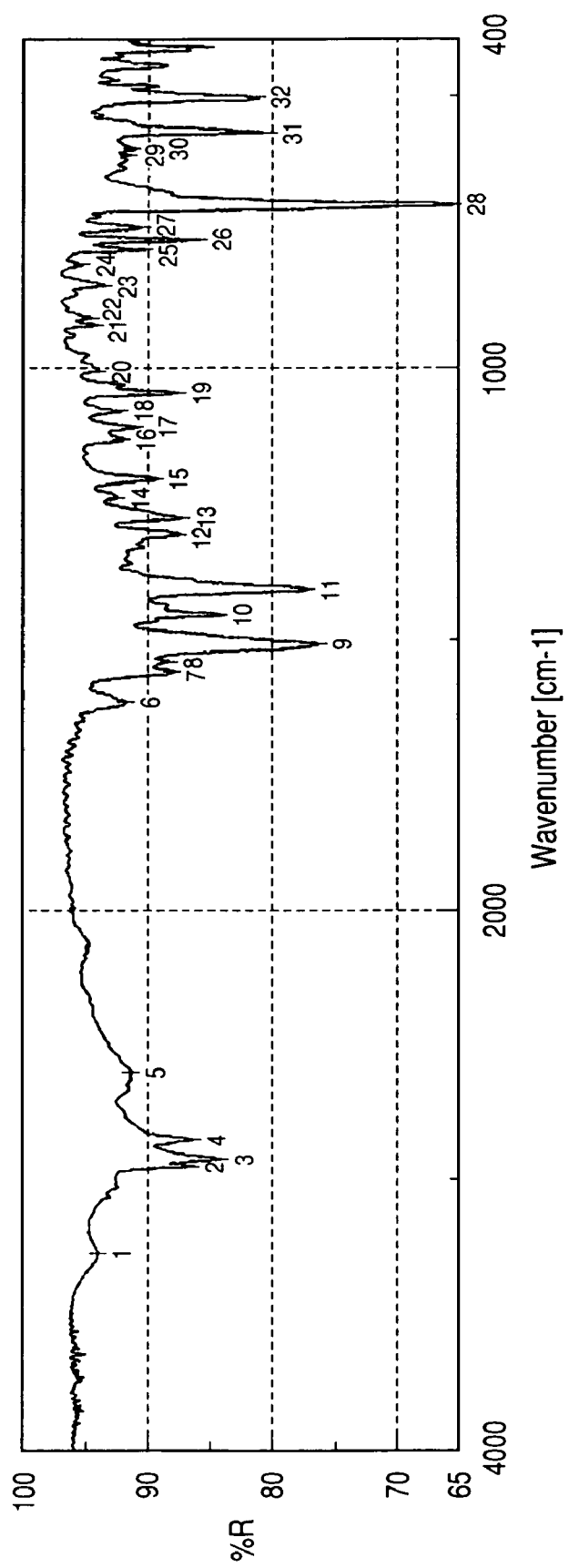
FIG. 23 shows a chart of infrared absorption spectrum (1R) of a crystal comprising (2R)-2-propyloctanoic acid and (1R, 2S)-(−)-2-amino-1,2-diphenylethanol.
Figure 24:
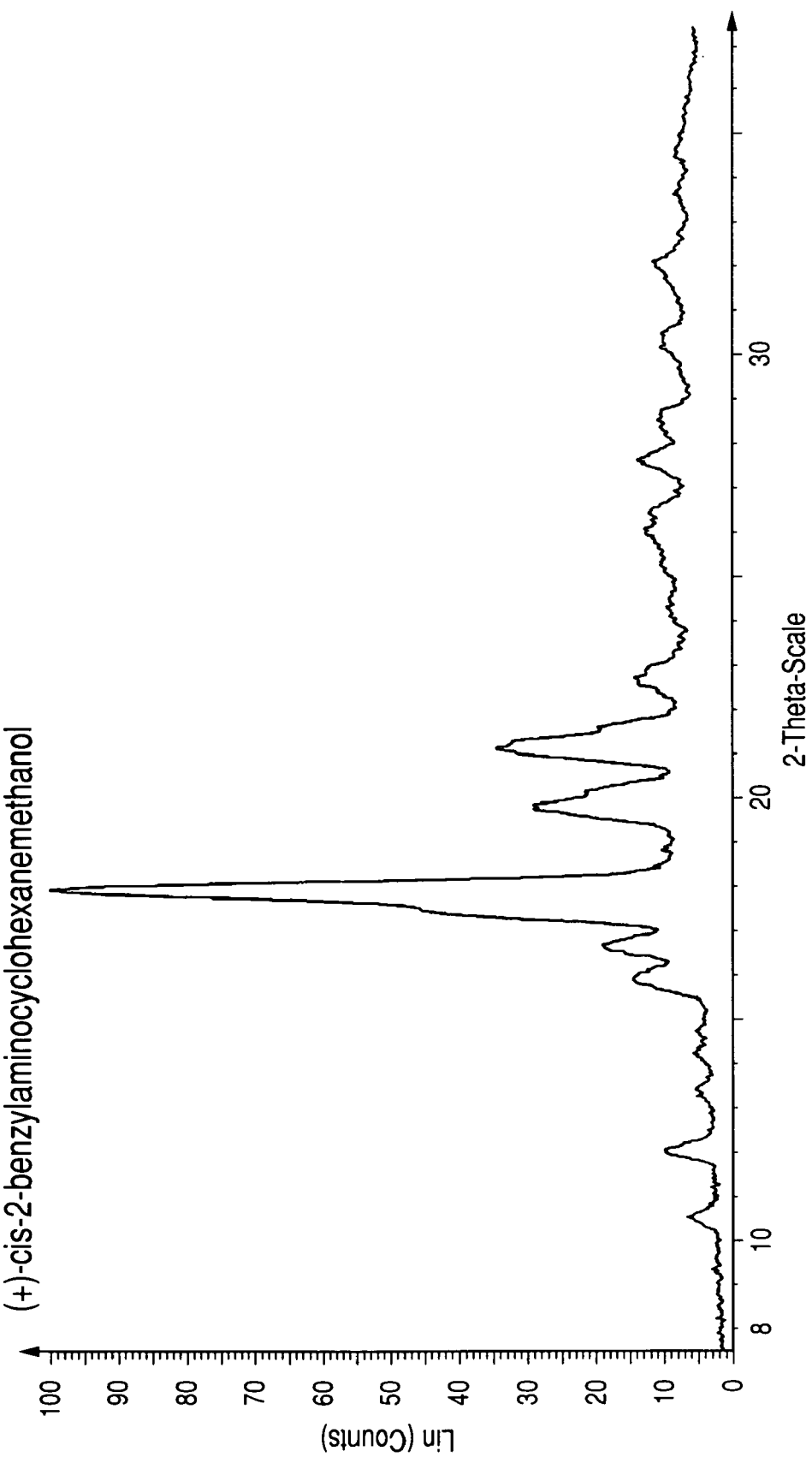
FIG. 24 shows a chart of powdered X-ray diffraction spectrum of a crystal comprising (2R)-2-propyloctanoic acid and (+)-cis-2-benzylaminocyclohexanemethanol.
Figure 25:
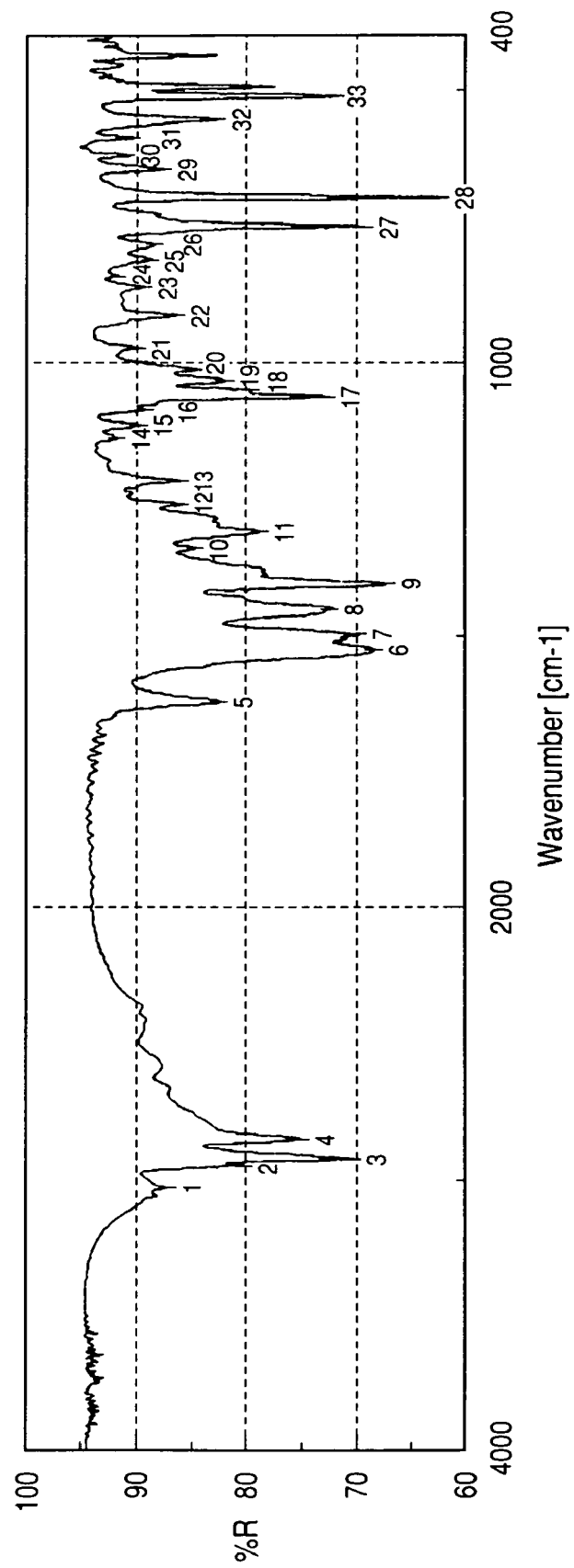
FIG. 25 shows a chart of infrared absorption spectrum (1R) of a crystal comprising (2R)-2-propyloctanoic acid and (+)-cis-2-benzylaminocyclohexanemethanol.

Physicochemical Data of the Crystal:

For the compound produced in Example 1, a chart of powdered X-ray diffraction spectrum is shown in FIG. 1, a chart of infrared absorption spectrum (1R) in FIG. 2, and a chart of differential scanning calorimetry (DSC) in FIG. 3, respectively. In addition, the results of elemental analysis and specific rotation are described.

[1] Powdered X-ray Diffraction Spectrum

| <Measurement conditions> | |
| --- | --- |
| Apparatus: | BRUKER axs, BRUKER D8 DISCOVER with GADD(C2) |
| Target: | Cu |
| Filter: | none |
| Voltage: | 40 kV |
| Current: | 40 mA |
| Time of Exposure: | 5 min |

<Results>

Figure 26:
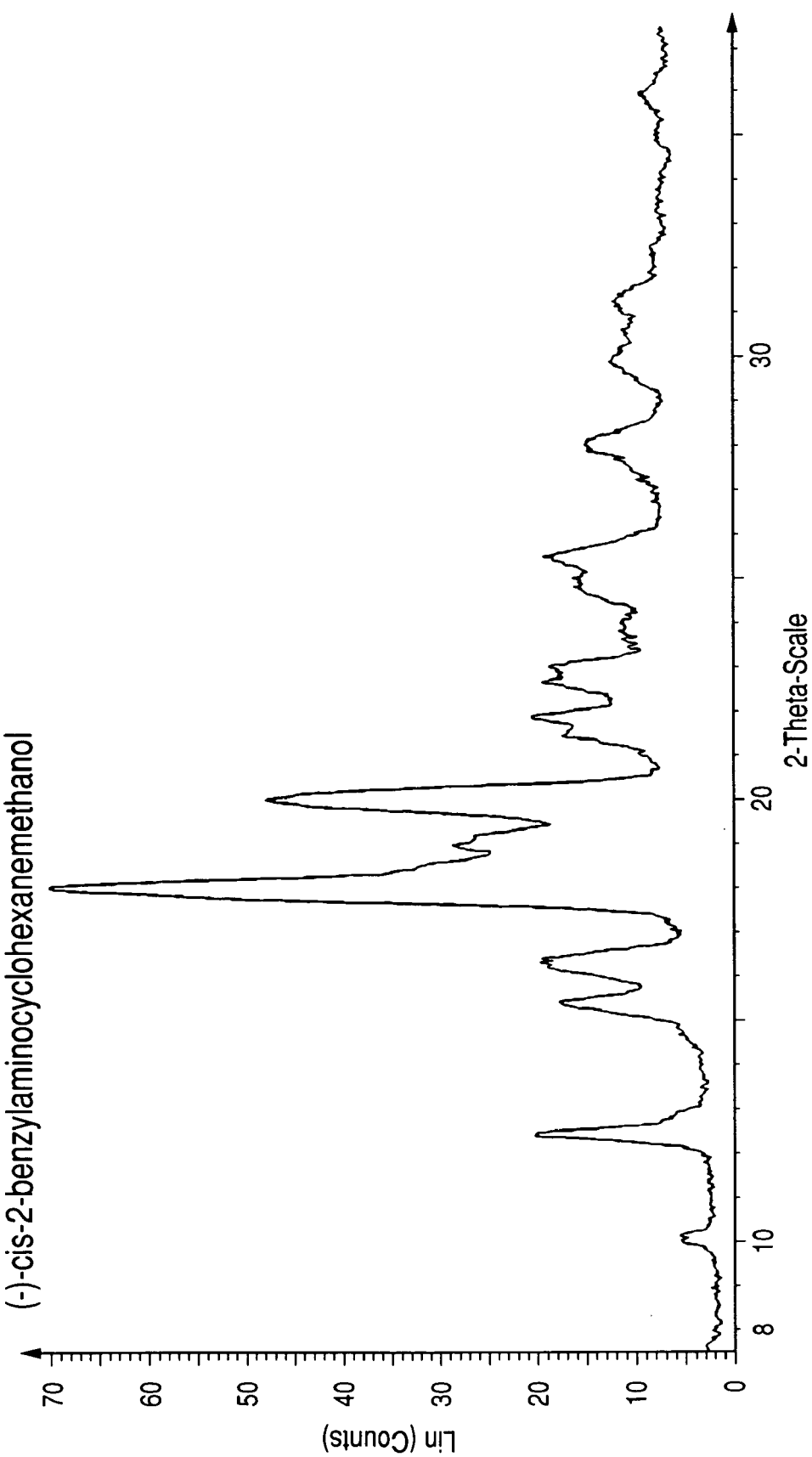
FIG. 26 shows a chart of powdered X-ray diffraction spectrum of a crystal comprising (2R)-2-propyloctanoic acid and (−)-cis-2-benzylaminocyclohexanemethanol.
Figure 27:
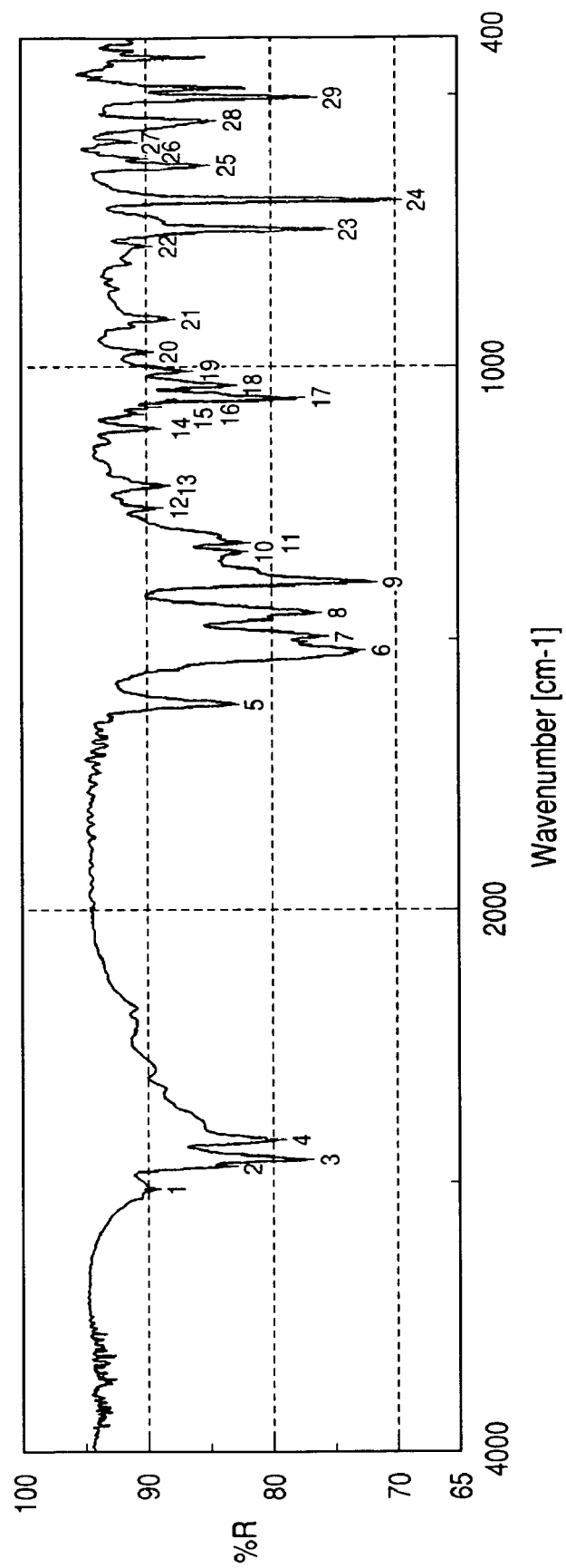
FIG. 27 shows a chart of infrared absorption spectrum (1R) of a crystal comprising (2R)-2-propyloctanoic acid and (−)-cis-2-benzylaminocyclohexanemethanol.
Figure 28:
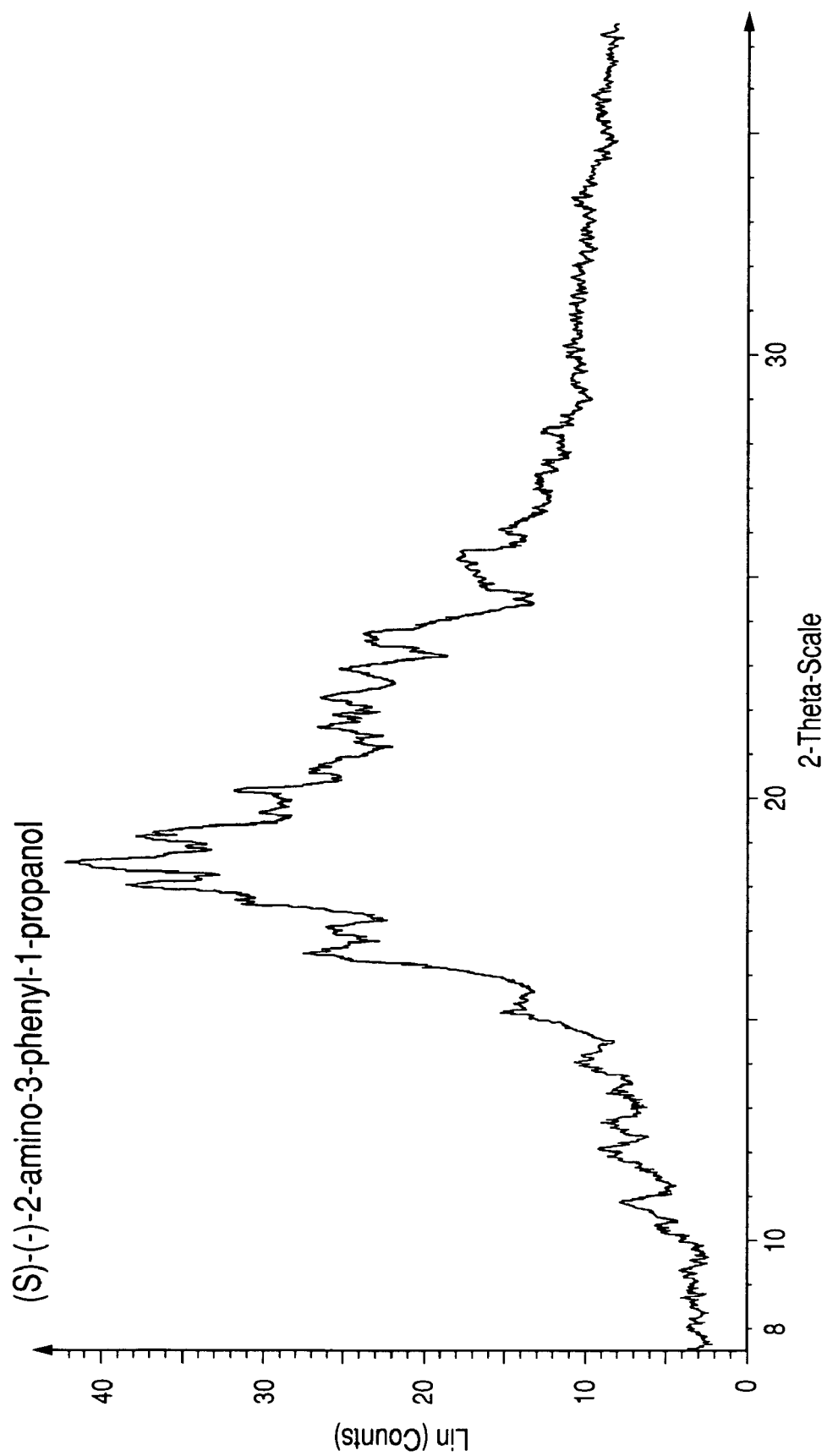
FIG. 28 shows a chart of powdered X-ray diffraction spectrum of a crystal comprising (2R)-2-propyloctanoic acid and (S)-(−)-2-amino-3-phenyl-1-propanol.
Figure 29:
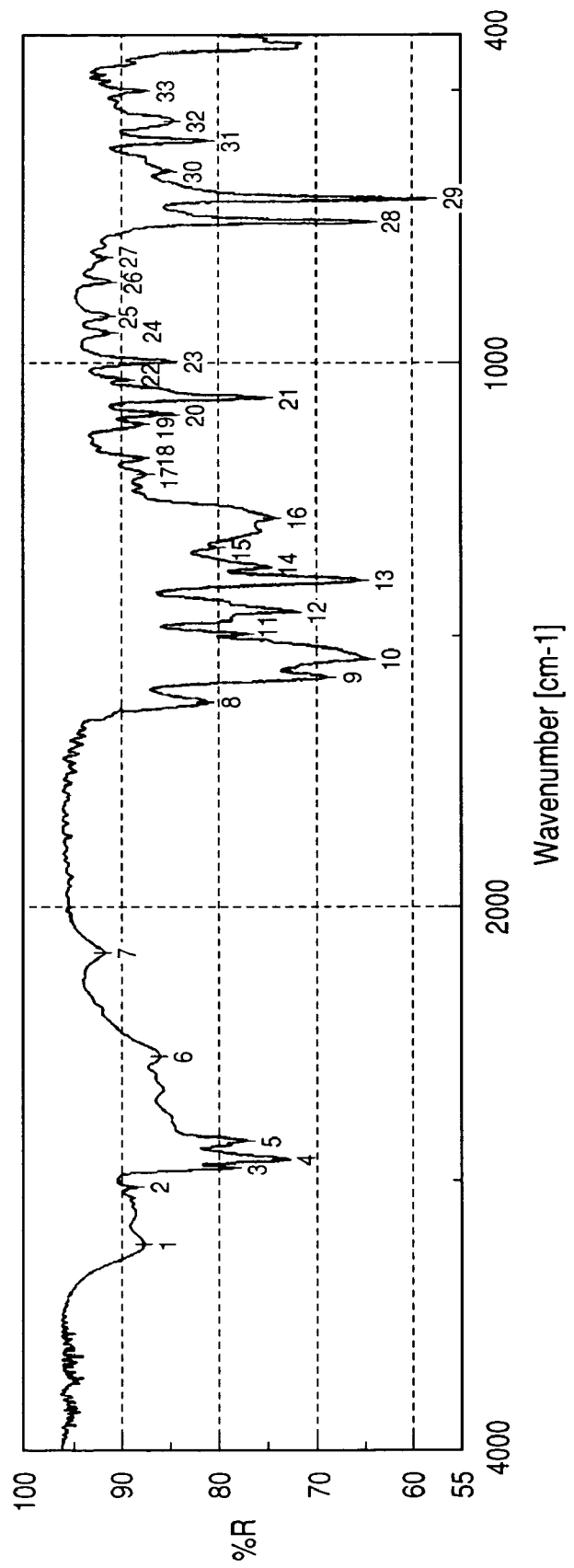
FIG. 29 shows a chart of infrared absorption spectrum (1R) of a crystal comprising (2R)-2-propyloctanoic acid and (S)-(−)-2-amino-3-phenyl-1-propanol.
Figure 30:
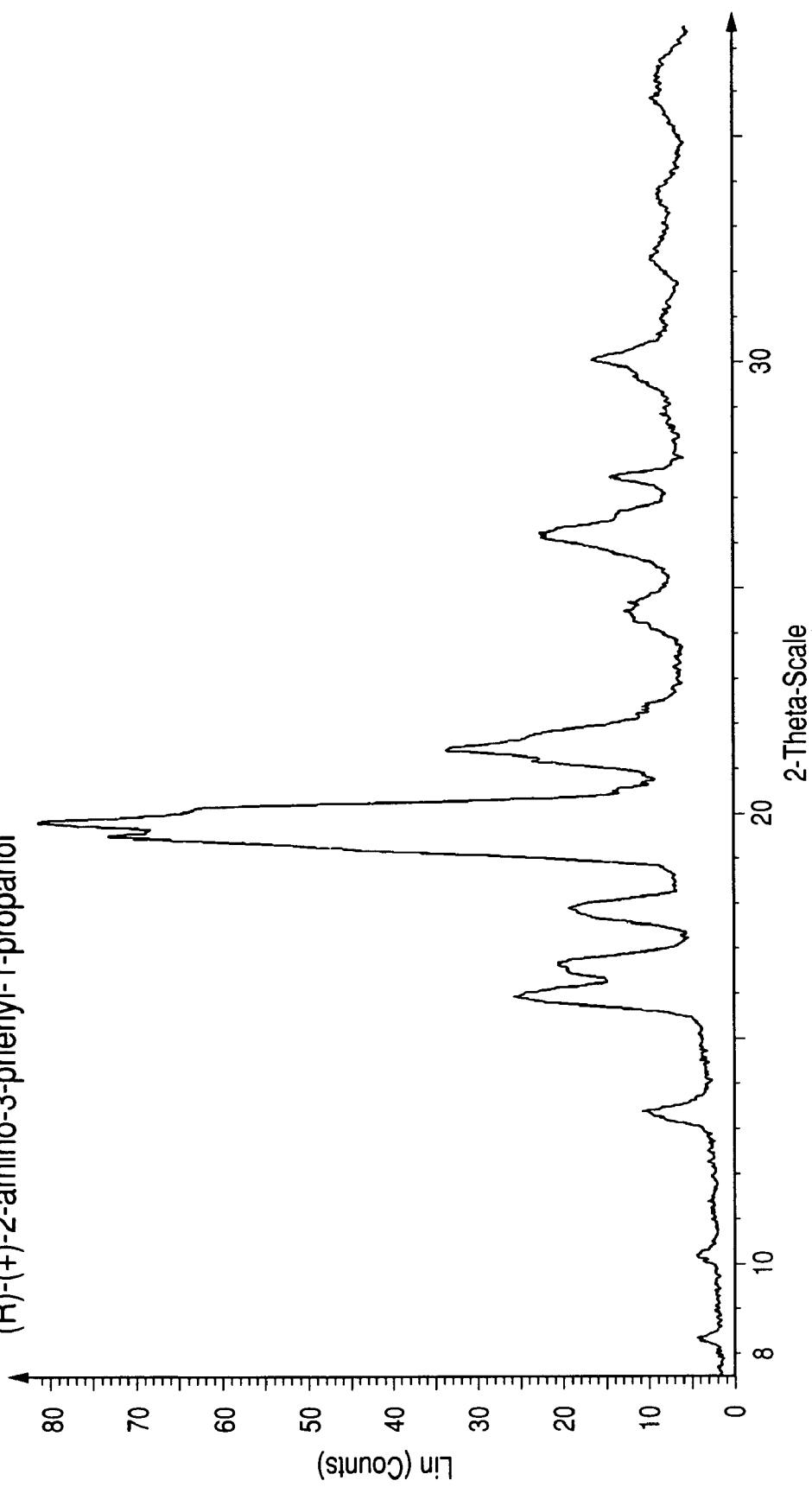
FIG. 30 shows a chart of powdered X-ray diffraction spectrum of a crystal comprising (2R)-2-propyloctanoic acid and (R)-(+)-2-amino-3-phenyl-1-propanol.
Figure 31:
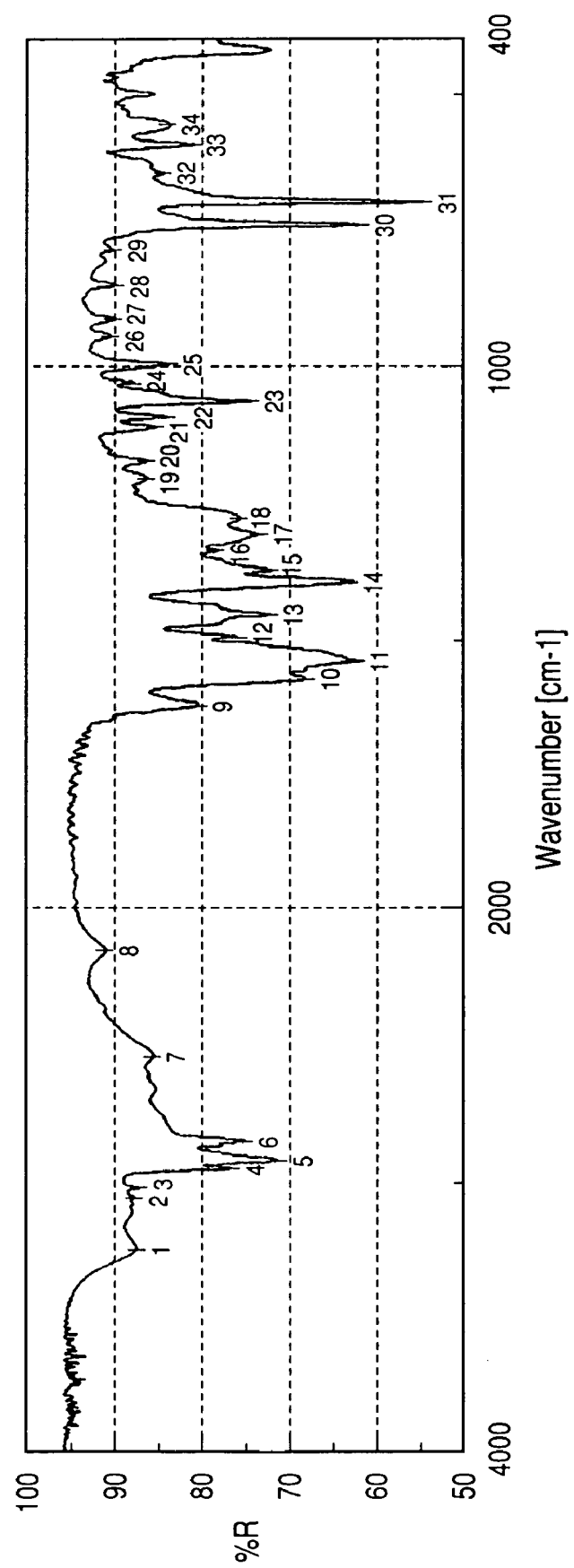
FIG. 31 shows a chart of infrared absorption spectrum (1R) of a crystal comprising (2R)-2-propyloctanoic acid and (R)-(+)-2-amino-3-phenyl-1-propanol.
Figure 32:
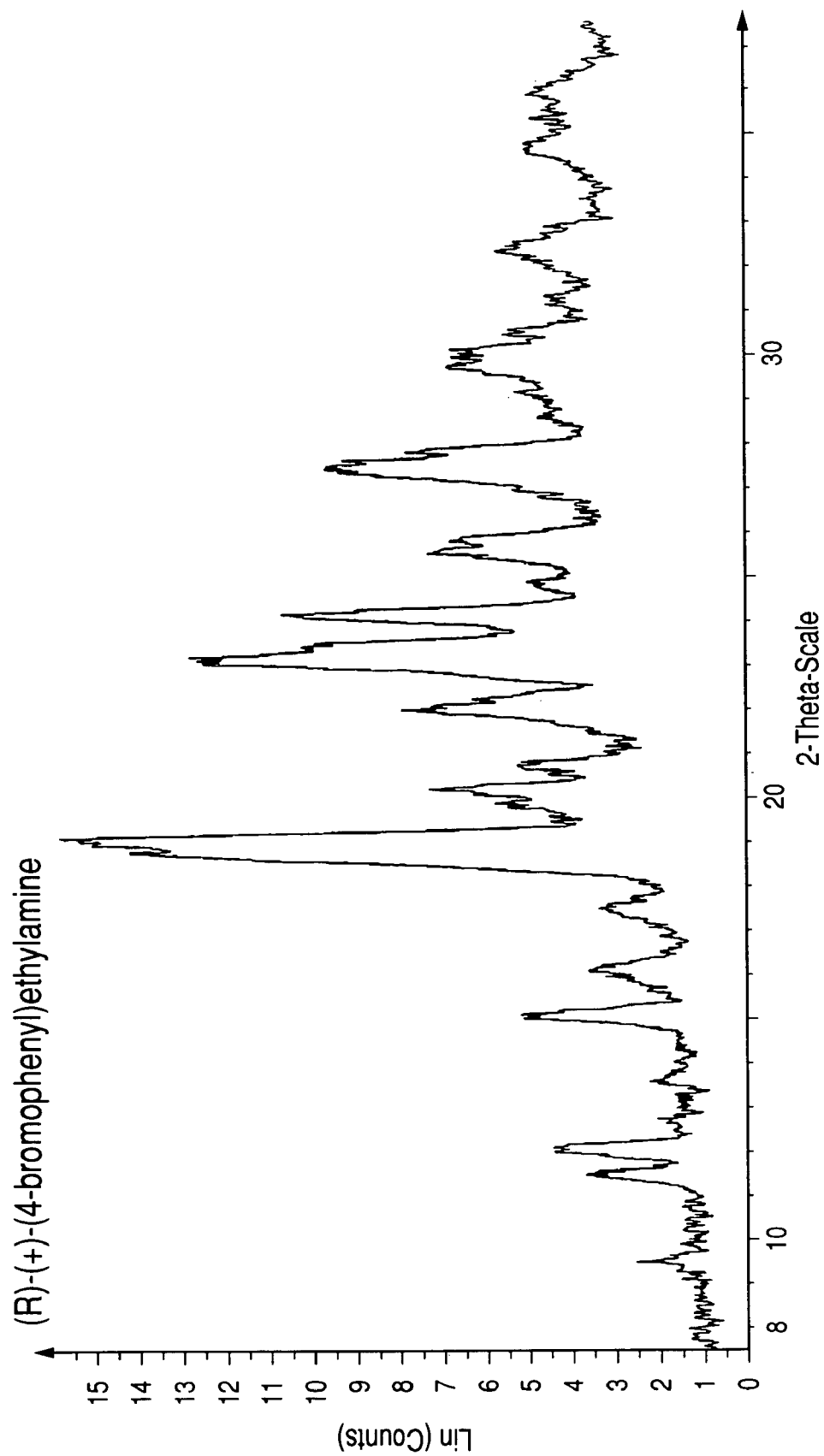
FIG. 32 shows a chart of powdered X-ray diffraction spectrum of a crystal comprising (2R)-2-propyloctanoic acid and (R)-(+)-1-(4-bromophenyl)ethylamine.
Figure 33:
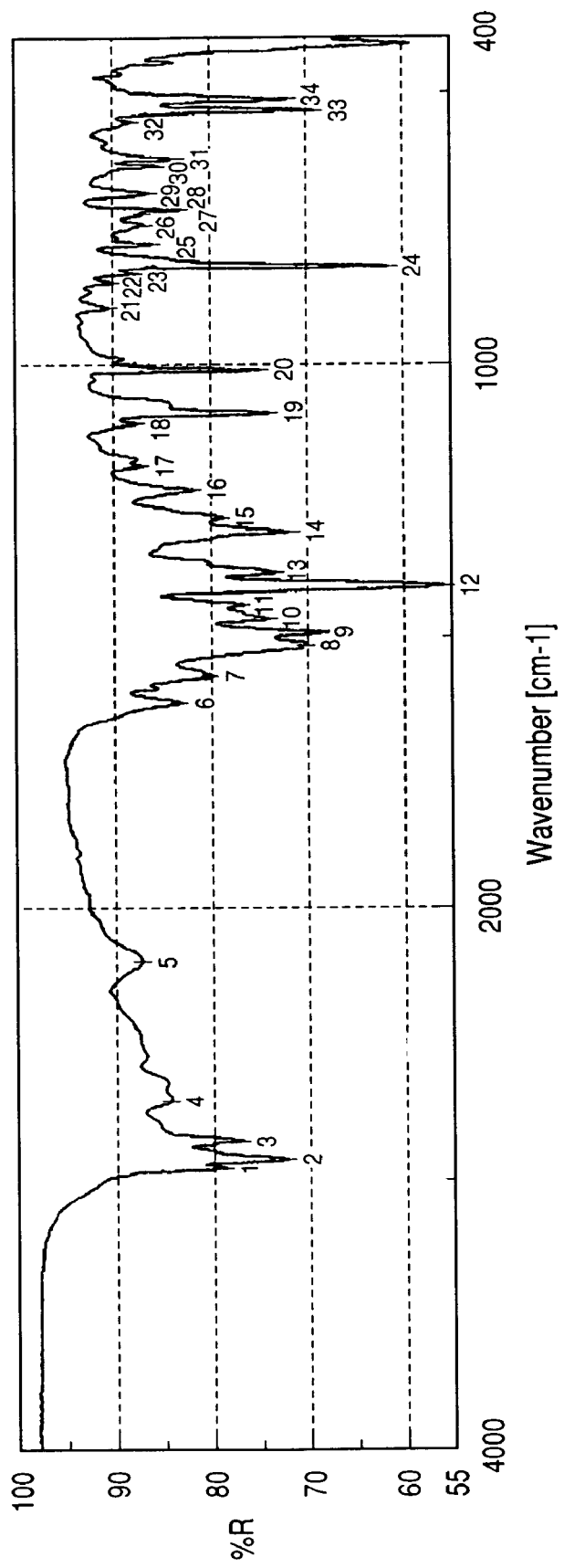
FIG. 33 shows a chart of infrared absorption spectrum (1R) of a crystal comprising (2R)-2-propyloctanoic acid and (R)-(+)-1-(4-bromophenyl)ethylamine.
Figure 34:
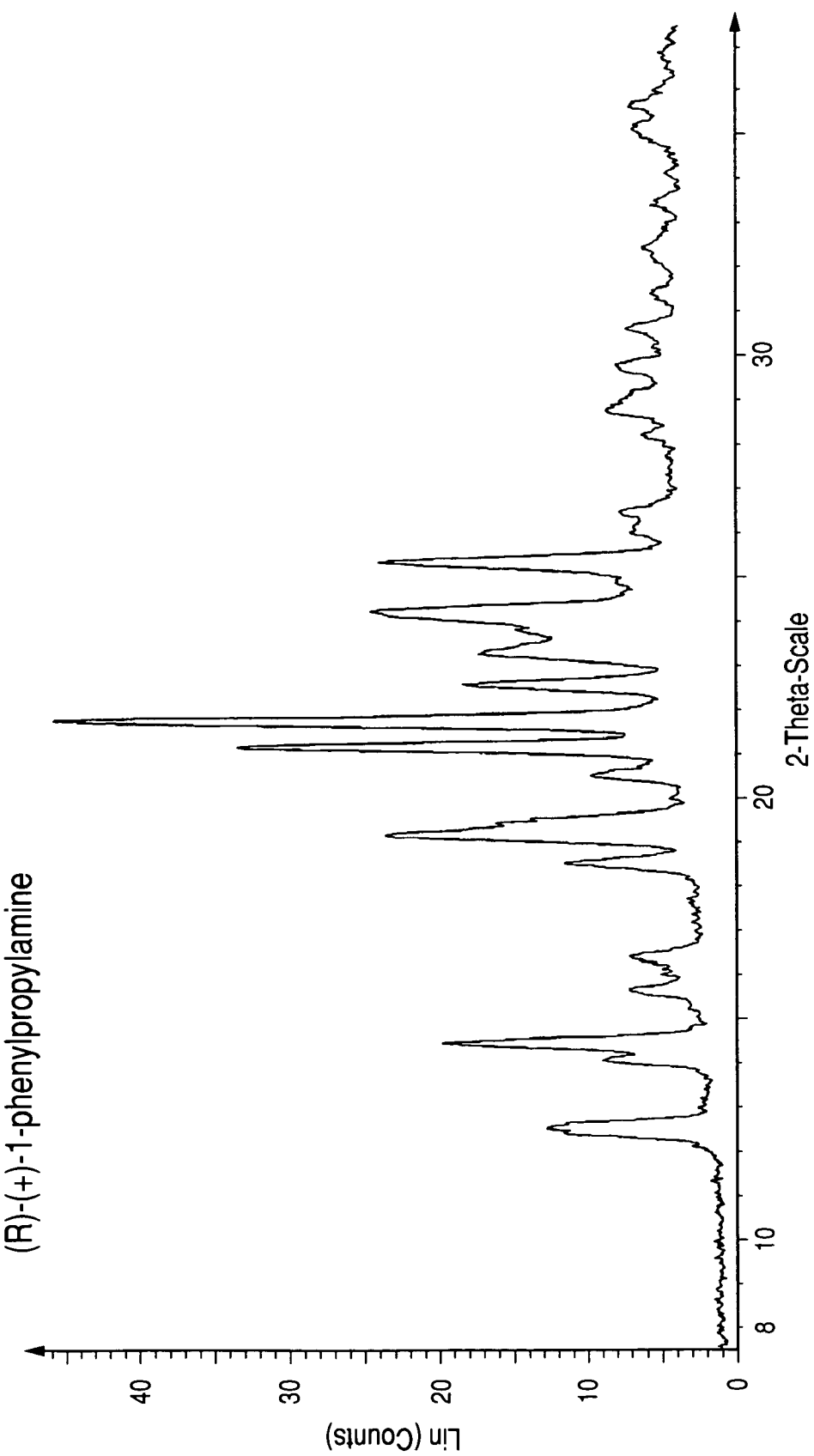
FIG. 34 shows a chart of powdered X-ray diffraction spectrum of a crystal comprising (2R)-2-propyloctanoic acid and (R)-(+)-1-phenylpropylamine.
Figure 35:
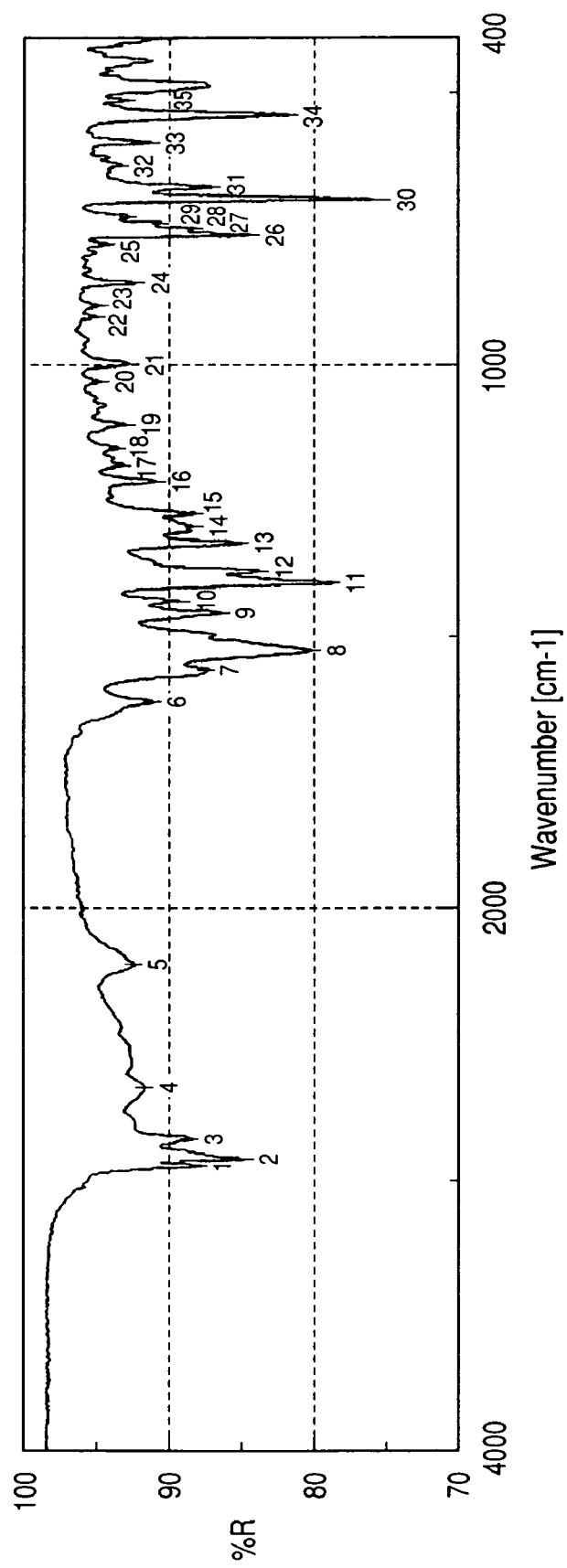
FIG. 35 shows a chart of infrared absorption spectrum (1R) of a crystal comprising (2R)-2-propyloctanoic acid and (R)-(+)-1-phenylpropylamine.
Figure 36:
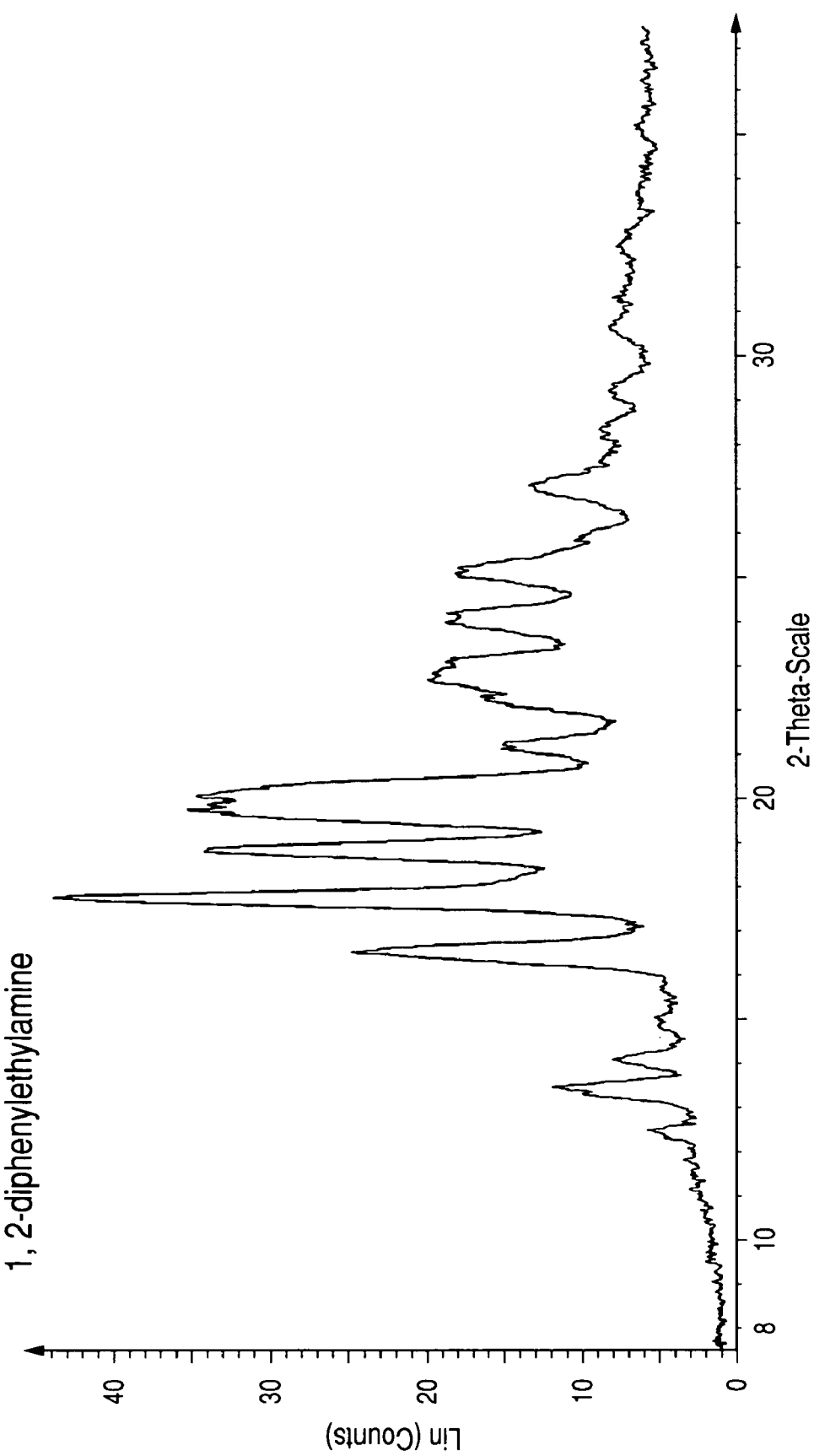
FIG. 36 shows a chart of powdered X-ray diffraction spectrum of a crystal comprising (2R)-2-propyloctanoic acid and 1,2-diphenylethylamine.
Figure 37:
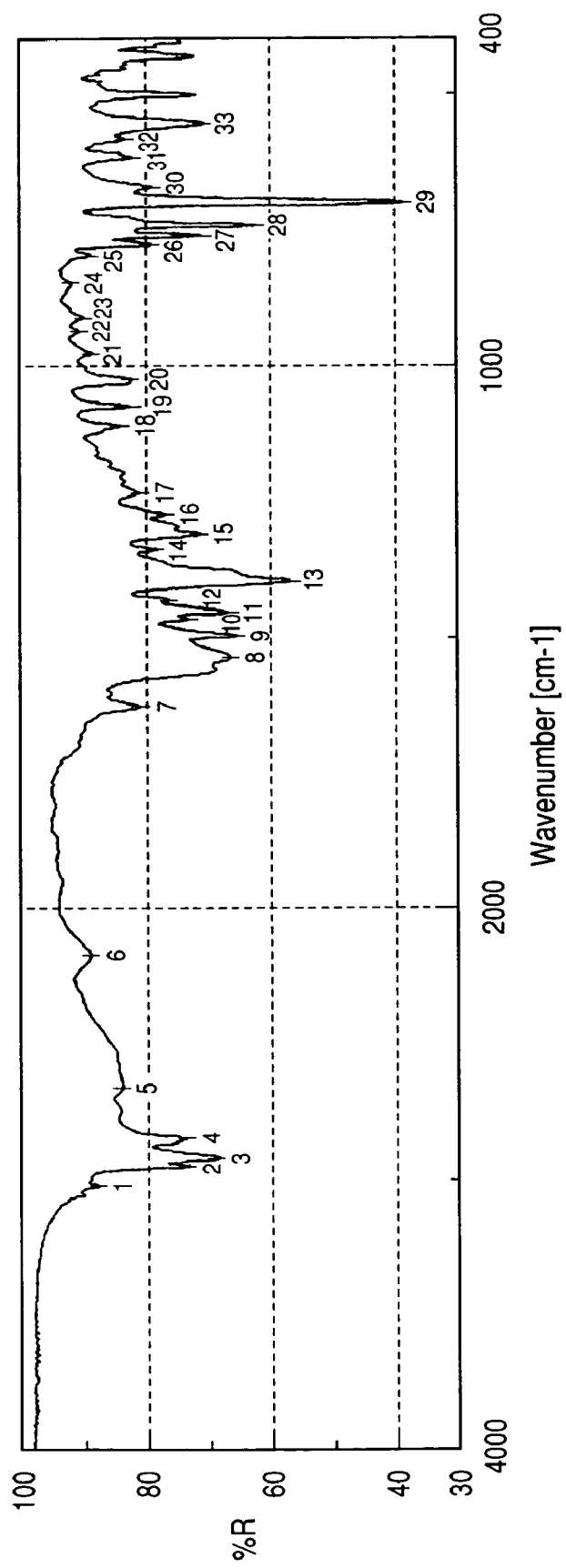
FIG. 37 shows a chart of infrared absorption spectrum (1R) of a crystal comprising (2R)-2-propyloctanoic acid and 1,2-diphenylethylamine.
Figure 38:
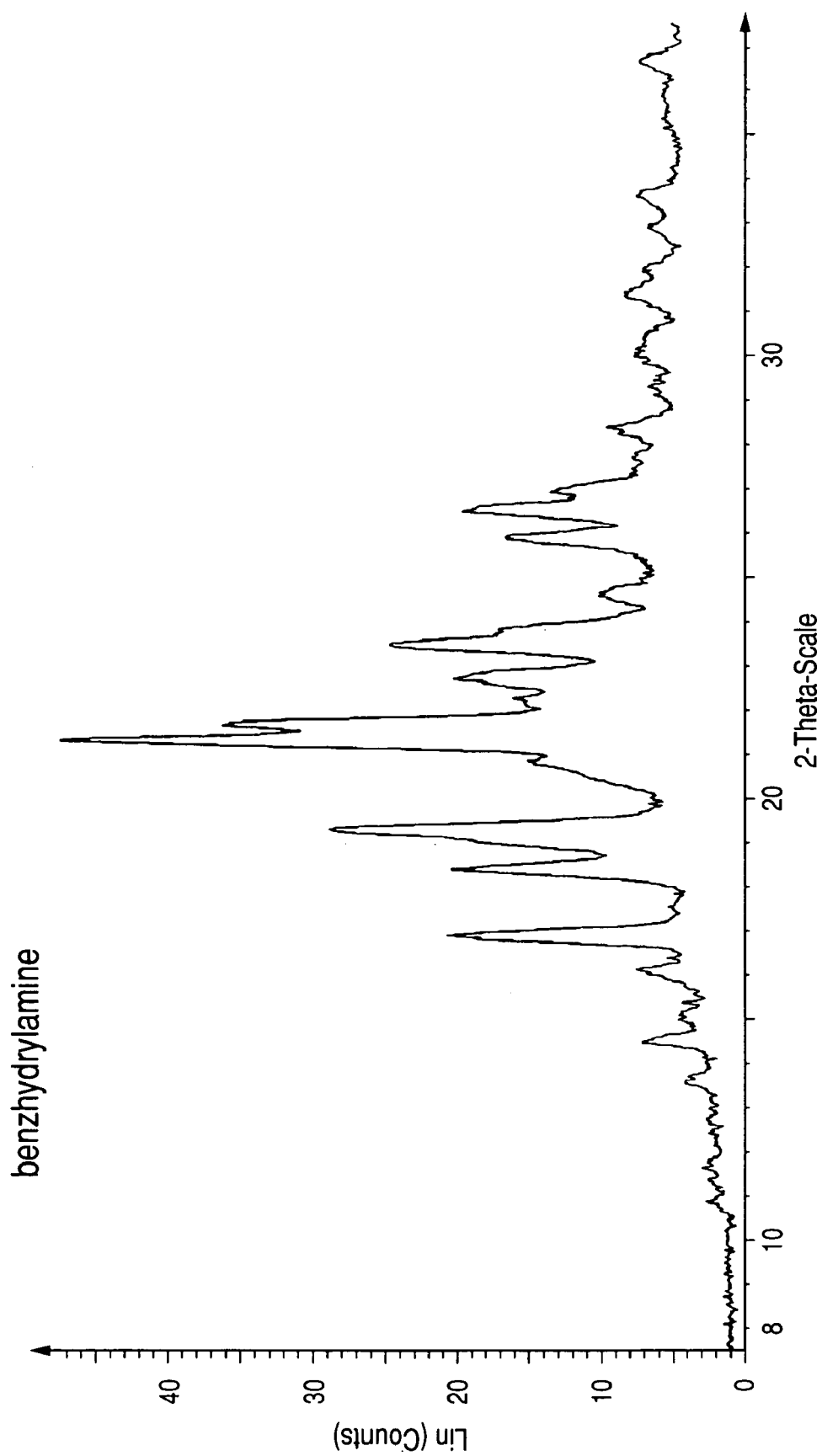
FIG. 38 shows a chart of powdered X-ray diffraction spectrum of a crystal comprising (2R)-2-propyloctanoic acid and benzhydrylamine.
Figure 39:
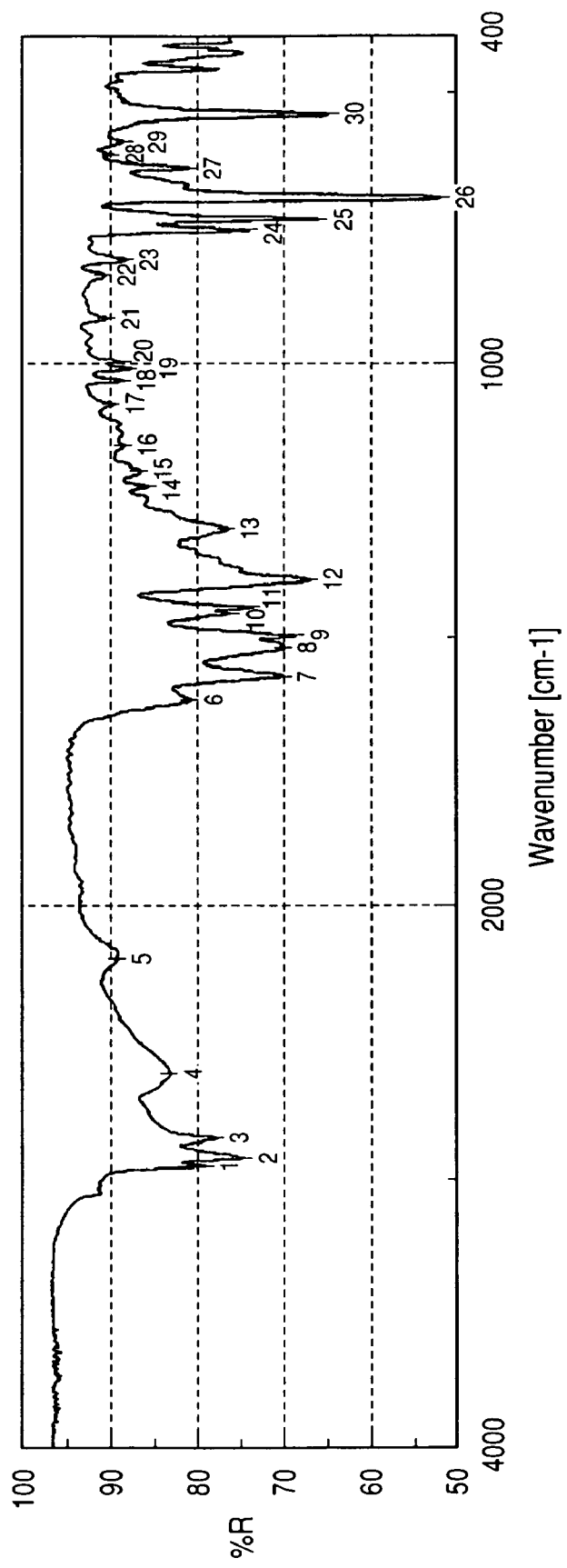
FIG. 39 shows a chart of infrared absorption spectrum (1R) of a crystal comprising (2R)-2-propyloctanoic acid and benzhydrylamine.
Figure 40:
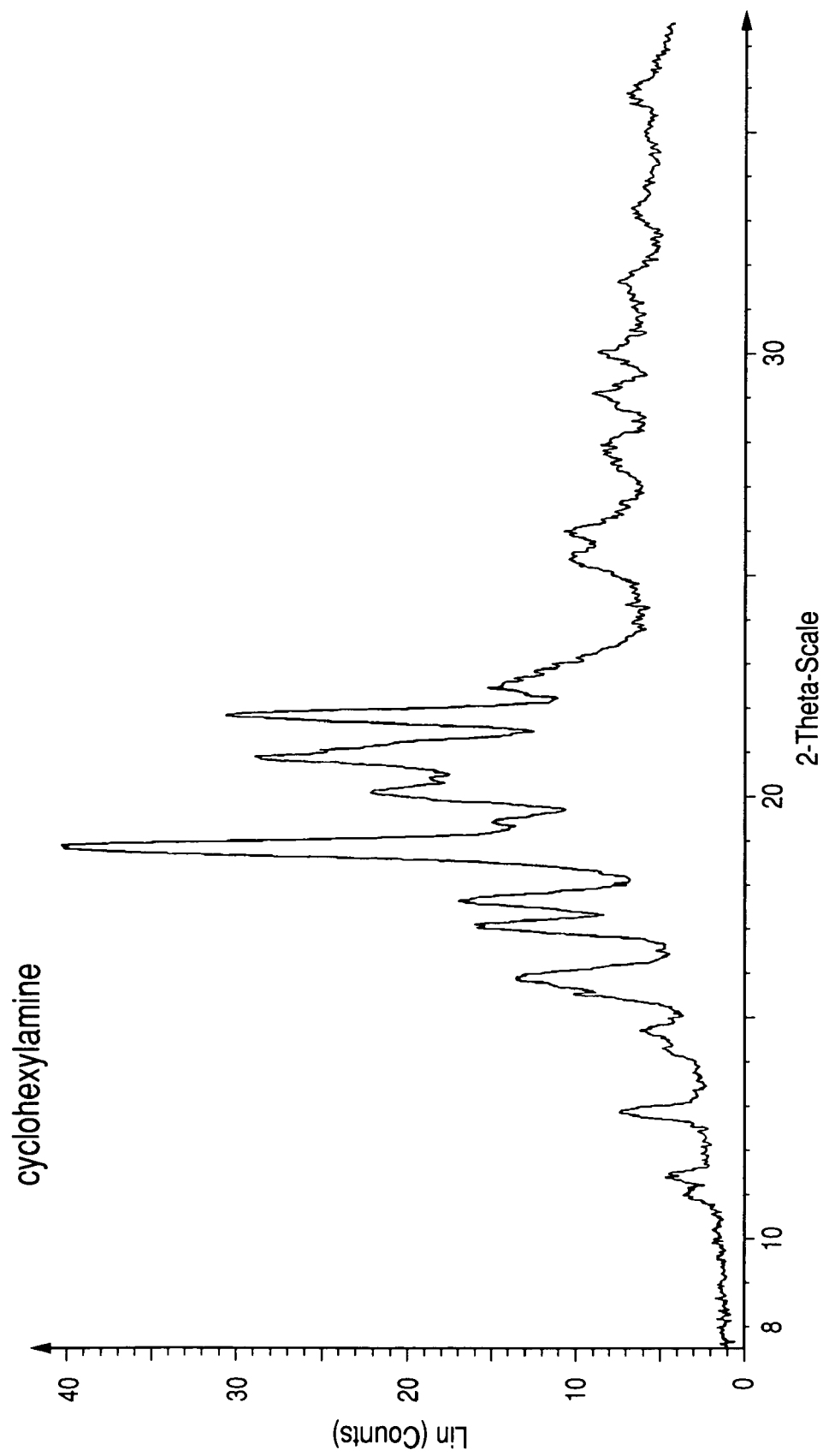
FIG. 40 shows a chart of powdered X-ray diffraction spectrum of a crystal comprising (2R)-2-propyloctanoic acid and cyclohexylamine.
Figure 41:
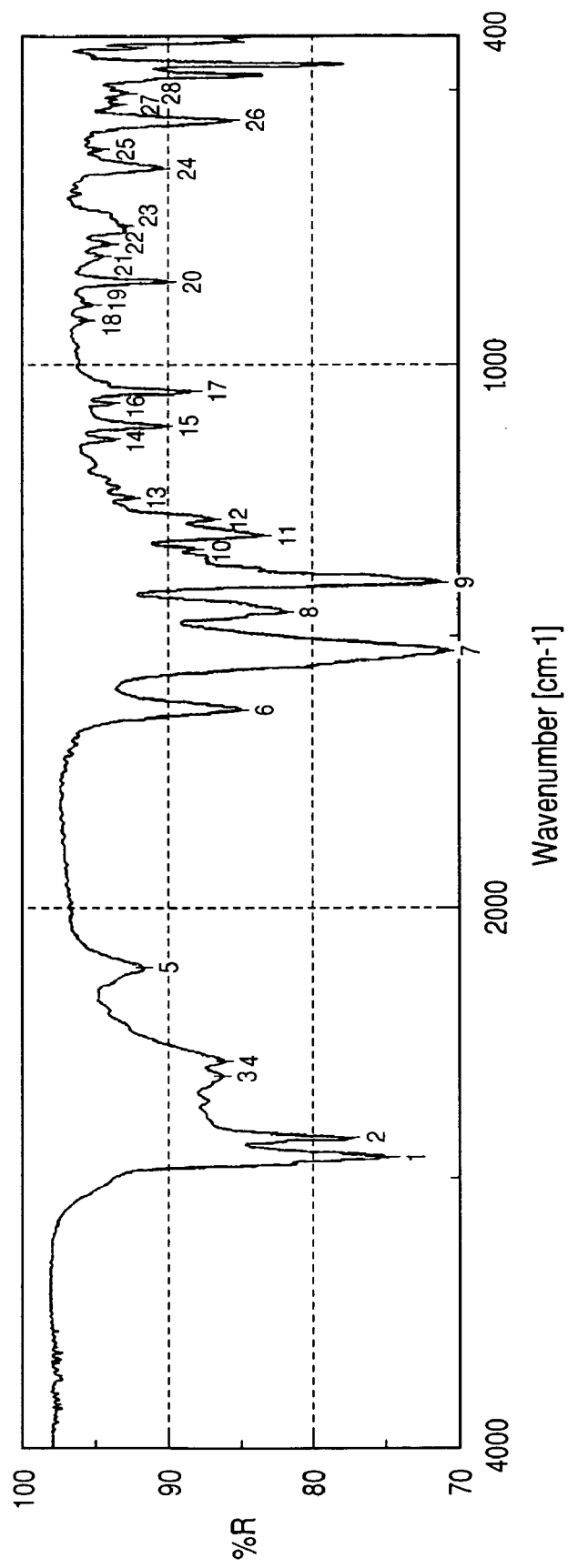
FIG. 41 shows a chart of infrared absorption spectrum (1R) of a crystal comprising (2R)-2-propyloctanoic acid and cyclohexylamine.
Figure 42:
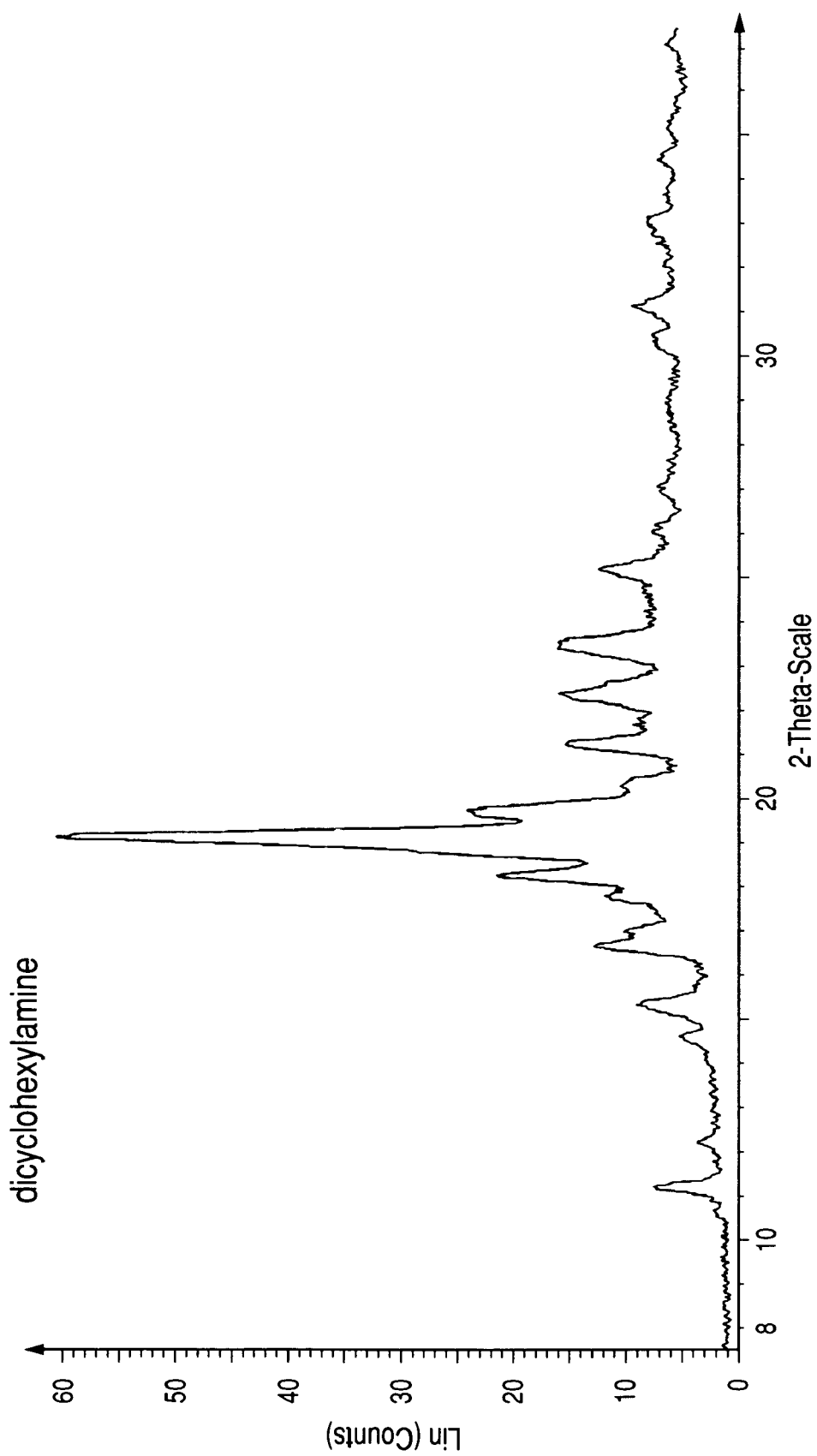
FIG. 42 shows a chart of powdered X-ray diffraction spectrum of a crystal comprising (2R)-2-propyloctanoic acid and dicyclohexylamine.
Figure 43:
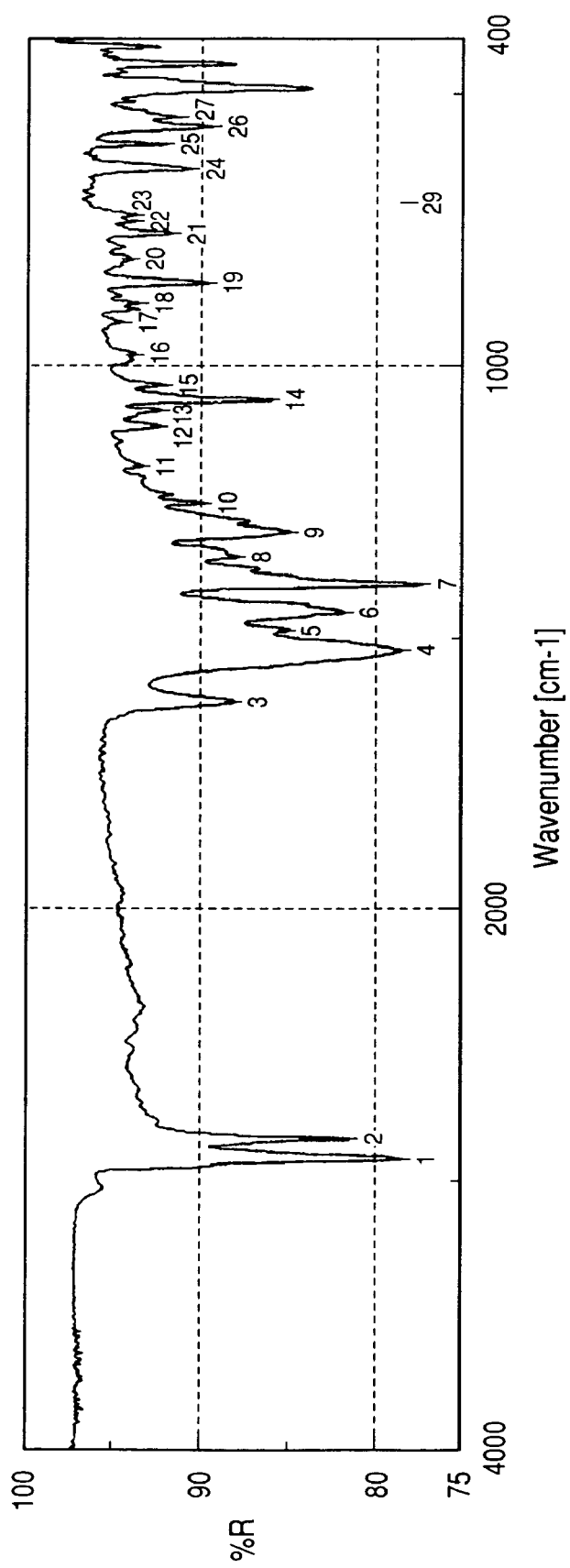
FIG. 43 shows a chart of infrared absorption spectrum (1R) of a crystal comprising (2R)-2-propyloctanoic acid and dicyclohexylamine.
Figure 44:
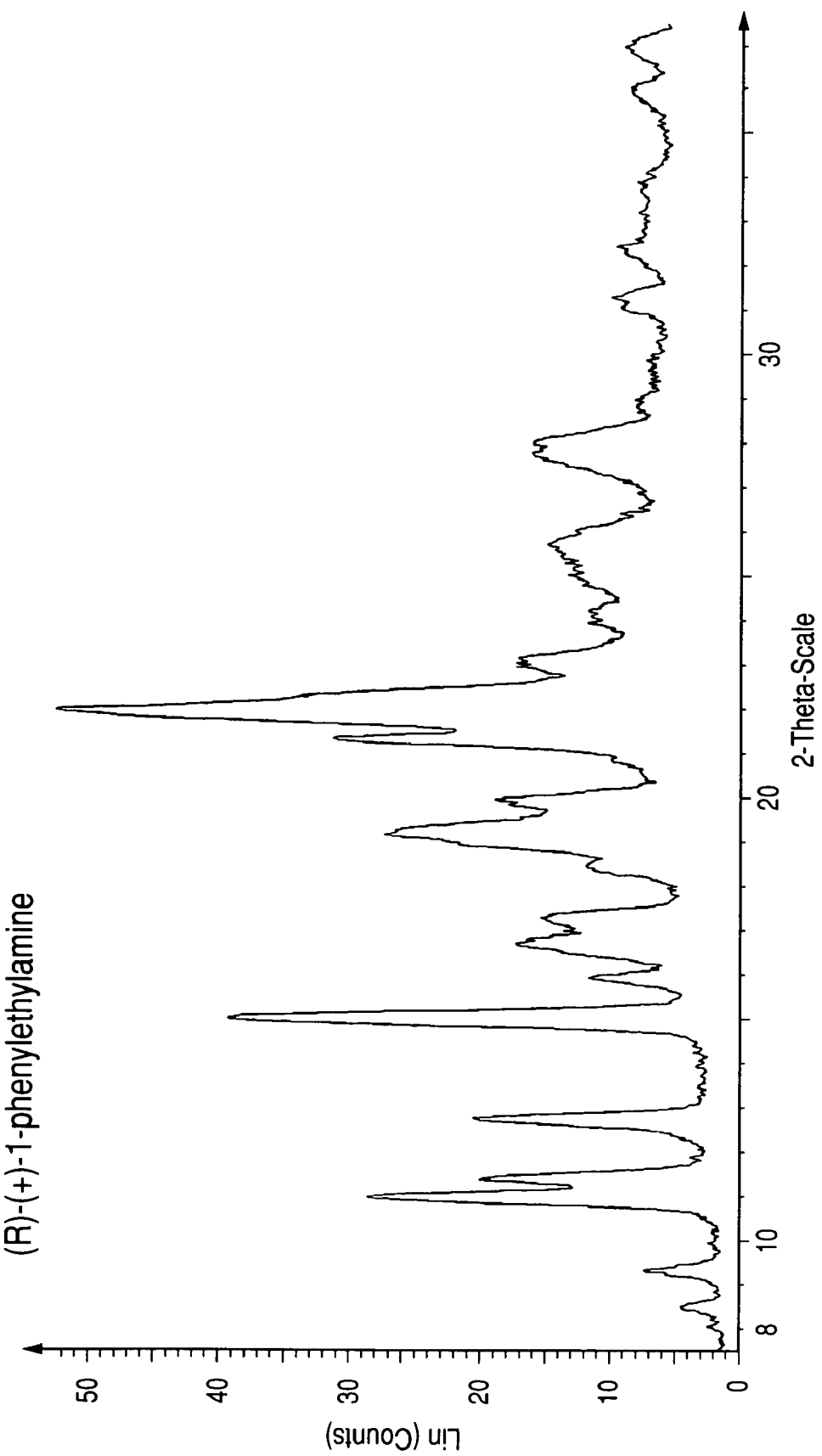
FIG. 44 shows a chart of powdered X-ray diffraction spectrum of a crystal comprising (2R)-2-propyloctanoic acid and (R)-(+)-1-phenylethylamine.
Figure 45:
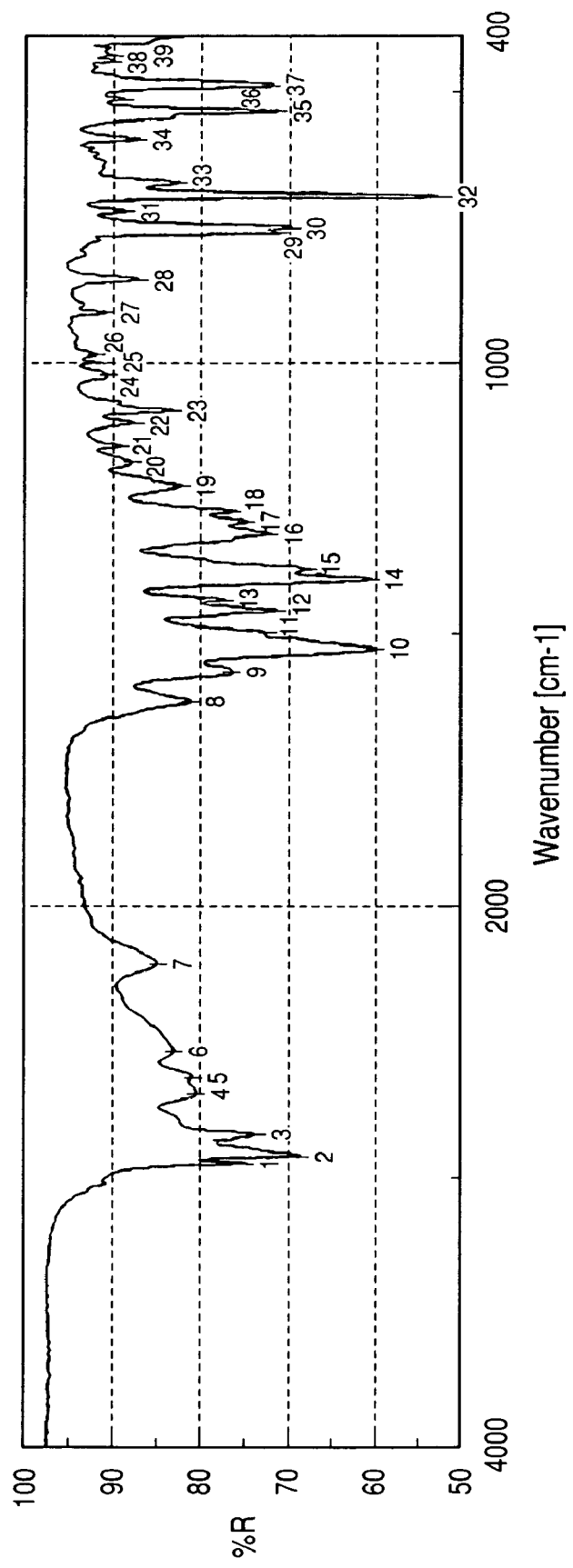
FIG. 45 shows a chart of infrared absorption spectrum (1R) of a crystal comprising (2R)-2-propyloctanoic acid and (R)-(+)-1-phenylethylamine.
Figure 46:
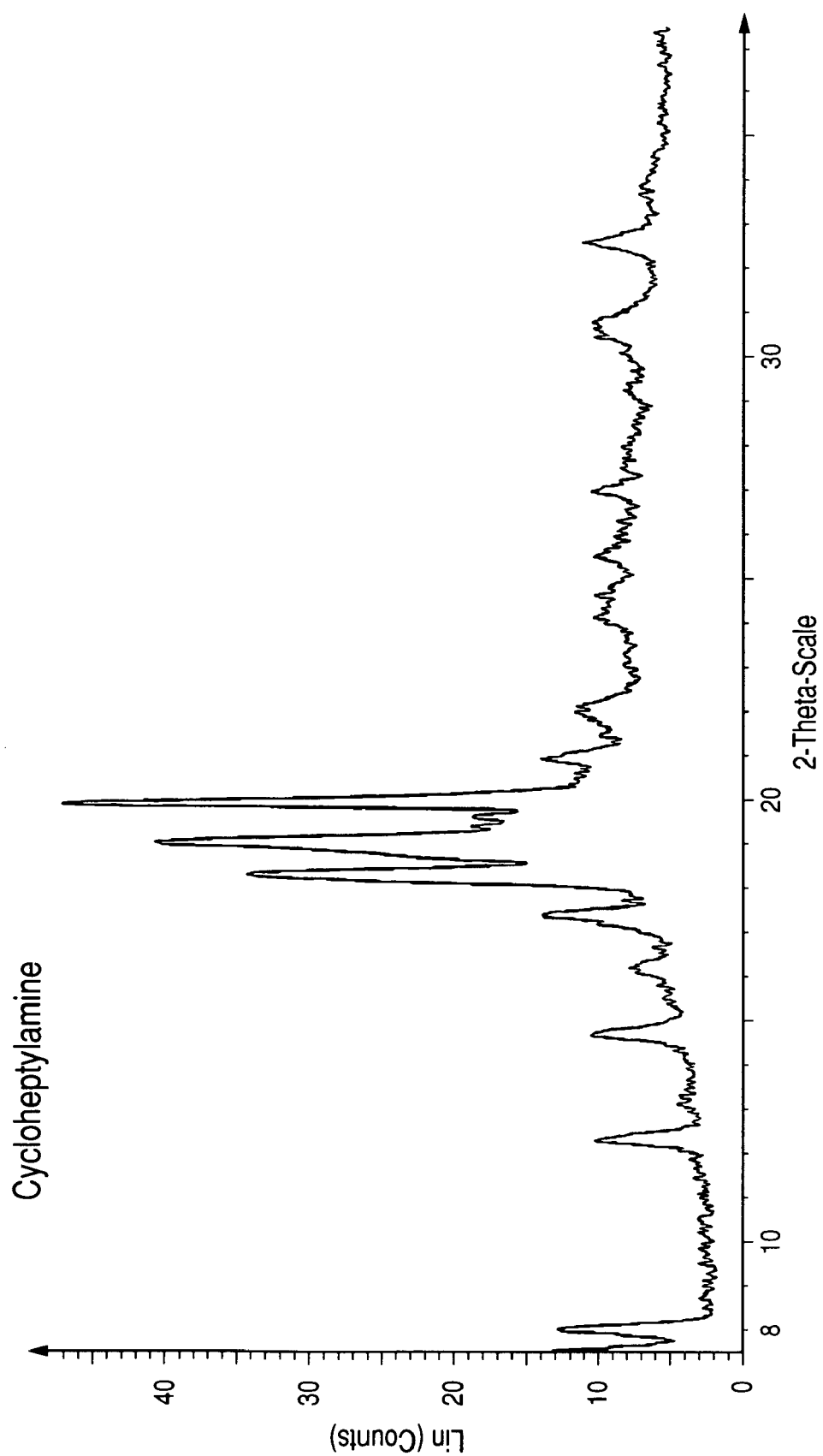
FIG. 46 shows a chart of powdered X-ray diffraction spectrum of a crystal comprising (2R)-2-propyloctanoic acid and cycloheptylamine.
Figure 47:
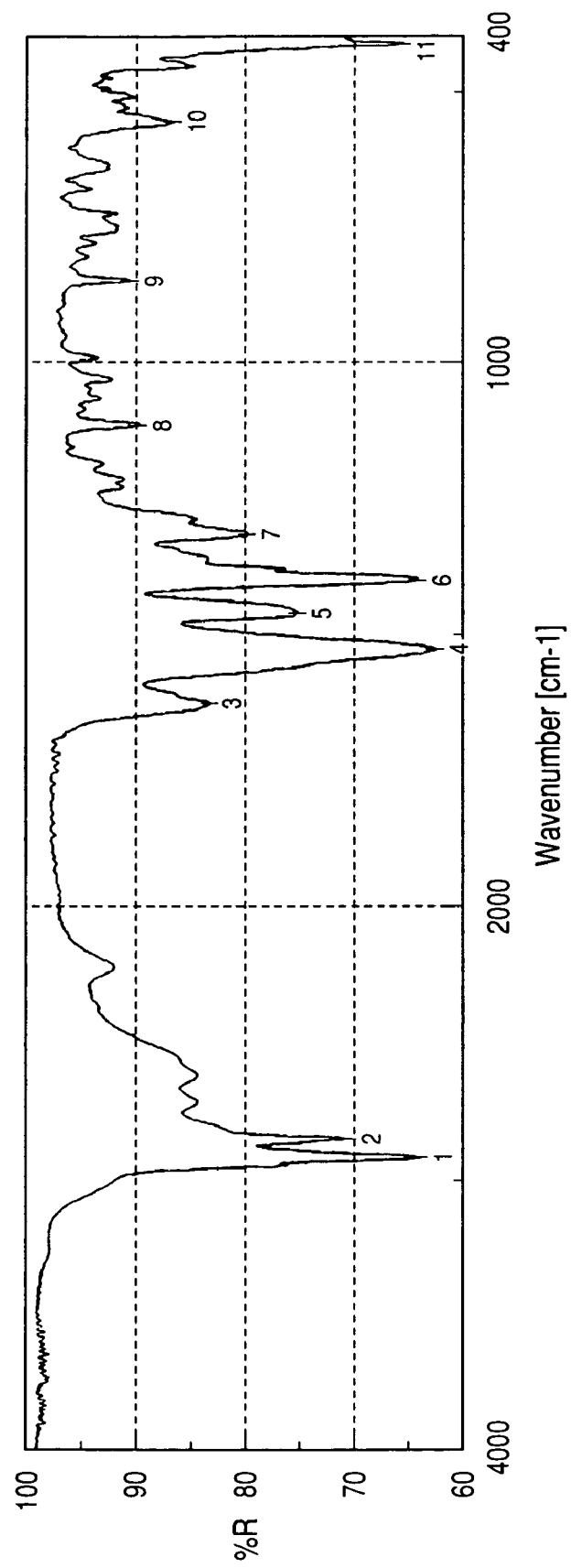
FIG. 47 shows a chart of infrared absorption spectrum (1R) of a crystal comprising (2R)-2-propyloctanoic acid and cycloheptylamine.
Figure 48:
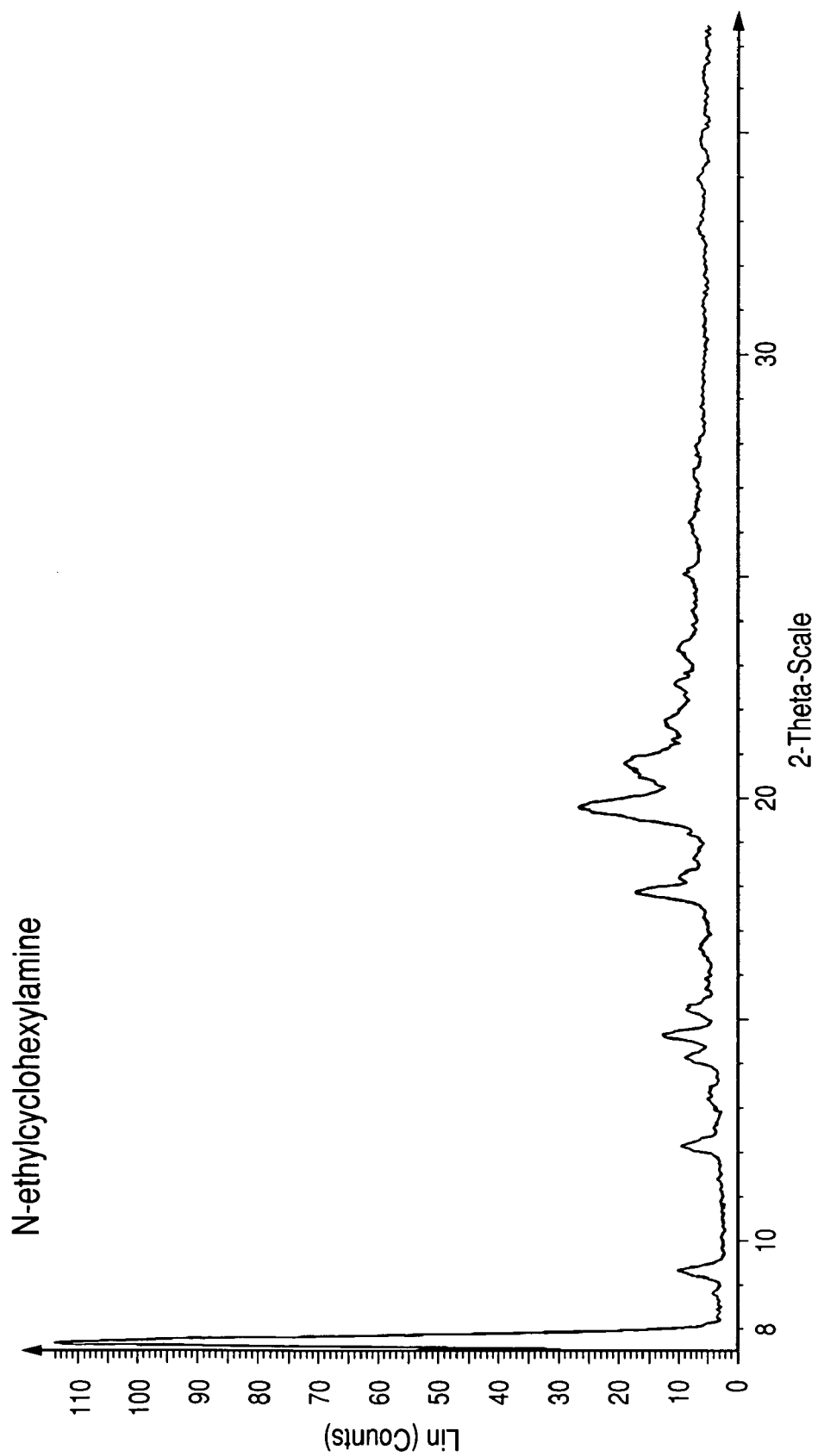
FIG. 48 shows a chart of powdered X-ray diffraction spectrum of a crystal comprising (2R)-2-propyloctanoic acid and N-ethylcyclohexylamine.
Figure 49:
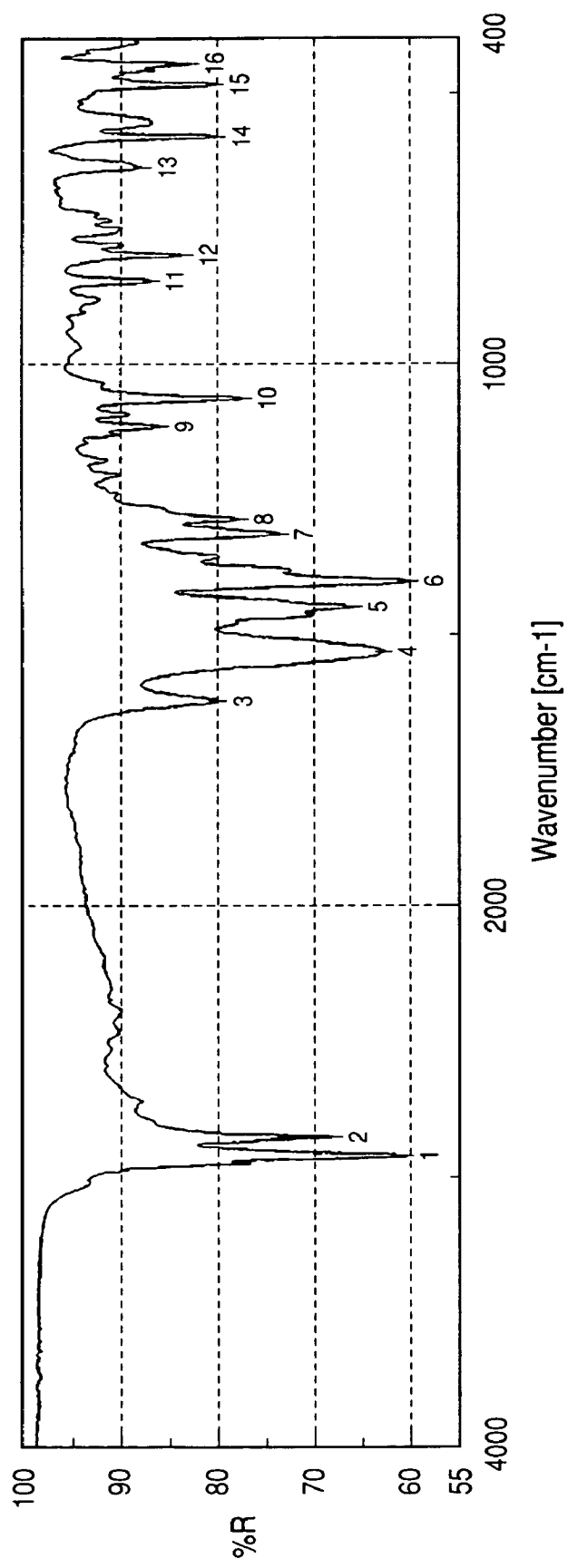
FIG. 49 shows a chart of infrared absorption spectrum (1R) of a crystal comprising (2R)-2-propyloctanoic acid and N-ethylcyclohexylamine.
Figure 50:
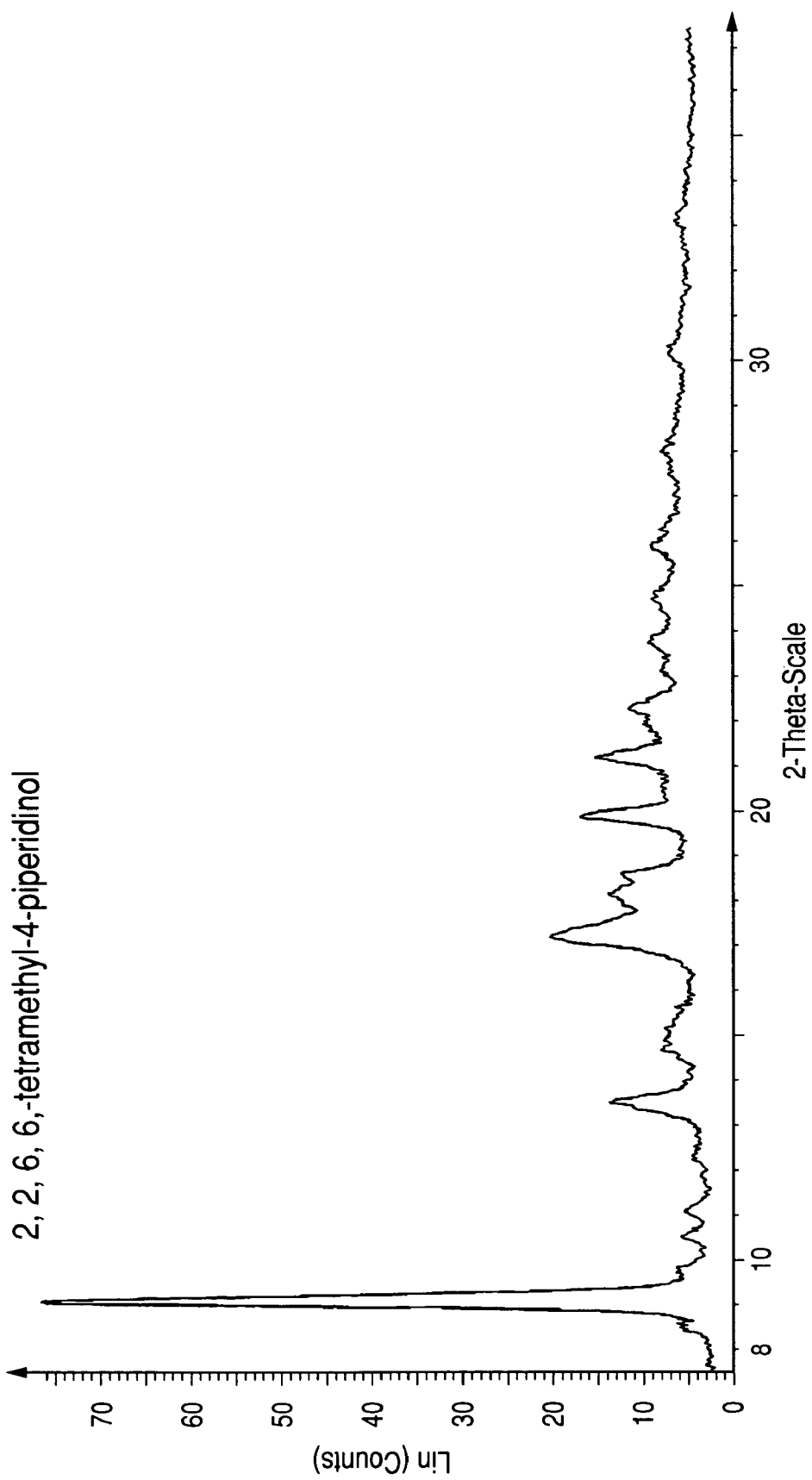
FIG. 50 shows a chart of powdered X-ray diffraction spectrum of a crystal comprising (2R)-2-propyloctanoic acid and 2,2,6,6-tetramethyl-4-piperidinol.
Figure 51:
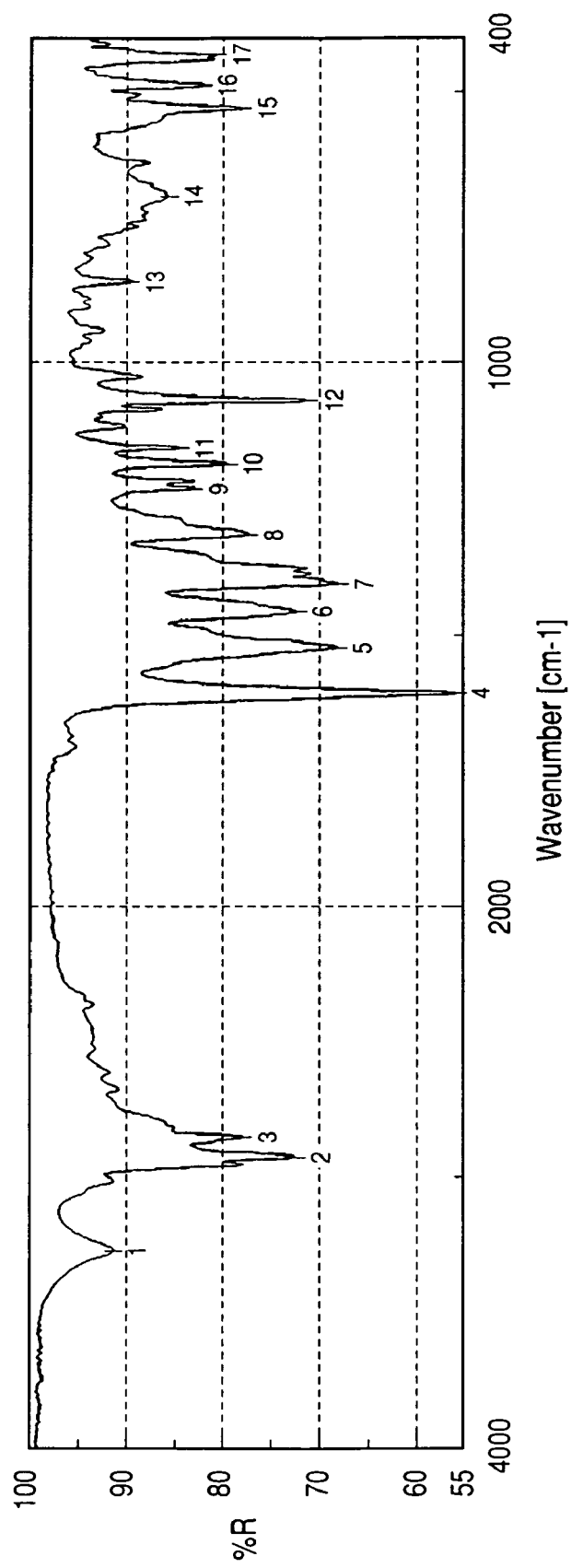
FIG. 51 shows a chart of infrared absorption spectrum (1R) of a crystal comprising (2R)-2-propyloctanoic acid and 2,2,6,6-tetramethyl-4-piperidinol.
Figure 52:
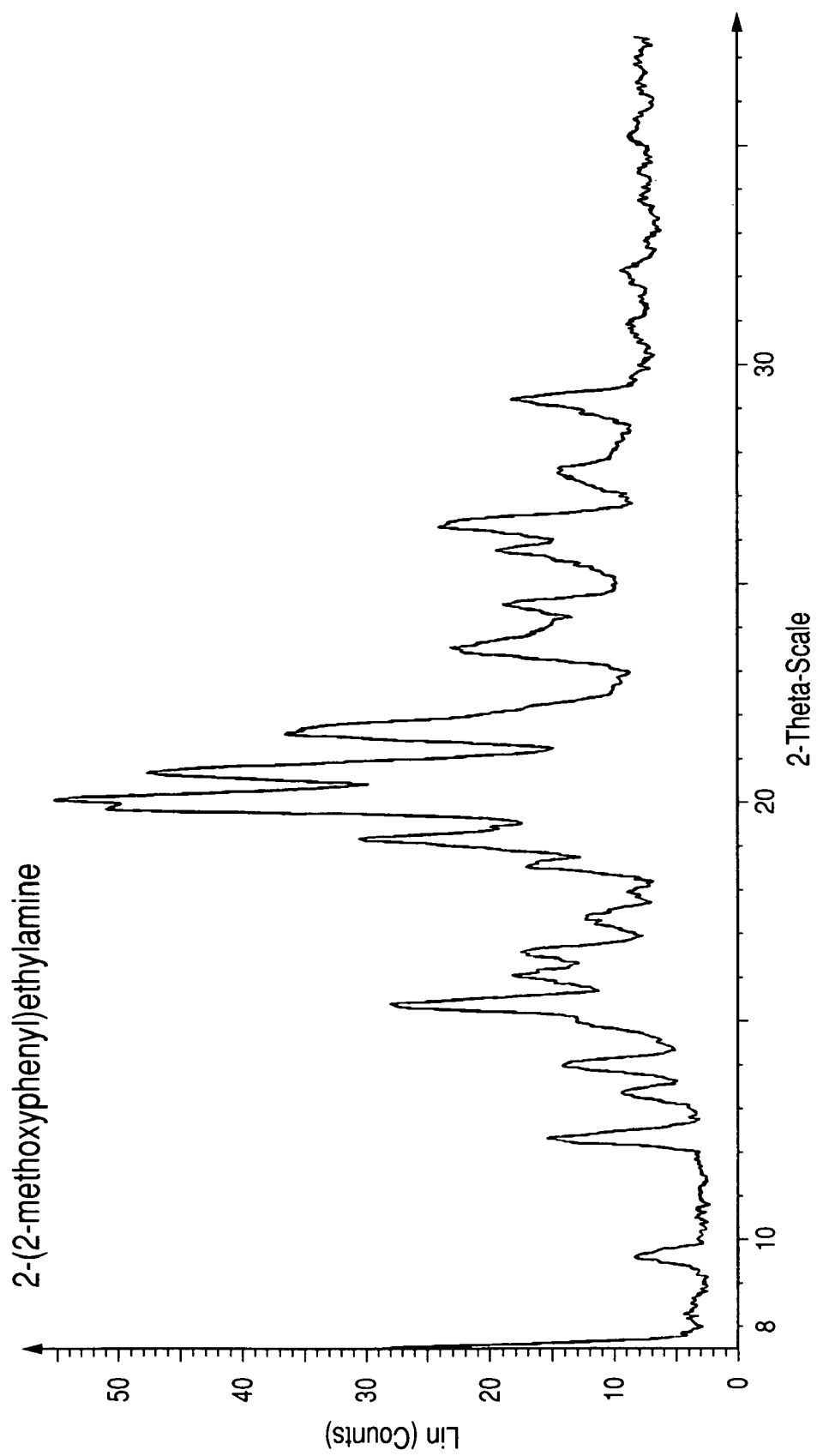
FIG. 52 shows a chart of powdered X-ray diffraction spectrum of a crystal comprising (2R)-2-propyloctanoic acid and 2-(2-methoxyphenyl)ethylamine.
Figure 53:
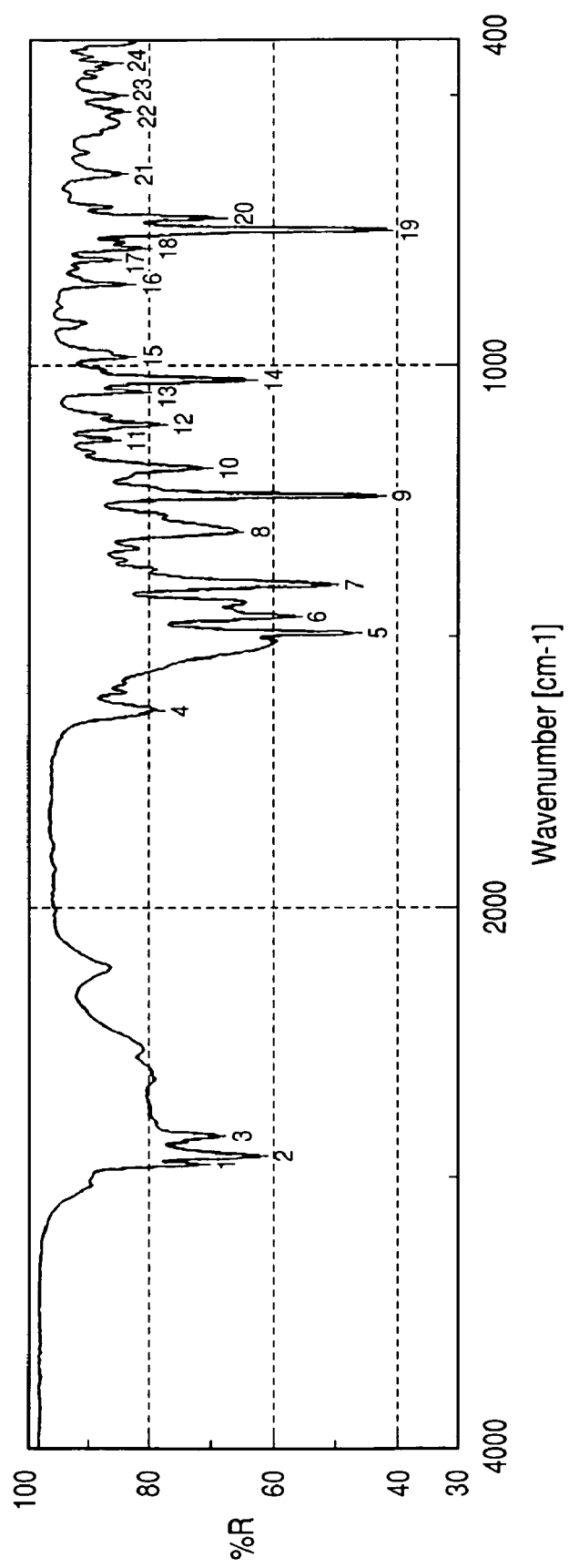
FIG. 53 shows a chart of infrared absorption spectrum (1R) of a crystal comprising (2R)-2-propyloctanoic acid and 2-(2-methoxyphenyl)ethylamine.
Figure 54:
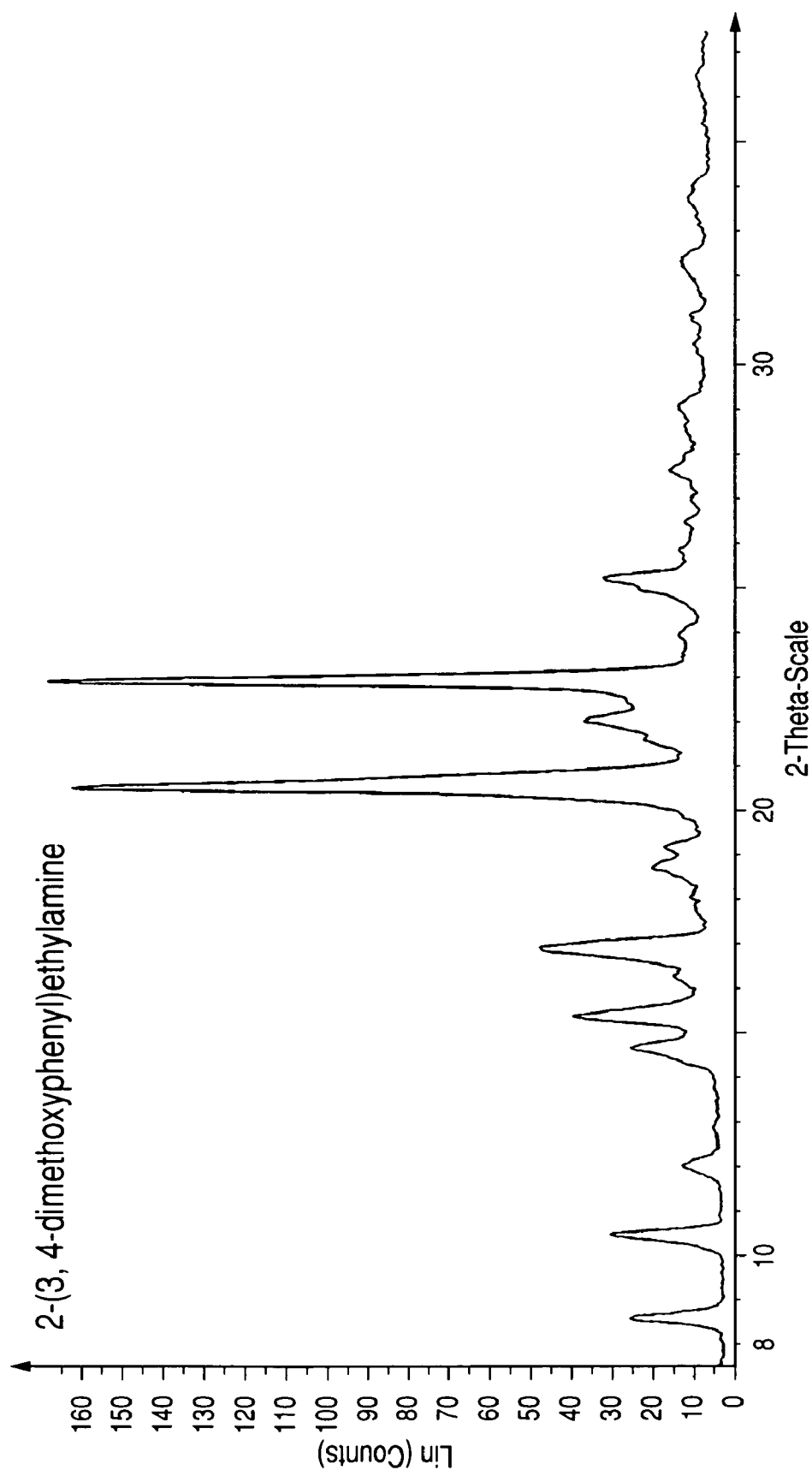
FIG. 54 shows a chart of powdered X-ray diffraction spectrum of a crystal comprising (2R)-2-propyloctanoic acid and 2-(3,4-dimethoxyphenyl)ethylamine.
Figure 55:
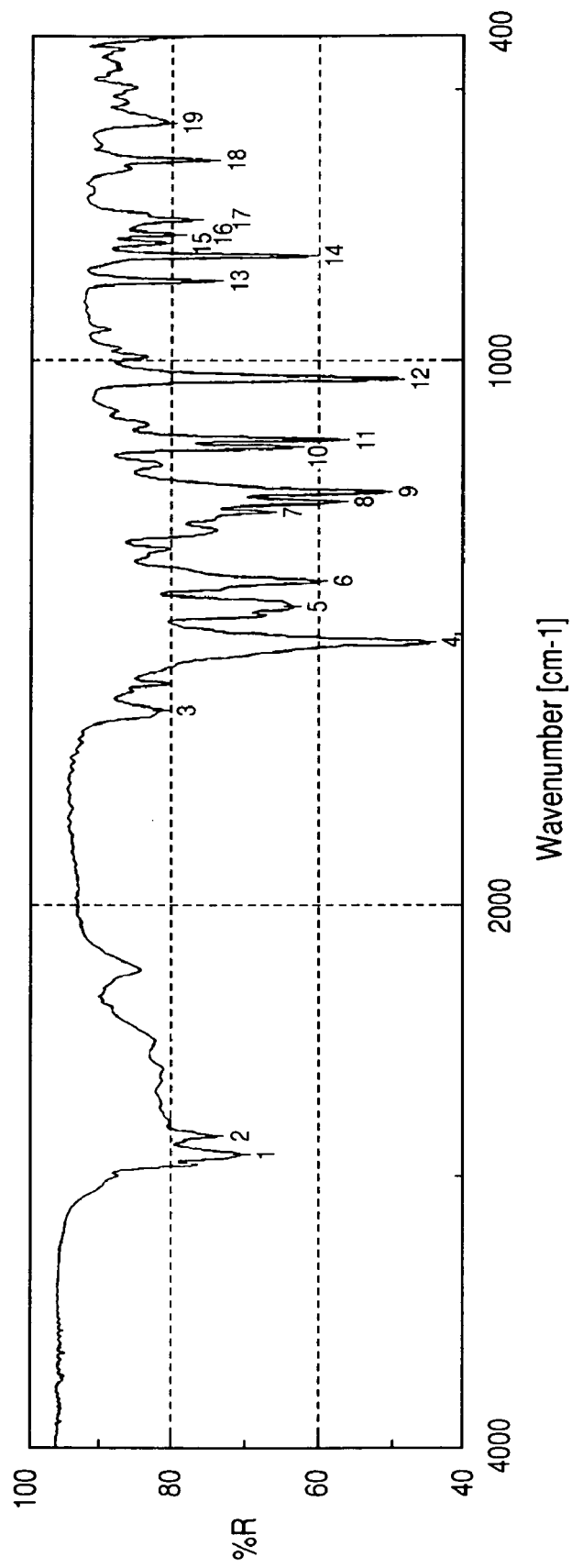
FIG. 55 shows a chart of infrared absorption spectrum (1R) of a crystal comprising (2R)-2-propyloctanoic acid and 2-(3,4-dimethoxyphenyl)ethylamine.
Figure 56:
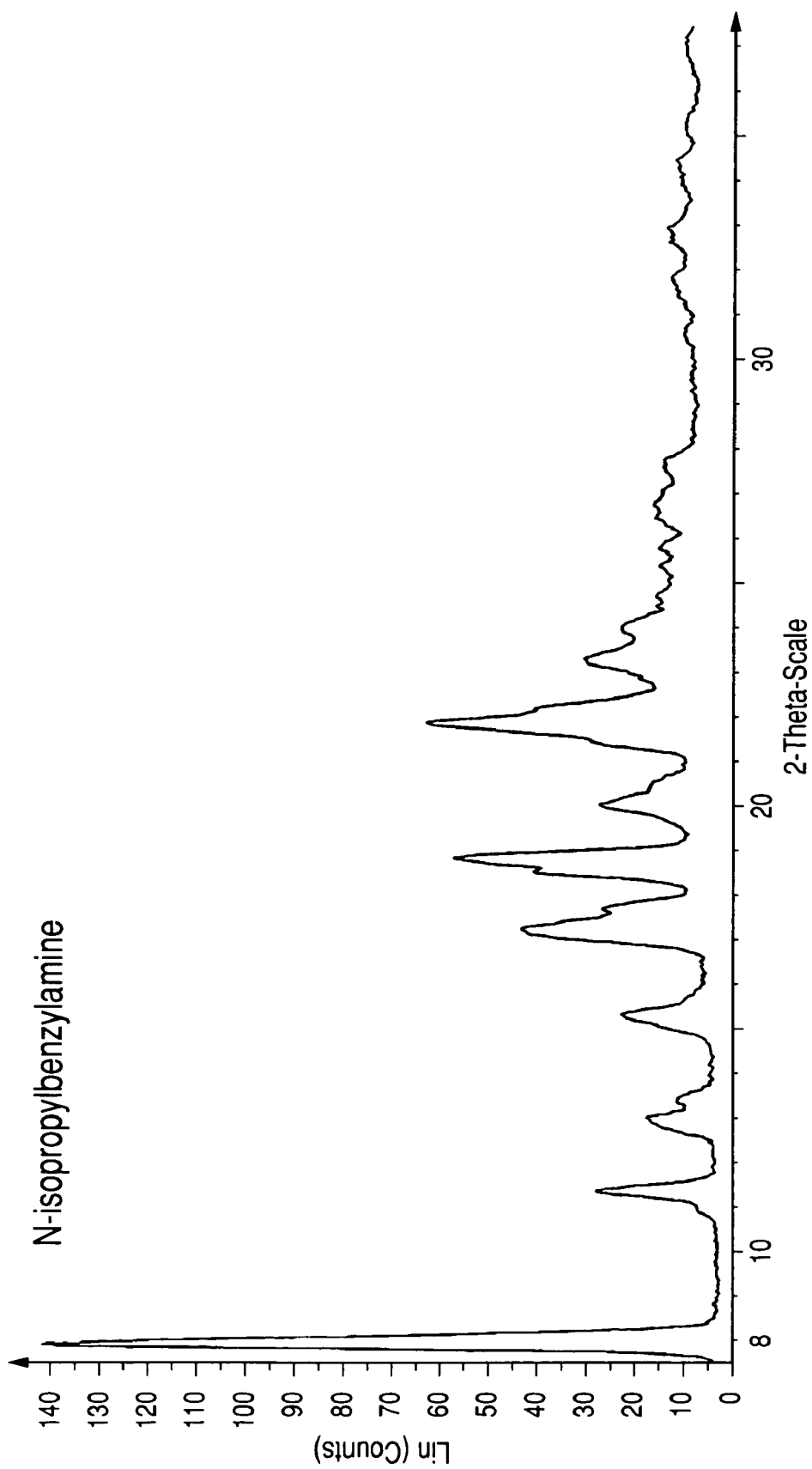
FIG. 56 shows a chart of powdered X-ray diffraction spectrum of a crystal comprising (2R)-2-propyloctanoic acid and N-isopropylbenzylamine.
Figure 57:
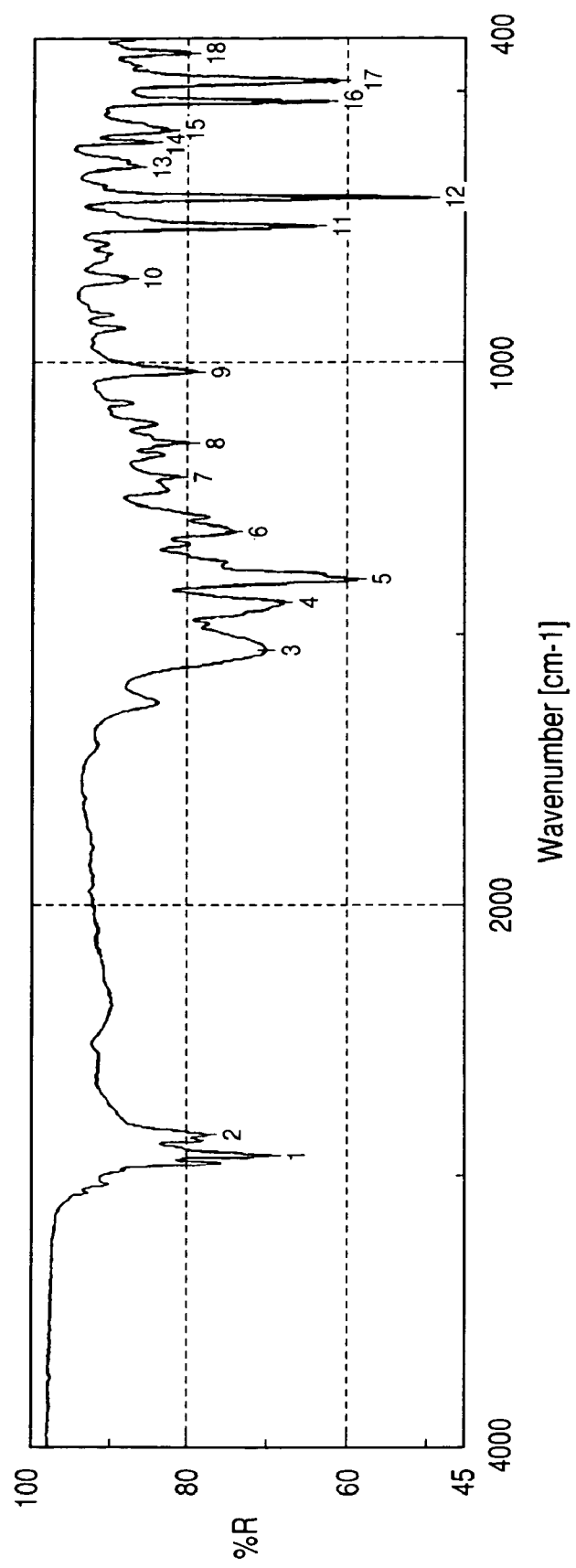
FIG. 57 shows a chart of infrared absorption spectrum (1R) of a crystal comprising (2R)-2-propyloctanoic acid and N-isopropylbenzylamine.
Figure 58:
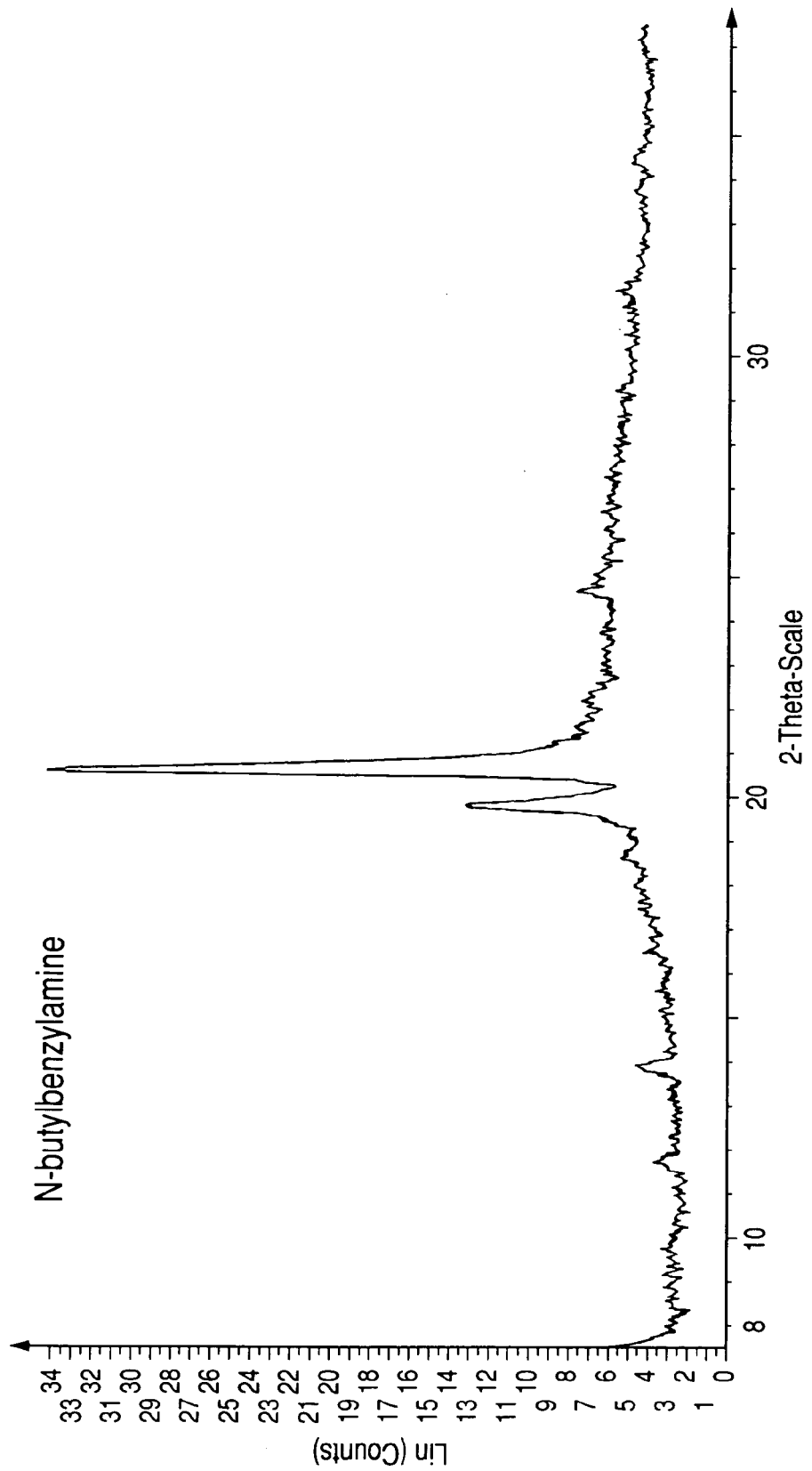
FIG. 58 shows a chart of powdered X-ray diffraction spectrum of a crystal comprising (2R)-2-propyloctanoic acid and N-butylbenzylamine.
Figure 59:
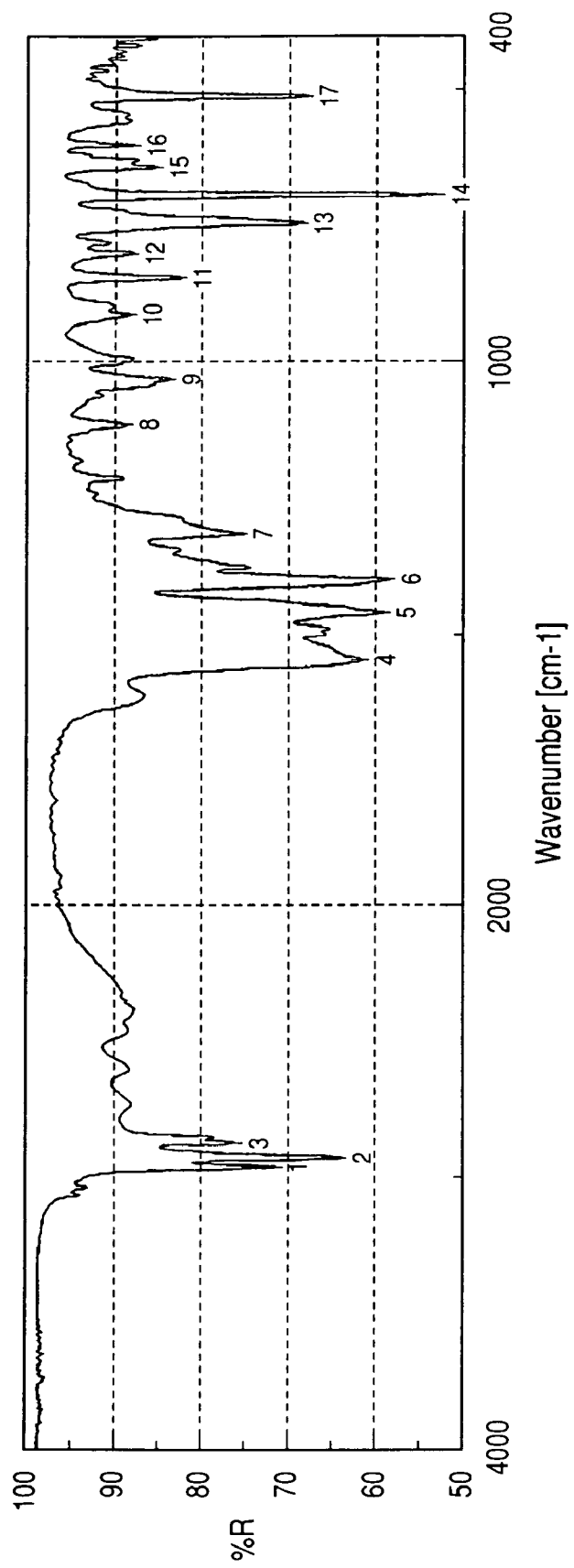
FIG. 59 shows a chart of infrared absorption spectrum (1R) of a crystal comprising (2R)-2-propyloctanoic acid and N-butylbenzylamine.
Figure 60:
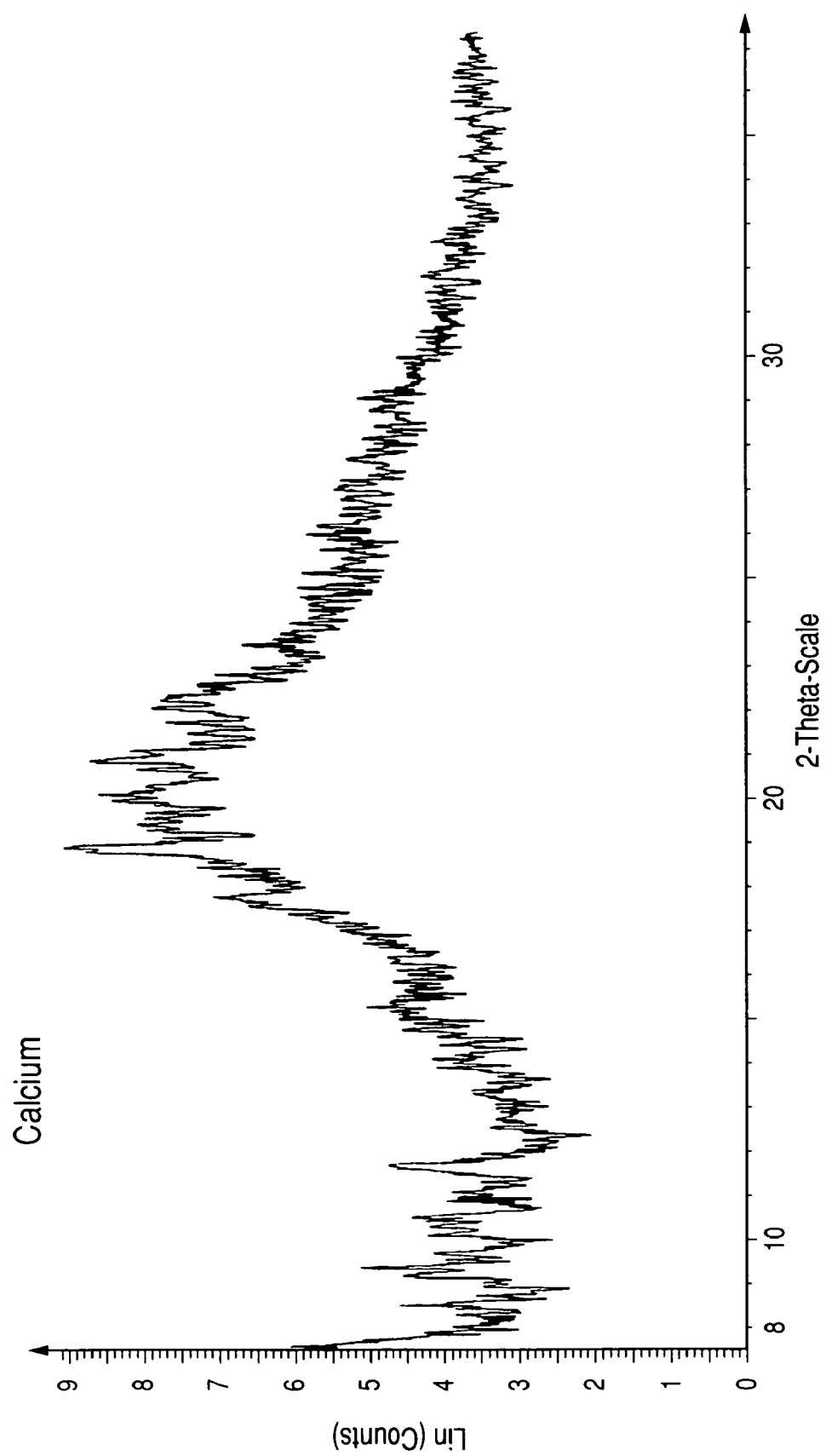
FIG. 60 shows a chart of powdered X-ray diffraction spectrum of calcium (2R)-2-propyloctanoate.

FIG. 26 shows the results.

TABLE 26

| Crystal with dibenzylamine | | |
| --- | --- | --- |
| Diffraction angle (2θ) (degree) | Half width (Å) | Relative intensity (%) |
| 15.27 | 5.80 | 64.9 |
| 17.03 | 5.20 | 34.5 |
| 19.04 | 4.66 | 100.0 |
| 19.99 | 4.44 | 85.7 |
| 21.36 | 4.16 | 25.8 |
| 22.91 | 3.88 | 80.4 |
| 24.21 | 3.67 | 89.1 |
| 26.09 | 3.41 | 30.7 |
| 26.70 | 3.34 | 28.9 |
| 28.42 | 3.14 | 23.8 |
| 30.83 | 2.90 | 24.6 |
| 34.06 | 2.63 | 22.3 |

[2] Infrared Absorption (IR) Spectrum

| <Measurement conditions> | |
| --- | --- |
| Apparatus: | JASCO Corporation, FTIR-660Plus/Sens IR TECHNOLOGIES, DuraScope |
| Method of Measurement: | measured by a KBr method |
| Resolution: | 4 cm$^{-1}$ |
| Frequency of scanning: | 16 times |

<Results>

IR (KBr method): 3434, 3068, 3036, 2957, 2926, 2872, 2853, 2756, 2621, 2454, 1948, 1638, 1498, 1466, 1457, 1415, 1379, 1342, 1321, 1212, 1141, 1112, 1096, 1044, 989, 936, 905, 812, 763, 744, 694 cm$^{-1}$.

[3] Differential Scanning Calorimetry (DSC)

| <Measurement conditions> | |
| --- | --- |
| Apparatus: | METTLER TOLEDO, DSC822e |
| Amount of Sample: | 1.15 mg |
| Sample Cell: | Aluminum open cell |
| Flow Rate of Argon Gas: | 40 mL/min |
| Programming Rate: | 5° C./min |

<Results>

Endothermic peak was found at approximately 81.8° C.

[4] Elemental Analysis

<Results>

Anal. Calcd for $C_{36}H_{59}N$: C, 75.88; H, 10.44; N, 2.46; Found: C, 75.78; H, 10.25; N, 2.50.

[5] Specific Optical Rotation

<Results>

$[\alpha]_D^{20}$=−3.6° (c=2.00, ethanol).

EXAMPLE 2

(2R)-2-propyloctanoic acid

Under an argon atmosphere, aqueous 1N-potassium hydroxide solution (400 mL) was added to the compound (100 g) produced in Example 1 at about 20° C. (inner temperature), and the mixture was stirred for about 10 minutes. This solution was back-extracted with isopropyl acetate (250mL×2). The resulting aqueous layer was extracted with addition of a mixture of n-heptane: isopropyl acetate (1:1) (500 mL) and conc. hydrochloric acid (40 mL). The resulting organic layer was washed with water (200 mL) and saturated brine (200 mL) in order and concentrated. The resulting residue was purified by distillation to give the compound of the present invention having the following physicochemical properties (63.5 g [100 area %], 99.8% e.e.; yield 97%).

The optical purity was determined by liquid chromatography after conversion into the phenacyl ester.

TLC: Rf 0.54 (hexane:ethyl acetate=7:3);

NMR (CDCl$_3$): δ 0.86-0.93 (m, 6H), 1.25-1.50 (m, 2H), 2.36 (m, 1H);

IR (liquid film method): 2958, 2930, 2859, 2360, 1706, 1466, 1417, 1381, 1289, 1254, 1216, 1110, 943, 565 cm$^{-1}$.

In this connection, in (2R)-2-propyloctanoic acid obtained from (2R)-2-propyloctanoic acid of optical purity 99.0% e.e. through the same operation as that from Example 1 to Example 2, the optical purity was 99.6% e.e., and the specific rotation was $[\alpha]_D^{20}=-6.2°$ (c=2.0; ethanol).

EXAMPLE 3

Crystal Comprising (2R)-2-propyloctanoic acid and dibenzylamine

Using a variety of solvent in place of acetonitrile, the same operation as in Example 1 was repeated to elucidate the yield of the title crystal. In addition, using those crystals, the same operation as in Example 2 was repeated to elucidate the optical purity of the resulting (2R)-2-propyloctanoic acid.

The following table shows the solvent used, the amount of the solvent used, yield and optical purity. The amount of the solvent used was represented by a volume ratio for the total weight of solute. In this examination, (2R)-2-propyloctanoic acid used as a starting material had 99.2% e.e. of optical purity.

TABLE 27

| Solvent | Solvent amount | Yield | Optical purity |
|---|---|---|---|
| acetonitrile | 10 | 95% | 99.6% e.e. |
| acetonitrile | 15 | 100% | 99.6% e.e. |
| acetonitrile | 20 | 95% | 99.7% e.e. |
| acetonitrile | 25 | 71% | 99.7% e.e. |
| acetonitrile:isopropyl alcohol = 50:1 | 15 | 85% | 99.7% e.e. |
| acetonitrile:water = 50:1 | 15 | 79% | 99.7% e.e. |
| dimethyl carbonate | | 34% | 99.8% e.e. |
| isopropyl alcohol:water = 1:1 | 10 | 71% | 99.7% e.e. |
| isopropyl alcohol:water = 1.5:1 | 10 | 50% | 99.7% e.e. |
| isopropyl alcohol:water = 1.2:1 | 10 | 54% | 99.8% e.e. |
| isopropyl alcohol:water = 1:1.2 | 10 | 83% | 99.6% e.e. |
| isopropyl alcohol:water = 1:1.5 | 10 | 96% | 99.5% e.e. |
| isopropyl alcohol:water = 1:2 | 10 | 100% | 99.4% e.e. |
| isopropyl alcohol:water = 5.1:3.5 | 8.6 | 41% | 99.8% e.e. |
| methanol:water = 5.5:2.5 | 8 | 41% | 99.8% e.e. |
| ethanol:water = 5.3:3.5 | 8.8 | 46% | 99.8% e.e. |
| dimethoxyethane:water = 5:3 | 8 | 100% | 99.3% e.e. |

<Results>

It was found that the use of the crystal comprising (2R)-2-propyloctanoic acid and dibenzylamine as an intermediate for producing optically highly pure (2R)-2-propyloctanoic acid gives (2R)-2-propyloctanoic acid having the optical purity of over 99.5% e.e., efficiently.

EXAMPLES 4(1)-4(27)

Using a variety of amines in place of dibenzylamine, the same operation as in Example 1 was repeated to give compounds having the following physicochemical properties. The resulting compounds of the present invention were crystals. In this example, the experiment was carried out in the presence or absence of a variety of solvents. The solvents used in crystallization are respectively described in each item (when no solvent was used, no solvent is indicated). The optical purity of (2R)-2-propyloctanoic acid used as a starting material in this experiment, was 95.0% e.e. in Examples 4(1)-4(16), 99.2% e.e. in Examples 4(17)-4(20), and 99.4% e.e. in Examples 4(21)-4(27).

Physicochemical Data of the Crystal:

For the compound produced in Example 4(1)-4(27), charts of powdered X-ray diffraction spectrum and charts of infrared absorption spectrum (IR) are shown in Figs. below. The condition of measurement was as follows.

[1] Powdered X-ray Diffraction Spectrum

| <Measurement conditions> | |
|---|---|
| Apparatus: | BRUKER axs, BRUKER D8 DISCOVER with GADD(C2) |
| Target: | Cu |
| Filter: | none |
| Voltage: | 40 kV |
| Current: | 40 mA |
| Time of Exposure: | 5 min |

[2] Infrared Absorption (IR) Spectrum

| <Measurement conditions> | |
|---|---|
| Apparatus: | JASCO Corporation, FTIR-660Plus/Sens IR TECHNOLOGIES, DuraScope |
| Method of Measurement: | measured by an ATR method |
| Resolution: | 4 cm$^{-1}$ |
| Frequency of scanning: | 16 times |

EXAMPLE 4(1)

Crystal comprising (2R)-2-propyloctanoic acid and (+)-dehydroabietylamine

NMR (CDCl$_3$): δ 7.15 (11, d, J=8.0 Hz), 6.98 (1H, d, J=9.6 Hz), 6.88 (11, brs), 2.91-2.77 (3H, m), 2.60 (2H, brs), 2.27 (2H, m), 1.78-1.20 (31H, m), 0.94-0.84 (9H, m);

Melting point: 118.4-122.0° C.;

Powder X-Ray Diffraction Spectral Data:

TABLE 28

Crystal with (+)-dehydroabietylamine

| Diffraction angle (2θ) (degree) | Half width (Å) | Relative intensity (%) |
|---|---|---|
| 12.16 | 7.27 | 15.2 |
| 12.90 | 6.86 | 14.2 |
| 14.04 | 6.30 | 17.1 |
| 15.15 | 5.84 | 88.6 |
| 15.70 | 5.64 | 40.2 |
| 16.46 | 5.38 | 32.4 |
| 17.08 | 5.19 | 63.7 |
| 18.35 | 4.83 | 100.0 |
| 18.96 | 4.68 | 44.3 |
| 19.45 | 4.56 | 44.2 |
| 20.56 | 4.32 | 67.1 |
| 22.31 | 3.98 | 26.9 |
| 23.35 | 3.81 | 25.5 |
| 24.44 | 3.64 | 37.5 |
| 25.65 | 3.47 | 24.8 |

IR (ATR method): 2954, 2925, 2850, 2663, 2197, 1560, 1534, 1497, 1456, 1436, 1394, 1360, 1298, 1210, 1173, 1147, 1109, 1056, 1005, 911, 883, 854, 822, 777, 752, 726, 674, 630 cm$^{-1}$;

Solvent: a mixed solvent of methanol and water, a mixed solvent of ethanol and water, isopropyl alcohol, acetone,

EXAMPLE 4(2)

Crystal comprising (2R)-2-propyloctanoic acid and (R)-(−)-2-phenylglycinol

NMR (CDCl$_3$): δ 7.38-7.28 (5H, m), 4.15 (1H, dd, J=4.4, 8.8 Hz), 3.78 (1H, dd, J=4.4, 11.6 Hz), 3.67 (1H, dd, J=8.8, 11.6 Hz), 2.28 (1H, m), 1.62-1.23 (14H, m), 0.89 (3H, t, J=7.2 Hz), 0.87 (3H, t, J=6.8 Hz);

Melting point: 82.8-83.6° C.;

IR (ATR method): 3034, 2953, 2926, 2854, 2668, 2509, 2143, 1640, 1605, 1522, 1457, 1400, 1376, 1339, 1316, 1281, 1228, 1207, 1186, 1119, 1065, 1049, 994, 919, 891, 854, 787, 758, 700, 537 cm$^{-1}$;

Solvent: isopropyl alcohol, acetonitrile, ethyl acetate, diethyl carbonate, toluene, methyl t-butyl ether, n-hexane, diethyleneglycol dimethyl ether.

EXAMPLE 4(3)

Crystal comprising (2R)-2-propyloctanoic acid and (S)-(+)-2-phenylglycinol

NMR (CDCl$_3$): δ 7.38-7.22 (5H, m), 4.15 (1H, dd, J=4.0, 8.4 Hz), 3.78 (11, dd, J=4.0, 11.2 Hz), 3.66 (1H, dd, J=8.4, 11.2 Hz), 2.28 (1H, m), 1.62-1.19 (14H, m), 0.90 (3H, t, J=7.2), 0.87 (3H, t, J=7.2);

Melting point: 86.1-86.7° C.;

IR (ATR method): 3033, 2953, 2925, 2870, 2850, 2670, 2516, 2155, 1641, 1567, 1524, 1496, 1457, 1433, 1393, 1308, 1208, 1182, 1149, 1112, 1067, 1054, 1030, 1000, 920, 893, 860, 801, 758, 701 cm$^{-1}$;

Solvent: acetonitrile, ethyl acetate, diethyl carbonate, methyl t-butyl ether, n-hexane.

EXAMPLE 4(4)

Crystal comprising (2R)-2-propyloctanoic acid and (−)-cis-myrtanylamine

NMR (CDCl$_3$): δ 2.77 (2H, d, J=7.2 Hz), 2.36 (1H, m), 2.21 (2H, m), 2.04-1.85 (5H, m), 1.59-1.21 (161H, m), 0.97 (3H, s), 0.93-0.86 (9H, m);

Melting point: 70.3-73.2° C.;

Powder X-ray Diffraction Spectral Data:

TABLE 29

| Crystal with (−)-cis-myrtanylamine | | |
|---|---|---|
| Diffraction angle (2θ) (degree) | Half width (Å) | Relative intensity (%) |
| 11.23 | 7.88 | 6.3 |
| 14.53 | 6.09 | 19.6 |
| 15.43 | 5.74 | 21.4 |
| 16.55 | 5.35 | 87.6 |
| 17.74 | 5.00 | 100.0 |
| 18.71 | 4.74 | 56.0 |
| 19.57 | 4.53 | 56.4 |
| 21.44 | 4.14 | 45.9 |
| 22.45 | 3.96 | 22.2 |
| 23.29 | 3.82 | 11.2 |
| 24.45 | 3.64 | 16.1 |
| 25.60 | 3.48 | 18.7 |

TABLE 29-continued

| Crystal with (−)-cis-myrtanylamine | | |
|---|---|---|
| Diffraction angle (2θ) (degree) | Half width (Å) | Relative intensity (%) |
| 26.57 | 3.35 | 14.1 |
| 27.20 | 3.28 | 16.4 |
| 27.50 | 3.24 | 16.0 |
| 29.74 | 3.00 | 13.6 |
| 31.20 | 2.86 | 16.1 |
| 32.92 | 2.72 | 12.6 |
| 34.22 | 2.62 | 12.1 |
| 35.79 | 2.51 | 8.7 |
| 36.59 | 2.45 | 9.7 |

IR (ATR method): 2989, 2952, 2919, 2869, 2852, 2611, 2196, 1626, 1517, 1458, 1397, 1363, 1320, 1230, 1214, 1139, 1116, 1035, 1005, 978, 919, 874, 848, 809, 779, 747, 721, 637 cm$^{-1}$;

Solvent: acetonitrile, ethyl acetate, diethyl carbonate, toluene, methyl t-butyl ether, n-hexane.

EXAMPLE 4(5)

Crystal comprising (2R)-2-propyloctanoic acid and (R)-(+)-1-(p-tolyl)ethylamine

NMR (CDCl$_3$): δ 7.26-7.13 (4H, m), 4.14 (1H, q, J=6.4 Hz), 2.33 (3H, s), 2.26 (1H, m), 1.61-1.20 (17H, m), 0.91-0.85 (6H, m);

Melting point: 86.3-87.3° C.;

Powder X-ray Diffraction Spectral Data:

TABLE 30

| Crystal with (R)-(+)-1-(p-tolyl)ethylamine | | |
|---|---|---|
| Diffraction angle (2θ) (degree) | Half width (Å) | Relative intensity (%) |
| 11.34 | 7.79 | 24.4 |
| 12.01 | 7.36 | 8.7 |
| 12.81 | 6.91 | 31.7 |
| 13.69 | 6.46 | 6.7 |
| 15.08 | 5.87 | 8.8 |
| 16.15 | 5.48 | 45.5 |
| 17.47 | 5.07 | 20.9 |
| 18.84 | 4.71 | 100.0 |
| 20.08 | 4.42 | 28.2 |
| 20.68 | 4.29 | 71.7 |
| 22.03 | 4.03 | 19.3 |
| 23.00 | 3.86 | 89.2 |
| 24.14 | 3.68 | 27.1 |
| 25.65 | 3.47 | 54.2 |
| 27.41 | 3.25 | 29.2 |
| 28.22 | 3.16 | 17.1 |
| 29.92 | 2.98 | 14.6 |
| 30.99 | 2.88 | 14.0 |
| 32.64 | 2.74 | 15.6 |
| 33.22 | 2.70 | 14.6 |
| 34.46 | 2.60 | 12.3 |

IR (ATR method): 2954, 2925, 2856, 2702, 2536, 2210, 1621, 1567, 1518, 1464, 1440, 1405, 1381, 1315, 1306, 1231, 1172, 1111, 1090, 1021, 993, 898, 868, 849, 813, 779, 744, 722, 685 cm$^{-1}$;

Solvent: a mixed solvent of methanol and water, a mixed solvent of acetone and water, acetonitrile, dimethoxyethane, ethyl acetate, diethyl carbonate, n-hexane.

EXAMPLE 4(6)

Crystal comprising (2R)-2-propyloctanoic acid and (R)-(+)-1-(1-naphthyl)ethylamine NMR (CDCl$_3$): δ 8.10 (1 μl, d, J=8.4 Hz), 7.88 (1H, d, J=8.4 Hz), 7.77 (1H, d, J=8.4 Hz), 7.63 (1 μl, d, J=6.8 Hz), 7.56-7.46 (3H, m), 5.04 (1H, q, J=6.8 Hz), 2.29 (1H m), 1.60 (3H, d, J=6.8 Hz), 1.61-1.26 (14H, m), 0.91-0.85 (6H, m);

Melting point: 73.4-76.7° C.;

Powder X-ray Diffraction Spectral Data:

TABLE 31

Crystal with (R)-(+)-1-(1-naphthyl)ethylamine

| Diffraction angle (2θ) (degree) | Half width (Å) | Relative intensity (%) |
|---|---|---|
| 10.97 | 8.06 | 14.4 |
| 13.38 | 6.61 | 58.1 |
| 15.84 | 5.59 | 48.9 |
| 16.91 | 5.24 | 31.0 |
| 17.67 | 5.02 | 40.8 |
| 19.31 | 4.59 | 54.2 |
| 20.46 | 4.34 | 34.3 |
| 21.52 | 4.13 | 43.2 |
| 22.21 | 4.00 | 100.0 |
| 23.49 | 3.78 | 67.5 |
| 24.41 | 3.64 | 24.2 |
| 25.11 | 3.54 | 24.1 |
| 26.78 | 3.33 | 22.7 |
| 28.12 | 3.17 | 14.7 |
| 28.96 | 3.08 | 21.3 |
| 31.28 | 2.86 | 20.6 |
| 33.79 | 2.65 | 13.8 |
| 35.87 | 2.50 | 12.9 |
| 36.77 | 2.44 | 12.4 |

IR (ATR method): 2952, 2924, 2854, 2759, 2582, 2180, 1629, 1571, 1509, 1467, 1454, 1433, 1402, 1389, 1378, 1335, 1305, 1275, 1253, 1231, 1173, 1110, 1076, 1004, 950, 900, 860, 801, 774 cm$^{-1}$;

Solvent: acetonitrile, n-hexane.

EXAMPLE 4(7)

Crystal comprising (2R)-2-propyloctanoic acid and (S)-(−)-1-(1-naphthyl)ethylamine NMR (CDCl$_3$): δ 8.12 (1H d, J=8.4 Hz), 7.88 (1H, d, J=8.4 Hz), 7.76 (1H, d, J=8.4 Hz), 7.63 (1H, d, J=7.2 Hz), 7.56-7.46 (3H m), 5.02 (1H, q, J=6.8 Hz), 2.32 (1H, m), 1.64-1.21 (17H, m), 0.92-0.85 (6H, m);

Melting point: 74.4-75.5° C.;

Powder X-ray Diffraction Spectral Data:

TABLE 32

Crystal with (S)-(−)-1-(1-naphthyl)ethylamine

| Diffraction angle (2θ) (degree) | Half width (Å) | Relative intensity (%) |
|---|---|---|
| 12.41 | 7.13 | 22.8 |
| 13.71 | 6.45 | 24.6 |
| 14.05 | 6.30 | 20.6 |
| 15.12 | 5.86 | 41.4 |

TABLE 32-continued

Crystal with (S)-(−)-1-(1-naphthyl)ethylamine

| Diffraction angle (2θ) (degree) | Half width (Å) | Relative intensity (%) |
|---|---|---|
| 16.27 | 5.45 | 35.1 |
| 16.80 | 5.27 | 54.0 |
| 17.57 | 5.04 | 57.3 |
| 18.72 | 4.74 | 53.3 |
| 19.35 | 4.58 | 94.0 |
| 19.96 | 4.45 | 57.4 |
| 21.00 | 4.23 | 74.1 |
| 21.50 | 4.13 | 57.6 |
| 22.41 | 3.96 | 100.0 |
| 23.56 | 3.77 | 27.5 |
| 23.95 | 3.71 | 28.0 |
| 25.55 | 3.48 | 49.7 |
| 26.21 | 3.40 | 41.1 |
| 27.79 | 3.21 | 32.9 |
| 28.56 | 3.12 | 25.9 |
| 30.92 | 2.89 | 26.0 |

IR (ATR method): 2952, 2922, 2850, 2219, 1624, 1601, 1557, 1514, 1467, 1454, 1395, 1377, 1317, 1279, 1223, 1177, 1108, 1075, 1030, 1002, 950, 923, 898, 860, 849, 799, 775, 749 cm$^{-1}$;

Solvent: acetonitrile, n-hexane.

EXAMPLE 4(8)

Crystal comprising (2R)-2-propyloctanoic acid and L-tyrosinamide

NMR (CDCl$_3$): δ 7.07 (2H, d, J=8.4 Hz), 6.74 (2H, d, J=8.4 Hz), 3.70 (11, dd, J=6.0, 8.0 Hz), 3.00 (1H, dd, J=6.0, 13.6 Hz), 2.80 (1H, dd, J=8.0, 13.6 Hz), 2.22 (1H, m), 1.59-1.22 (14K, m), 0.92-0.86 (6H, m);

Melting point: 109.3-111.1° C.;

Powder X-ray Diffraction Spectral Data:

TABLE 33

Crystal with L-tyrosinamide

| Diffraction angle (2θ) (degree) | Half width (Å) | Relative intensity (%) |
|---|---|---|
| 12.10 | 7.31 | 10.7 |
| 12.83 | 6.89 | 8.7 |
| 14.67 | 6.03 | 15.3 |
| 15.44 | 5.73 | 17.4 |
| 16.46 | 5.38 | 57.5 |
| 17.08 | 5.19 | 100.0 |
| 18.19 | 4.87 | 40.7 |
| 19.89 | 4.46 | 91.5 |
| 21.30 | 4.17 | 66.1 |
| 22.12 | 4.02 | 40.1 |
| 23.31 | 3.81 | 61.6 |
| 24.15 | 3.68 | 48.1 |
| 25.81 | 3.45 | 37.5 |
| 27.36 | 3.26 | 43.0 |
| 28.66 | 3.11 | 20.8 |
| 29.85 | 2.99 | 19.7 |
| 30.95 | 2.89 | 23.2 |
| 32.97 | 2.71 | 29.2 |
| 33.48 | 2.67 | 21.9 |
| 35.00 | 2.56 | 17.7 |
| 36.64 | 2.45 | 20.7 |

IR (ATR method): 3430, 2953, 2923, 2856, 1673, 1559, 1512, 1449, 1407, 1376, 1349, 1324, 1266, 1242, 1210, 1175, 1108, 1078, 1037, 997, 850, 830, 785, 736, 645 cm$^{-1}$;

Solvent: acetonitrile.

EXAMPLE 4(9)

Crystal comprising (2R)-2-propyloctanoic acid and (1S,2R)-(+)-2-amino-1,2-diphenylethanol NMR (CDCl$_3$): δ 7.32-7.18 (10×m), 4.85 (1H, d, J=6.0 Hz), 4.20 (11, d, J=6.0 Hz), 2.34 (1H, m), 1.66-1.22 (14H, m), 0.91 (31, t, J=7.2 Hz), 0.88 (31, t, J=6.8 Hz);

Melting point: 109.5-111.7° C.;

Powder X-ray Diffraction Spectral Data:

TABLE 34

Crystal with (1S,2R)-(+)-2-amino-1,2-diphenylethanol

| Diffraction angle (2θ) (degree) | Half width (Å) | Relative intensity (%) |
|---|---|---|
| 13.60 | 6.51 | 25.5 |
| 14.18 | 6.24 | 20.4 |
| 15.96 | 5.55 | 100.0 |
| 17.33 | 5.11 | 44.1 |
| 18.35 | 4.83 | 22.5 |
| 19.47 | 4.56 | 62.7 |
| 20.46 | 4.34 | 82.6 |
| 21.41 | 4.15 | 59.3 |
| 22.45 | 3.96 | 37.5 |
| 23.55 | 3.77 | 64.9 |
| 24.78 | 3.59 | 61.9 |
| 25.97 | 3.43 | 25.8 |
| 27.53 | 3.24 | 22.8 |
| 28.63 | 3.12 | 19.6 |
| 29.79 | 3.00 | 24.1 |
| 32.31 | 2.77 | 16.5 |
| 33.54 | 2.67 | 20.2 |
| 35.51 | 2.53 | 21.9 |

IR (ATR method): 2925, 2851, 1617, 1559, 1507, 1455, 1406, 1320, 1272, 1204, 1134, 1081, 1047, 1007, 919, 848, 782, 765, 742, 699, 567 cm$^{-1}$;

Solvent: a mixed solvent of methanol and water, a mixed solvent of ethanol and water, isopropyl alcohol, a mixed solvent of acetone and water, acetonitrile, dimethoxyethane, ethyl acetate, diethyl carbonate, toluene.

EXAMPLE 4(10)

Crystal comprising (2R)-2-propyloctanoic acid and (1R,2S)-(−)-2-amino-1,2-diphenylethanol NMR (CDCl$_3$): δ 7.32-7.18 (10H, m), 4.84 (11, d, J=6.0 Hz), 4.19 (11, d, J=6.0 Hz), 2.33 (1H, m), 1.65-1.22 (14H, m), 0.91 (3H, t, J=7.2 Hz), 0.88 (3H, t, J=7.2 Hz);

Melting point: 110.8-112.8° C.;

Powder X-ray Diffraction Spectral Data:

TABLE 35

Crystal with (1R,2S)-(−)-2-amino-1,2-diphenylethanol

| Diffraction angle (2θ) (degree) | Half width (Å) | Relative intensity (%) |
|---|---|---|
| 10.06 | 8.79 | 8.9 |
| 11.94 | 7.41 | 21.5 |
| 12.88 | 6.87 | 8.8 |
| 15.11 | 5.86 | 37.0 |
| 15.97 | 5.54 | 73.4 |
| 16.52 | 5.36 | 44.3 |
| 17.91 | 4.95 | 89.4 |
| 19.15 | 4.63 | 55.9 |
| 19.77 | 4.49 | 80.0 |

TABLE 35-continued

Crystal with (1R,2S)-(−)-2-amino-1,2-diphenylethanol

| Diffraction angle (2θ) (degree) | Half width (Å) | Relative intensity (%) |
|---|---|---|
| 21.29 | 4.17 | 83.6 |
| 23.04 | 3.86 | 100.0 |
| 24.07 | 3.69 | 36.8 |
| 25.40 | 3.50 | 59.4 |
| 25.76 | 3.46 | 58.2 |
| 28.44 | 3.14 | 27.0 |
| 29.57 | 3.02 | 23.2 |
| 30.70 | 2.91 | 27.4 |
| 35.72 | 2.51 | 26.0 |

IR (ATR method): 3275, 2953, 2925, 2856, 2605, 1617, 1560, 1542, 1508, 1455, 1408, 1307, 1277, 1239, 1205, 1132, 1110, 1081, 1046, 1006, 921, 907, 849, 811, 783, 765, 742, 700 cm$^{-1}$;

Solvent: a mixed solvent of methanol and water, a mixed solvent of ethanol and water, isopropyl alcohol, a mixed solvent of acetone and water, acetonitrile, dimethoxyethane, ethyl acetate, diethyl carbonate, toluene.

EXAMPLE 4(11)

Crystal comprising (2R)-2-propyloctanoic acid and (+)-cis-2-benzylaminocyclohexanemethanol NMR (CDCl$_3$): δ 7.37-7.27 (5H, m), 4.05-3.90 (3H, m), 3.69 (1H, dd, J=3.2, 11.2 Hz), 3.05 (1H, m), 2.26 (1-m), 2.22 (1H, m), 2.16 (1H, m), 1.87 (1H, m), 1.68-1.21 (21H, m), 0.90 (31, t, J=7.2 Hz), 0.87 (311, t, J=6.8 Hz);

Melting point: 64.6-67.0° C.;

Powder X-ray Diffraction Spectral Data:

TABLE 36

Crystal with (+)-cis-2-benzylaminocyclohexanemethanol

| Diffraction angle (2θ) (degree) | Half width (Å) | Relative intensity (%) |
|---|---|---|
| 10.49 | 8.43 | 6.5 |
| 12.01 | 7.36 | 9.8 |
| 13.37 | 6.62 | 5.2 |
| 15.92 | 5.56 | 14.1 |
| 16.68 | 5.31 | 18.7 |
| 17.90 | 4.95 | 100.0 |
| 19.83 | 4.47 | 28.8 |
| 21.16 | 4.20 | 34.2 |
| 22.75 | 3.91 | 13.9 |
| 24.34 | 3.65 | 9.4 |
| 26.06 | 3.42 | 12.5 |
| 27.68 | 3.22 | 13.5 |
| 28.56 | 3.12 | 10.8 |
| 30.37 | 2.94 | 9.9 |
| 32.05 | 2.79 | 11.1 |

IR (ATR method): 3034, 2951, 2926, 2853, 1622, 1526, 1498, 1450, 1406, 1341, 1310, 1261, 1218, 1141, 1117, 1087, 1063, 1051, 1034, 1013, 974, 914, 862, 841, 812, 785, 750, 696, 645 cm$^{-1}$;

Solvent: a mixed solvent of acetone and water, acetonitrile, n-hexane.

EXAMPLE 4(12)

Crystal comprising (2R)-2-propyloctanoic acid and (−)-cis-2-benzylaminocyclohexanemethanol NMR (CDCl$_3$): δ 7.37-7.29 (5H, m), 4.05-3.90 (3H, m), 3.70 (11, dd, J=3.2, 11.2 Hz), 3.05 (1H, m), 2.26 (1H, m), 2.14 (1H, m), 2.14 (1H, m), 1.87 (1H, m), 1.68-1.23 (21H, m), 0.91-0.85 (6H, m);

Melting point: 71.6-73.1° C.;

Powder X-ray Diffraction Spectral Data:

TABLE 37

| Crystal with (−)-cis-2-benzylaminocyclohexanemethanol | | |
|---|---|---|
| Diffraction angle (2θ) (degree) | Half width (Å) | Relative intensity (%) |
| 10.01 | 8.83 | 6.9 |
| 12.38 | 7.15 | 28.3 |
| 15.35 | 5.77 | 24.7 |
| 16.29 | 5.44 | 27.7 |
| 17.99 | 4.93 | 100.0 |
| 19.02 | 4.66 | 39.6 |
| 20.00 | 4.44 | 68.1 |
| 21.52 | 4.13 | 23.5 |
| 21.85 | 4.06 | 28.8 |
| 22.84 | 3.89 | 24.8 |
| 23.93 | 3.71 | 15.3 |
| 24.87 | 3.58 | 21.4 |
| 25.46 | 3.50 | 27.2 |
| 28.03 | 3.18 | 21.2 |
| 29.91 | 2.99 | 17.5 |
| 31.21 | 2.86 | 16.7 |
| 35.00 | 2.56 | 11.3 |
| 35.89 | 2.50 | 13.1 |

IR (ATR method): 3033, 2949, 2925, 2854, 1622, 1524, 1497, 1454, 1397, 1341, 1324, 1261, 1219, 1115, 1087, 1075, 1061, 1037, 1010, 975, 914, 781, 750, 697, 634 cm$^{-1}$; Solvent: a mixed solvent of methanol and water, a mixed solvent of ethanol and water, a mixed solvent of isopropyl alcohol and water, acetone, acetonitrile, a mixed solvent of dimethoxyethane and water, ethyl acetate, diethyl carbonate, methyl t-butyl ether, n-hexane.

EXAMPLE 4(13)

Crystal comprising (2R)-2-propyloctanoic acid and (S)-(−)-2-amino-3-phenyl-1-propanol NMR (CDCl$_3$): δ 7.33-7.13 (5H, m), 3.72 (1H, dd, J=4.0, 11.6 Hz), 3.49 (11, dd, J=7.2, 11.6 Hz), 3.22 (1H, m), 2.84 (1H, dd, J=5.6, 13.6 Hz), 2.65 (1H, dd, J=8.8, 13.6 Hz), 2.28 (1H, m), 1.62-1.18 (14H, m), 0.90 (3H, t, J=7.6 Hz), 0.86 (311, t, J=7.6 Hz);

Melting point: 67.4-69.7° C.;

IR (ATR method): 3241, 3029, 2953, 2925, 2853, 2546, 2163, 1623, 1576, 1541, 1497, 1456, 1398, 1374, 1338, 1285, 1206, 1175, 1113, 1093, 1065, 1031, 997, 944, 915, 850, 806, 740, 697 cm$^{-1}$;

Solvent: acetonitrile, ethyl acetate, diethyl carbonate, n-hexane.

EXAMPLE 4(14)

Crystal comprising (2R)-2-propyloctanoic acid and (R)-(+)-2-amino-3-phenyl-1-propanol NMR (CDCl$_3$): δ 7.33-7.14 (5H, m), 3.72 (1H, dd, J=3.6, 11.6 Hz), 3.50 (1H, dd, J=6.8, 11.6 Hz), 3.23 (1H, m), 2.84 (1H, dd, J=6.0, 13.6 Hz), 2.67 (1H, dd, J=8.4, 13.6 Hz), 2.26 (1H, m), 1.61-1.17 (14H, m), 0.89 (3H, t, J=7.2 Hz), 0.86 (3H, t, J=7.2 Hz);

Melting point: 62.6-66.1° C.;

Powder X-ray Diffraction Spectral Data:

TABLE 38

| Crystal with (R)-(+)-2-amino-3-phenyl-1-propanol | | |
|---|---|---|
| Diffraction angle (2θ) (degree) | Half width (Å) | Relative intensity (%) |
| 8.29 | 10.66 | 5.1 |
| 10.15 | 8.71 | 5.2 |
| 13.33 | 6.64 | 12.0 |
| 15.94 | 5.56 | 31.2 |
| 16.61 | 5.33 | 24.8 |
| 17.87 | 4.96 | 23.1 |
| 19.83 | 4.47 | 100.0 |
| 21.48 | 4.13 | 41.0 |
| 24.51 | 3.63 | 14.7 |
| 26.22 | 3.40 | 27.5 |
| 27.48 | 3.24 | 17.4 |
| 30.09 | 2.97 | 19.8 |
| 32.33 | 2.77 | 11.6 |
| 33.73 | 2.66 | 10.6 |
| 36.36 | 2.47 | 10.8 |

IR (ATR method): 3255, 3065, 3030, 2954, 2925, 2854, 2547, 2153, 1622, 1574, 1541, 1496, 1456, 1395, 1375, 1338, 1309, 1279, 1207, 1175, 1113, 1093, 1065, 1031, 997, 945, 913, 850, 787, 740, 697 cm$^{-1}$;

Solvent: acetonitrile, diethyl carbonate.

EXAMPLE 4(15)

Crystal Comprising (2R)-2-propyloctanoic acid and (R)-(+)-1-(4-bromophenyl)ethylamine NMR (CDCl$_3$): δ 7.45 (211, d, J=8.0 Hz), 7.23 (2H, d, J=8.0 Hz), 4.14 (1H, m), 2.30 (1H, m), 1.61-1.21 (17H, m), 0.92-0.86 (6H, m);

Melting point: 71.4-72.0° C.

Powder X-ray Diffraction Spectral Data:

TABLE 39

| Crystal with (R)-(+)-1-(4-bromophenyl)ethylamine | | |
|---|---|---|
| Diffraction angle (2θ) (degree) | Half width (Å) | Relative intensity (%) |
| 9.47 | 9.33 | 16.2 |
| 11.43 | 7.74 | 23.8 |
| 12.02 | 7.36 | 27.5 |
| 15.06 | 5.88 | 33.5 |
| 16.10 | 5.50 | 23.1 |
| 17.45 | 5.08 | 21.5 |
| 19.00 | 4.67 | 100.0 |
| 20.17 | 4.40 | 47.4 |
| 20.69 | 4.29 | 34.0 |

TABLE 39-continued

| Crystal with (R)-(+)-1-(4-bromophenyl)ethylamine | | |
|---|---|---|
| Diffraction angle (2θ) (degree) | Half width (Å) | Relative intensity (%) |
| 22.01 | 4.04 | 51.5 |
| 23.12 | 3.84 | 82.2 |
| 24.11 | 3.69 | 68.3 |
| 25.55 | 3.48 | 46.5 |
| 27.43 | 3.25 | 62.7 |
| 29.75 | 3.00 | 44.1 |
| 32.38 | 2.76 | 35.8 |
| 34.67 | 2.59 | 32.7 |
| 35.94 | 2.50 | 31.5 |

IR (ATR method): 2954, 2925, 2855, 2703, 2195, 1621, 1571, 1515, 1491, 1466, 1440, 1404, 1381, 1306, 1281, 1231, 1186, 1110, 1090, 1011, 898, 850, 832, 819, 779, 742, 725, 716, 686 cm$^{-1}$;

Solvent: diethyl carbonate, acetonitrile.

EXAMPLE 4(16)

Crystal comprising (2R)-2-propyloctanoic acid and (R)-(+)-1-phenylpropylamine

NMR (CDCl$_3$): δ 7.35-7.23 (5H, m), 3.85 (1H, t, J=6.8 Hz), 2.23 (1H, m), 1.84-1.69 (2H, m), 1.60-1.20 (14H, m), 0.91-0.83 (9H, m);

Melting point: 85.5-86.9° C.;

Powder X-ray Diffraction Spectral Data:

TABLE 40

| Crystal with (R)-(+)-1-phenylpropylamine | | |
|---|---|---|
| Diffraction angle (2θ) (degree) | Half width (Å) | Relative intensity (%) |
| 12.49 | 7.08 | 28.2 |
| 13.98 | 6.33 | 17.6 |
| 14.44 | 6.13 | 42.9 |
| 15.63 | 5.66 | 15.1 |
| 16.38 | 5.41 | 15.1 |
| 18.50 | 4.79 | 24.7 |
| 19.18 | 4.62 | 51.2 |
| 20.53 | 4.32 | 20.6 |
| 21.17 | 4.19 | 72.8 |
| 21.76 | 4.08 | 100.0 |
| 22.61 | 3.93 | 39.7 |
| 23.35 | 3.81 | 36.6 |
| 24.23 | 3.67 | 52.0 |
| 25.36 | 3.51 | 52.3 |
| 26.46 | 3.37 | 16.1 |
| 28.22 | 3.16 | 13.3 |
| 28.81 | 3.10 | 18.7 |
| 29.75 | 3.00 | 17.2 |
| 30.62 | 2.92 | 15.6 |
| 31.41 | 2.85 | 12.3 |
| 32.45 | 2.76 | 13.2 |
| 33.49 | 2.67 | 11.5 |
| 35.16 | 2.55 | 14.7 |
| 35.72 | 2.51 | 15.0 |

IR (ATR method): 2950, 2926, 2855, 2665, 2215, 1622, 1561, 1525, 1457, 1436, 1400, 1380, 1329, 1297, 1274, 1214, 1185, 1153, 1110, 1032, 998, 913, 892, 849, 778, 760, 750, 741, 695, 673 cm$^{-1}$;

Solvent: diethyl carbonate.

EXAMPLE 4(17)

Crystal comprising (2R)-2-propyloctanoic acid and 1,2-diphenylethylamine

NMR (CDCl$_3$): δ 7.35-7.14 (10H, m), 4.22 (1H, dd, J=5.2, 8.4 Hz), 3.03 (1H, dd, J=5.2, 13.2 Hz), 2.91 (1H, dd, J=8.4, 13.2 Hz), 2.33 (1H, m), 1.60 (2H, m), 1.47-1.23 (12H, m), 0.91 (3H, t, J=7.2 Hz), 087 (3H, t, J=6.8 Hz);

Melting point: 68.2-70.0° C.;

Powder X-ray Diffraction Spectral Data:

TABLE 41

| Crystal with 1,2-diphenylethylamine | | |
|---|---|---|
| Diffraction angle (2θ) (degree) | Half width (Å) | Relative intensity (%) |
| 12.38 | 7.14 | 12.3 |
| 13.37 | 6.62 | 25.1 |
| 14.04 | 6.30 | 18.2 |
| 16.50 | 5.37 | 56.3 |
| 17.73 | 5.00 | 100.0 |
| 18.80 | 4.72 | 77.8 |
| 19.83 | 4.47 | 77.3 |
| 21.17 | 4.19 | 34.2 |
| 22.80 | 3.90 | 44.5 |
| 24.07 | 3.69 | 41.2 |
| 25.14 | 3.54 | 40.0 |
| 27.06 | 3.29 | 29.8 |
| 28.35 | 3.15 | 20.0 |
| 29.25 | 3.05 | 18.5 |
| 30.66 | 2.91 | 18.6 |

IR (ATR method): 3030, 2953, 2925, 2852, 2663, 2176, 1627, 1536, 1497, 1467, 1455, 1431, 1396, 1338, 1310, 1275, 1232, 1110, 1074, 1024, 976, 935, 910, 846, 795, 775, 758, 740, 697 cm$^{-1}$;

Solvent: acetonitrile.

EXAMPLE 4(18)

Crystal comprising (2R)-2-propyloctanoic acid and benzhydrylamine

NMR (CDCl$_3$): δ 7.37-7.21 (10H m), 5.24 (1H, s), 2.35 (1H, m), 1.60 (2K, m), 1.65-1.22 (14H, m), 0.91 (3H, t, J=7.2 Hz), 0.88 (31, t, J=6.8 Hz);

Melting point: 70.5-71.1° C.;

Powder X-ray Diffraction Spectral Data:

TABLE 42

| Crystal with benzhydrylamine | | |
|---|---|---|
| Diffraction angle (2θ) (degree) | Half width (Å) | Relative intensity (%) |
| 13.58 | 6.52 | 8.6 |
| 14.50 | 6.11 | 13.5 |
| 16.05 | 5.52 | 15.4 |
| 16.85 | 5.26 | 43.4 |
| 18.38 | 4.82 | 42.9 |
| 19.27 | 4.60 | 60.7 |
| 21.28 | 4.17 | 100.0 |
| 21.63 | 4.10 | 76.2 |
| 22.70 | 3.91 | 42.5 |
| 23.46 | 3.79 | 52.0 |
| 24.59 | 3.62 | 21.2 |
| 25.85 | 3.44 | 35.0 |
| 26.48 | 3.36 | 40.7 |

TABLE 42-continued

Crystal with benzhydrylamine

| Diffraction angle (2θ) (degree) | Half width (Å) | Relative intensity (%) |
|---|---|---|
| 26.93 | 3.31 | 27.8 |
| 28.31 | 3.15 | 19.5 |
| 30.03 | 2.97 | 15.9 |
| 31.38 | 2.85 | 17.5 |
| 33.55 | 2.67 | 15.8 |
| 36.60 | 2.45 | 15.3 |

IR (ATR method): 2995, 2925, 2853, 2614, 2194, 1617, 1573, 1519, 1497, 1457, 1446, 1395, 1303, 1226, 1198, 1151, 1075, 1032, 1010, 998, 917, 837, 809, 755, 735, 695, 641, 542 cm$^{-1}$;
Solvent: acetonitrile.

EXAMPLE 4(19)

Crystal comprising (2R)-2-propyloctanoic acid and cyclohexylamine

NMR (CDCl$_3$): δ 2.80 (1H, m), 2.16 (1H, m), 1.98 (2H, m), 1.77 (2×m), 1.63 (1H, m), 1.53 (2H, m), 1.41-1.12 (17H, m), 0.91-0.85 (6H, m);
Melting point: 99.1-101.1° C.;

Powder X-ray Diffraction Spectral Data:

TABLE 43

Crystal with cyclohexylamine

| Diffraction angle (2θ) (degree) | Half width (Å) | Relative intensity (%) |
|---|---|---|
| 10.98 | 8.05 | 8.9 |
| 11.37 | 7.77 | 11.6 |
| 12.84 | 6.89 | 18.0 |
| 14.68 | 6.03 | 15.2 |
| 15.86 | 5.58 | 33.3 |
| 17.03 | 5.20 | 39.0 |
| 17.62 | 5.03 | 42.1 |
| 18.82 | 4.71 | 100.0 |
| 20.09 | 4.42 | 54.8 |
| 20.90 | 4.25 | 71.7 |
| 21.83 | 4.07 | 75.9 |
| 22.54 | 3.94 | 35.6 |
| 25.40 | 3.50 | 25.2 |
| 25.98 | 3.43 | 26.5 |
| 27.91 | 3.19 | 19.8 |
| 29.07 | 3.07 | 21.4 |
| 30.03 | 2.97 | 21.5 |
| 31.64 | 2.83 | 18.8 |
| 33.24 | 2.69 | 16.0 |
| 35.89 | 2.50 | 17.5 |

IR (ATR method): 2922, 2855, 2625, 2569, 2224, 1634, 1525, 1455, 1399, 1340, 1313, 1285, 1246, 1140, 1115, 1073, 1050, 920, 891, 849, 801, 780, 748, 641, 554 cm$^{-1}$;
Solvent: acetonitrile.

EXAMPLE 4(20)

Crystal comprising (2R)-2-propyloctanoic acid and dicyclohexylamine

NMR (CDCl$_3$): δ 2.80 (2K m), 2.19 (1H, m), 1.97 (4H, m), 1.76 (4H, m), 1.59 (4H, m), 1.43-1.13 (221, m), 0.90 (31, t, J=7.2 Hz), 0.87 (31, t, J=6.8 Hz);
Melting point: 79.9-82.2° C.;

Powder X-ray Diffraction Spectral Data:

TABLE 44

Crystal with dicyclohexylamine

| Diffraction angle (2θ) (degree) | Half width (Å) | Relative intensity (%) |
|---|---|---|
| 11.16 | 7.92 | 12.3 |
| 12.22 | 7.24 | 5.9 |
| 14.59 | 6.07 | 8.6 |
| 15.30 | 5.78 | 14.6 |
| 16.75 | 5.29 | 19.1 |
| 18.28 | 4.85 | 35.2 |
| 19.13 | 4.64 | 100.0 |
| 19.80 | 4.48 | 38.1 |
| 21.27 | 4.17 | 25.0 |
| 22.42 | 3.96 | 26.1 |
| 23.51 | 3.78 | 25.9 |
| 25.20 | 3.53 | 20.3 |
| 30.38 | 2.94 | 12.4 |
| 31.17 | 2.87 | 15.4 |
| 33.03 | 2.71 | 12.9 |

IR (ATR method): 2926, 2853, 1622, 1524, 1488, 1455, 1401, 1352, 1306, 1253, 1186, 1113, 1084, 1064, 1037, 980, 921, 887, 849, 805, 758, 640, 596 cm$^{-1}$;
Solvent: acetonitrile.

EXAMPLE 4(21)

Crystal comprising (2R)-2-propyloctanoic acid and cycloheptylamine

NMR (CDCl$_3$): δ 6.60-5.40 (br, 3H), 3.06-2.96 (m, 1H), 2.22-2.12 (m, 1H), 2.03-1.94 (m, 2H), 1.74-1.20 (m, 24H), 0.89 (t, J=7.2 Hz, 3H), 0.88 (t, J=8.8 Hz, 3H);
Melting point: 81.8-85.7° C.;

Powder X-ray Diffraction Spectral Data:

TABLE 45

Crystal with cycloheptylamine

| Diffraction angle (2θ) (degree) | Half width (Å) | Relative intensity (%) |
|---|---|---|
| 7.98 | 11.07 | 26.6 |
| 12.29 | 7.20 | 20.7 |
| 14.68 | 6.03 | 22.2 |
| 16.19 | 5.47 | 16.3 |
| 17.39 | 5.10 | 29.1 |
| 18.34 | 4.83 | 71.6 |
| 19.07 | 4.65 | 86.4 |
| 20.01 | 4.43 | 100.0 |
| 20.98 | 4.23 | 28.7 |
| 22.05 | 4.03 | 22.8 |
| 24.19 | 3.68 | 21.5 |
| 25.56 | 3.48 | 21.7 |
| 27.02 | 3.30 | 22.0 |
| 30.80 | 2.90 | 21.4 |
| 32.65 | 2.74 | 23.1 |

IR (ATR method): 2924, 1624, 1523, 1457, 1396 cm$^{-1}$;
Solvent: acetonitrile, absence of solvent.

EXAMPLE 4(22)

Crystal comprising (2R)-2-propyloctanoic acid and N-ethylcyclohexylamine

NMR (CDCl$_3$): δ 8.05-7.70 (br, 2H), 2.86 (q, J=7.2 Hz, 2H), 2.77-2.67 (m, 1H), 2.22-2.13 (m, 1H), 2.06-1.98 (m,

2H), 1.82-1.74 (m, 2H), 1.67-1.48 (m, 3H), 1.45-1.05 (m, 20H), 0.89 (t, J=7.2 Hz, 3H), 0.87 (t, J=7.2 Hz, 3H);

Melting point: 64.6-67.6° C.;

Powder X-ray Diffraction Spectral Data:

TABLE 46

Crystal with N-ethylcyclohexylamine

| Diffraction angle (2θ) (degree) | Half width (Å) | Relative intensity (%) |
| --- | --- | --- |
| 7.70 | 11.47 | 100.0 |
| 9.27 | 9.53 | 8.9 |
| 12.09 | 7.31 | 8.4 |
| 14.09 | 6.28 | 7.7 |
| 14.60 | 6.06 | 10.7 |
| 15.21 | 5.82 | 7.2 |
| 16.62 | 5.33 | 5.2 |
| 17.85 | 4.96 | 15.0 |
| 18.19 | 4.87 | 8.5 |
| 19.82 | 4.48 | 23.2 |
| 20.78 | 4.27 | 16.6 |
| 21.74 | 4.09 | 10.6 |
| 22.61 | 3.93 | 9.4 |
| 23.42 | 3.80 | 8.8 |
| 25.09 | 3.55 | 8.2 |

IR (ATR method): 2925, 1622, 1531, 1449, 1402 cm$^{-1}$;
Solvent: acetonitrile, absence of solvent.

EXAMPLE 4(23)

Crystal comprising (2R)-2-propyloctanoic acid and 2,2,6,6-tetramethyl-4-piperidinol NMR (CDCl$_3$): δ 5.00-4.60 (br, 3H), 4.15-4.02 (m, 1H), 2.29-2.21 (m, 1H), 1.94 (dd, J=12.8, 4.0 Hz, 2H), 1.65-1.50 (m, 2H), 1.45-1.15 (m, 26H), 0.89 (t, J=7.2 Hz, 3H), 0.87 (t, J=7.0 Hz, 3H);

Melting point: 113.2-117.0° C.;

Powder X-ray Diffraction Spectral Data:

TABLE 47

Crystal with 2,2,6,6-tetramethyl-4-piperidinol

| Diffraction angle (2θ) (degree) | Half width (Å) | Relative intensity (%) |
| --- | --- | --- |
| 9.11 | 9.70 | 100.0 |
| 13.47 | 6.57 | 16.3 |
| 14.84 | 5.96 | 9.2 |
| 17.25 | 5.14 | 25.8 |
| 18.18 | 4.88 | 17.9 |
| 19.93 | 4.45 | 21.8 |
| 21.24 | 4.18 | 19.7 |
| 22.30 | 3.98 | 14.6 |
| 23.80 | 3.74 | 11.8 |
| 24.78 | 3.59 | 11.0 |
| 25.96 | 3.43 | 11.5 |
| 30.28 | 2.95 | 8.5 |

IR (ATR method): 3272, 2927, 1605, 1522 cm$^{-1}$;
Solvent: acetonitrile.

EXAMPLE 4(24)

Crystal comprising (2R)-2-propyloctanoic acid and 2-(2-methoxyphenyl)ethylamine

NMR (CDCl$_3$): δ 7.21 (dt, J=7.6, 1.6 Hz, 1H), 7.14 (dd, J=7.4, 1.8 Hz, 1H), 6.91-6.83 (m, 2H), 5.25-4.95 (br, 3H), 3.81 (s, 3H), 3.00 (t, J=7.0 Hz, 2H), 2.84 (t, J=7.0 Hz, 2H), 2.30-2.20 (m, 1H), 1.65-1.50 (m, 2H), 1.45-1.20 (m, 12H), 0.89 (t, J=7.2 Hz, 3H), 0.86 (t, J=7.2 Hz, 3H);

Melting point: 59.0-60.4° C.;

Powder X-ray Diffraction Spectral Data:

TABLE 48

Crystal with 2-(2-methoxyphenyl)ethylamine

| Diffraction angle (2θ) (degree) | Half width (Å) | Relative intensity (%) |
| --- | --- | --- |
| 9.56 | 9.25 | 16.1 |
| 12.26 | 7.21 | 30.0 |
| 13.28 | 6.66 | 18.3 |
| 13.93 | 6.35 | 27.0 |
| 15.34 | 5.77 | 53.4 |
| 15.99 | 5.54 | 35.3 |
| 16.50 | 5.37 | 32.5 |
| 17.31 | 5.12 | 23.5 |
| 18.57 | 4.77 | 32.3 |
| 19.15 | 4.63 | 58.6 |
| 20.04 | 4.43 | 100.0 |
| 20.74 | 4.28 | 90.6 |
| 21.65 | 4.10 | 69.2 |
| 23.52 | 3.78 | 44.1 |
| 24.48 | 3.63 | 35.2 |
| 25.76 | 3.46 | 37.7 |
| 26.35 | 3.38 | 45.4 |
| 27.52 | 3.24 | 28.1 |
| 29.20 | 3.06 | 34.4 |
| 30.87 | 2.89 | 16.7 |
| 32.10 | 2.79 | 17.0 |
| 35.28 | 2.54 | 17.1 |

IR (ATR method): 2921, 1634, 1494, 1242 cm$^{-1}$;
Solvent: acetonitrile, absence of solvent.

EXAMPLE 4(25)

Crystal comprising (2R)-2-propyloctanoic acid and 2-(3,4-dimethoxyphenyl)ethylamine NMR (CDCl$_3$): δ 6.81 (d, J=8.0 Hz, 1H), 6.76-6.72 (m, 2H), 4.50-4.25 (br, 3H), 3.88 (s, 3H), 3.86 (s, 3H), 3.00 (t, J=7.0 Hz, 2H), 2.76 (t, J=7.0 Hz, 2H), 2.35-2.05 (m, 1H), 1.65-1.50 (m, 2H), 1.50-1.20 (m, 12H), 0.90 (t, J=7.2 Hz, 3H), 0.86 (t, J=7.2 Hz, 3H);

Melting point: 54.3-56.6° C.;

Powder X-ray Diffraction Spectral Data:

TABLE 49

Crystal with 2-(3,4-dimethoxyphenyl)ethylamine

| Diffraction angle (2θ) (degree) | Half width (Å) | Relative intensity (%) |
| --- | --- | --- |
| 8.56 | 10.32 | 15.3 |
| 10.44 | 8.47 | 17.8 |
| 11.98 | 7.38 | 7.7 |
| 14.64 | 6.05 | 15.0 |
| 15.34 | 5.77 | 23.6 |
| 16.88 | 5.25 | 28.3 |
| 18.73 | 4.73 | 11.9 |
| 19.17 | 4.63 | 10.3 |
| 20.57 | 4.31 | 96.5 |
| 22.05 | 4.03 | 21.6 |
| 22.95 | 3.87 | 100.0 |
| 25.22 | 3.53 | 19.2 |
| 27.65 | 3.22 | 9.5 |
| 29.07 | 3.07 | 8.0 |
| 32.33 | 2.77 | 7.8 |

IR (ATR method): 2920, 1515, 1449, 1402, 1237 cm$^{-1}$;
Solvent: acetonitrile, absence of solvent.

EXAMPLE 4(26)

Crystal comprising (2R)-2-propyloctanoic acid and N-isopropylbenzylamine

NMR (CDCl$_3$): δ 7.40-7.25 (m, 5H), 5.50-5.00 (br, 2H), 3.88 (s, 2H), 3.00-2.90 (m, 1H), 2.32-2.22 (m, 1H), 1.65-1.50 (m, 2H), 1.45-1.20 (m, 12H), 1.17 (d, J=6.4 Hz, 6M), 0.90 (t, J=7.4 Hz, 3H), 0.87 (t, J=7.0 Hz, 3H);
Melting point: 50.2-50.6° C.;
Powder X-ray Diffraction Spectral Data:

TABLE 50

Crystal with N-isopropylbenzylamine

| Diffraction angle (2θ) (degree) | Half width (Å) | Relative intensity (%) |
|---|---|---|
| 7.97 | 11.08 | 100.0 |
| 11.34 | 7.80 | 19.8 |
| 12.91 | 6.85 | 11.8 |
| 13.36 | 6.62 | 7.8 |
| 15.27 | 5.80 | 16.1 |
| 17.21 | 5.15 | 30.1 |
| 17.68 | 5.01 | 18.8 |
| 18.83 | 4.71 | 39.2 |
| 20.06 | 4.42 | 19.3 |
| 21.88 | 4.06 | 44.2 |
| 23.29 | 3.82 | 21.2 |
| 24.01 | 3.70 | 15.9 |
| 26.76 | 3.33 | 11.4 |
| 27.67 | 3.22 | 9.5 |
| 31.83 | 2.81 | 8.8 |
| 32.94 | 2.72 | 9.1 |

IR (ATR method): 2926, 1529, 1442, 1401 cm$^{-1}$;
Solvent: absence of solvent.

EXAMPLE 4(27)

Crystal comprising (2R)-2-propyloctanoic acid and N-butylbenzylamine

NMR (CDCl$_3$): δ 7.40-7.25 (m, 5H), 5.55-5.20 (br, 2H), 3.87 (s, 2H), 2.68 (t, J=7.4 Hz, 2H), 2.32-2.24 (m, 1H), 1.65-1.50 (m, 4H), 1.45-1.20 (m, 14H), 0.93-0.84 (m, 9H);
Melting point: 61.3-62.8° C.;
Powder X-ray Diffraction Spectral Data:

TABLE 51

Crystal with N-butylbenzylamine

| Diffraction angle (2θ) (degree) | Half width (Å) | Relative intensity (%) |
|---|---|---|
| 11.71 | 7.55 | 10.1 |
| 13.84 | 6.39 | 12.8 |
| 19.81 | 4.48 | 38.2 |
| 20.67 | 4.29 | 100.0 |
| 24.64 | 3.61 | 22.3 |

IR (ATR method): 2925, 1545, 1458, 1398 cm$^{-1}$;
Solvent: absence of solvent.

EXAMPLE 5

Study on the Effect of Improving the Optical Purity of (2R)-2-propyloctanoic acid Using dibenzylamine The frequency of recrystallization required for increasing the optical purity from 95.0% e.e. to 99.5% or more was examined using dibenzylamine. The optical purity of the crystal comprising (2R)-2-propyloctanoic acid and dibenzylamine was determined by liquid chromatography according to the method as described in Example 2 through a free (2R)-2-propyloctanoic acid and its phenacyl ester derivative.

<First Recrystallization>

(2R)-2-Propyloctanoic acid (5.0 g) of 95.0% e.e. in optical purity was dissolved in acetonitrile (75 mL) and dibenzylamine (2.9 g) under heating at about 70° C. (outer temperature) and stirred for about 15 minutes. The reaction mixture was allowed to stand for cooling for about 1 hour, then cooled at about 5° C. for about 40 minutes, and filtered. The resulting crystals were washed with acetonitrile (10 mL) and dried in vacuo at about 35° C. to give the crystal comprising (2R)-2-propyloctanoic acid and dibenzylamine (7.1 g, 98.2% e.e.; yield 93%).

<Second Recrystallization>

The crystal comprising (2R)-2-propyloctanoic acid and dibenzylamine (6.8 g) produced in the first recrystallization was dissolved in acetonitrile (102 mL) under heating at about 70° C. (outer temperature) and stirred for about 15 minutes. The reaction mixture was allowed to stand for cooling for about 1 hour, then cooled at about 8° C. for about 40 minutes, and filtered. The resulting crystals were washed with acetonitrile (10 mL) and dried in vacuo at about 35° C. to give the crystal comprising (2R)-2-propyloctanoic acid and dibenzylamine (4.8 g, 99.5% e.e.; yield 71%).

<Results>

By twice repeated crystallization, the optical purity of (2R)-2-propyloctanoic acid reached 99.5% e.e. Recovery of the twice repeated crystallization was 66%.

Comparative Example 1

Crystal Comprising (2R)-2-propyloctanoic acid and (R)-(+)-1-phenylethylamine

Using (R)-(+)-1-phenylethylamine in place of dibenzylamine, the same operation as in Example 1 was performed to give the title compound having the following physicochemical properties. The resulting compounds was crystals. In this Comparative Example, a variety of solvents were examined in the same manner as described above. The solvents used in obtaining the crystals are described in respective items. The optical purity of (2R)-2-propyloctanoic acid used as a starting material was 95.0% e.e.

NMR (CDCl$_3$): δ 7.35-7.25 (5H, m), 4.18 (1H, q, J=6.4 Hz), 2.28 (1H, m), 1.59-1.26 (14H, m), 1.44 (311, d, J=6.4 Hz), 0.91-0.85 (6H, m);
Melting point: 74.3-74.8° C.;

Powder X-ray Diffraction Spectral Data:

TABLE 52

Crystal with (R)-(+)-1-phenylethylamine

| Diffraction angle (2θ) (degree) | Half width (Å) | Relative intensity (%) |
|---|---|---|
| 8.46 | 10.44 | 8.5 |
| 9.29 | 9.51 | 14.0 |
| 10.94 | 8.08 | 54.2 |
| 11.36 | 7.78 | 38.1 |
| 12.70 | 6.96 | 38.8 |
| 15.00 | 5.90 | 74.8 |
| 15.91 | 5.57 | 22.0 |

TABLE 52-continued

Crystal with (R)-(+)-1-phenylethylamine

| Diffraction angle (2θ) (degree) | Half width (Å) | Relative intensity (%) |
|---|---|---|
| 16.70 | 5.30 | 32.7 |
| 17.27 | 5.13 | 29.0 |
| 18.46 | 4.80 | 22.4 |
| 19.22 | 4.62 | 50.6 |
| 19.92 | 4.45 | 35.7 |
| 21.32 | 4.16 | 59.3 |
| 21.94 | 4.05 | 100.0 |
| 23.08 | 3.85 | 32.8 |
| 24.15 | 3.68 | 21.7 |
| 25.71 | 3.46 | 28.4 |
| 27.99 | 3.19 | 30.5 |
| 31.30 | 2.86 | 19.0 |
| 32.39 | 2.76 | 17.1 |
| 36.00 | 2.49 | 16.3 |
| 36.96 | 2.43 | 17.2 |

IR (ATR method): 2954, 2927, 2847, 2694, 2637, 2543, 2216, 1624, 1570, 1525, 1496, 1456, 1438, 1397, 1381, 1315, 1293, 1275, 1227, 1185, 1155, 1112, 1089, 1024, 1003, 989, 911, 849, 764, 755, 695, 539 cm$^{-1}$;

Solvent: acetone, acetonitrile, ethyl acetate, diethyl carbonate, n-heptane, diethyleneglycol dimethyl ether, water.

Comparative Example 2

Study on the effect of improving the optical purity of (2R)-2-propyloctanoic acid using (R)-(+)-1-phenylethylamine The frequency of recrystallization required for increasing the optical purity from 95.0% e.e. to 99.5% e.e. or more was examined using (R)-(+)-1-phenylethylamine. The optical purity of the crystal comprising (2R)-2-propyloctanoic acid and (R)-(+)-1-phenylethylamine was determined by liquid chromatography according to the method as described in Example 2 through a free (2R)-2-propyloctanoic acid and its phenacyl ester derivative.

<First Recrystallization>

(2R)-2-Propyloctanoic, acid (5.0 g) of 95.0% e.e. in optical purity was dissolved in acetonitrile (75 mL) and (R)-(+)-1-phenylethylamine (3.6 g) under heating at about 70° C. (outer temperature) and stirred for about 15 minutes. The reaction mixture was allowed to stand for cooling for about 1 hour, then cooled at about 5° C. for about 40 minutes, and filtered. The resulting crystals were washed with acetonitrile (10 mL) and dried in vacuo at about 35° C. to give the crystal comprising (2R)-2-propyloctanoic acid and (R)-(+)-1-phenylethylamine (7.9 g, 97.7% e.e.; yield 96%).

<Second Recrystallization>

The crystal comprising (2R)-2-propyloctanoic acid and (R)-(+)-1-phenylethylamine (7.8 g) produced in the first recrystallization was dissolved in acetonitrile (117 mL) under heating at about 70° C. (outer temperature) and stirred for about 20 minutes. The reaction mixture was allowed to stand for cooling for about 1 hour, then cooled at about 5° C. for about 40 minutes, and filtered. The resulting crystals were washed with acetonitrile (10 mL) and dried in vacuo at about 35° C. to give the crystal comprising (2R)-2-propyloctanoic acid and (R)-(+)-1-phenylethylamine (6.9 g, 98.8% e.e.; yield 87%).

<Third Recrystallization>

Using the crystal comprising (2R)-2-propyloctanoic acid and R)-(+)-1-phenylethylamine (6.8 g) produced in the second recrystallization and acetonitrile (102 mL), the same operation as in the second recrystallization was made to give the crystal comprising (2R)-2-propyloctanoic acid and (R)-(+)-1-phenylethylamine (6.0 g, 98.9% e.e.; yield 88%).

<Fourth Recrystallization>

Using the crystal comprising (2R)-2-propyloctanoic acid and (R)-(+)-1-phenylethylamine (5.9 g) produced in the third recrystallization and acetonitrile (89 mL), the same operation as in the second recrystallization was made to give the crystal comprising (2R)-2-propyloctanoic acid and (R)-(+)-1-phenylethylamine (5.2 g, 99.1% e.e.; yield 88%).

<Fifth Recrystallization>

Using the crystal comprising (2R)-2-propyloctanoic acid and (R)-(+)-1-phenylethylamine (5.1 g) produced in the fourth recrystallization and acetonitrile (77 mL), the same operation as in the second recrystallization was made to give the crystal comprising (2R)-2-propyloctanoic acid and (R)-(+)-1-phenylethylamine (4.4 g, 99.3% e.e.; yield 87%).

<Sixth Recrystallization>

Using the crystal comprising (2R)-2-propyloctanoic acid and (R)-(+)-1-phenylethylamine (4.3 g) produced in the fifth recrystallization and acetonitrile (65 mL), the same operation as in the second recrystallization was made to give the crystal comprising (2R)-2-propyloctanoic acid and (R)-(+)-1-phenylethylamine (3.7 g, 99.4% e.e.; yield 86%).

<Seventh Recrystallization>

Using the crystal comprising (2R)-2-propyloctanoic acid and (R)-(+)-1-phenylethylamine (3.6 g) produced in the sixth recrystallization-and-acetonitrile (54 mL), the same operation as in the second recrystallization was made to give the crystal comprising (2R)-2-propyloctanoic acid and (R)-(+)-1-phenylethylamine (3.0 g, 99.6% e.e.; yield 83%).

<Results>

(2R)-2-propyloctanoic acid having the optical purity of 99.5% e.e. or more was obtained by 7 repeated crystallizations. Recovery of 7 repeated crystallizations was 40%.

Comparative Example 3

Study on Crystallization using (2R)-2-propyloctanoic acid and a Variety of Amines (Study-1)

(2R)-2-Propyloctanoic acid (1 g, 5.4 mmole) produced in Reference Example 4 was mixed with the following respective amines (5.4 mmole), and the mixture was heated for dissolving, then allowed to stand at room temperature for about 24 hours, and further at about 5° C. for about 24 hours. Thus, it was confirmed whether solids were precipitated or not.

<Amines examined: 46 species>

Cyclopropylamine [CAS: #765-30-0], 2-methoxyethylamine [CAS: #109-85-3], trimethylamine [CAS: #75-50-3], 2-dimethylaminoethanol [CAS: #108-01-0], 2-amino-2-methyl-1-propanol [CAS: #124-68-5], N,N-dimethylethylamine [CAS: #598-56-1], 3-methoxypropylamine [CAS: #5332-73-0], 2-ethoxyethylamine [CAS: #110-76-9], 1-methylpyrrolidine [CAS: #120-94-5], N-amylamine [CAS: #110-58-7], N-methylbutylamine [CAS: #110-68-9], N,N-dimethylisopropylamine [CAS: #996-35-0], 3-dimethylamino-1-propanol [CAS: #3179-63-

3], cyclopentylamine [CAS: #1003-03-8], isoamylamine [CAS: #107-85-7], 3-ethoxypropylamine [CAS: #6291-85-6], 2-diethylaminoethanol [CAS: #100-37-8], 1-(2-hydroxyethyl)pyrrolidine [CAS: #2955-88-6], 4-methylpiperidine [CAS: #626-58-4], N-(2-hydroxyethyl)morpholine [CAS: #622-40-2], 1-methylpiperidine [CAS: #626-67-5], hexamethyleneimine [CAS: #111-49-9], N-ethyl-N-butylamine [CAS: #13360-63-9], 2-(butylamino)ethanol [CAS: #111-75-1], bis(2-methoxyethyl)amine [CAS: #111-95-5], aminomethylcyclohexane [CAS: #3218-02-8], N-methylcyclohexylamine [CAS: #100-60-7], 1-ethylpiperidine [CAS: #766-09-6], N-piperidineethanol [CAS: #3040-44-6], 2-methoxybenzylamine [CAS: #6850-57-3], 2-phenylethylamine [CAS: #3600-86-0], N-methylbenzylamine [CAS: #103-67-3], 1-butylpyrrolidine [CAS: #767-10-2], N,N-dimethylcyclohexylamine [CAS: #98-94-2], piperonylamine [CAS: #2620-50-0], 4-methoxybenzylamine [CAS: #2393-23-9], N,N-diisopropylethylamine [CAS: #7087-68-5], N-benzylethanolamine [CAS: #104-63-2], 2,2,6,6-tetramethylpiperidine [CAS: #768-66-1], 1,2,3,4-tetrahydroisoquinoline [CAS: #91-21-4], 2-(4-methxoyphenyl)ethylamine [CAS: #55-81-2], tripropylamine [CAS: #102-69-2], N,N-diethylcyclohexylamine [CAS: #91-65-6], 2-(dibutylamino)ethanol [CAS: #102-81-8], 4-benzylpiperidine [CAS: #31252-42-3], and tributylamine [CAS: #102-82-9].

<Results>

Among the above 46 species of amines, when cyclopentylamine, aminomethylcyclohexane, 2-methoxybenzylamine, 4-methoxybenzylamine, and 2-(4-methoxyphenyl)ethylamine were used, solids were precipitated, but the remaining other amines precipitated no solid.

The resulting 5 species of solids were analyzed by a powdered X-ray diffraction analysis (under the condition as described in Example 1), indicating that the precipitates were not crystal.

Comparative Example 4

Study on Crystallization using (2R)-2-propyloctanoic acid and a Variety of Amines (Study-2)

(2R)-2-Propyloctanoic acid (1 g, 5.4 mmole) produced in Reference Example 4 was mixed with acetonitrile (10 mL) and the following 8 species of amines (5.4 mmole), and the mixture was heated for dissolving, then allowed to stand at room temperature for about 24 hours, and further at about 5° C. for about 24 hours. Thus, it was confirmed whether solids were precipitated or not. When no dissolving occurred under heating, after addition of water (1 mL), the same operation was made, or using methanol or ethanol in place of acetonitirle, the same operation was made.

<Amines examined; 8 species>

2-Amino-2-methyl-1,3-propanediol [CAS: #115-69-5], 4-hydroxypiperidine [CAS: #5382-16-1], 4-hydroxy-1-methylpiperidine [CAS: #106-52-5], 1-benzyl-4-hydroxypiperidine [CAS: #4727-72-4], Tris [CAS: #77-86-1], L-arginine [CAS: #74-79-3], L-lysine [CAS: #56-87-1], and L-histidine [CAS: #71-00-1].

<Results>

No solid was precipitated in all of the above 8 amines.

Comparative Example 5

Study on Crystallization Using (2R)-2-propyloctanoic acid and an Alkali Metal or Alkaline Earth Metal According to the following table, (2R)-2-propyloctanoic acid produced in Reference Example 4 was mixed with an alkali metal hydroxide or an alkaline earth metal hydroxide under stirring, then concentrated, and then lyophilized; thus, it was confirmed whether solids were precipitated or not.

TABLE 53

| (2R)-2-Propyloctanoic acid | Base |
|---|---|
| 1.86 g, 10 mmol | aqueous 1 mol/L sodium hydroxide (NaOH) solution (10 mL, 10 mmol) |
| 1.86 g, 10 mmol | aqueous 1 mol/L potassium hydroxide (KOH) solution (10 mL, 10 mmol) |
| 0.186 g, 1 mmol | Calcium hydroxide (Ca(OH)$_2$) (37 mg)/water (30 mL) |
| 0.186 g, 1 mmol | Barium hydroxide octahydrate (Ba(OH)$_2$•8H$_2$O) (157 mg)/water (10 mL) |
| 1.86 g, 10 mmol | Cesium hydroxide (CsOH) (1.49 g)/water(5 mL) |

<Results>

When sodium hydroxide, potassium hydroxide, barium hydroxide octahydrate, and cesium hydroxide were used, the resulting salts (sodium salt, potassium salt, barium salt, cesium salt) were oil and precipitated no solid.

When calcium hydroxide was used, a solid (calcium salt) was precipitated; the precipitate was analyzed by a powdered X-ray diffraction analysis (under the condition as described in Example 1), indicating that it was not crystal but amorphous.

Formulation Example 1

The following ingredients were mixed in a conventional manner and then made tablets; thus, 1,000,000 tablets containing 10 mg/tablet of an active ingredient were prepared.

Crystals comprising (2R)-2-propyloctanoic acid and dibenzylamine (10 kg); carboxymethylcellulose calcium (disintegrator) (2 kg); magnesium stearate (lubricant) (1 kg); and microcrystalline cellulose (87 kg).

Formulation Example 2

The following ingredients were mixed in a conventional manner, then filtered through a dust-removal filter, sterilized under heating in an autoclave, and then 5 mL each distributed into 1,000,000 ampoules containing 20 mg/ampoule of active ingredient.

Crystals comprising (2R)-2-propyloctanoic acid and dibenzylamine (20 kg); mannitol (200 kg); and distilled water (5 kL).

INDUSTRIAL APPLICABILITY

The crystals comprising (2R)-2-propyloctanoic acid and amines obtained in the present invention are excellent materials of which the pharmacological activity of (2R)-2-propyloctanoic acid is maintained and by which a problem in pharmaceutical formulation that the material is oil can be overcome. Thus, the crystals can be used, for example, as pharmaceuticals in orally administrable solid preparations such as tablets. In addition, the crystals comprising (2R)-2-propyloctanoic acid and dibenzylamine are useful as intermediates convertible into (2R)-2-propyloctanoic acid having the optical purity over 99.5% e.e., which so far cannot be obtained and is very useful as pharmaceutical.

The invention claimed is:

1. An isolated crystal consisting essentially of (2R)-2-propyloctanoic acid and an amine,
    wherein the amine is (+)-dehydroabietylamine, (R)-(−)-2-phenylglycinol, (S)-(+)-2-phenylglycinol, (−)-cis-myrtanylamine, (R)-(+)-1-(p-tolyl)ethylamine, (R)-(+)-1-(1-naphthyl) ethylaamine, (S)-(−)-1-(1-naphthyl) ethylamine, L-tyrosinamide, (1S,2R)-(+)-2-amino-1,2-diphenylethanol, (1R,2S)-(−)-2-amino-1,2-diphenylethanol, (+)-cis-2-benzylaminocyclohexanemethanol, (−)-cis-2-benzylaminocyclohexanemethanol, (S)-(−)-2-amino-3-phenyl-1-propanol, (R)-(+)-2-amino-3-phenyl-1-propanol, (R)-(+)-1-(4-bromophenyl) ethylamine, (R)-(+)-1-phenylpropylamine, dibenzylamine, 1,2-diphenylethylaamine, benzhydrylamine, cyclohexylamine, dicyclohexylamine, cycloheptylamine, N-ethylcyclohexylamine, 2,2,6,6-tetramethyl-4-piperidinol, 2-(2-methoxyphenyl)ethylamine, 2-(3,4-dimethoxyphenyl)ethylamine, N-isopropylbenzylamine, or N-butylbenzylamine.

2. A pharmaceutical composition, comprising the crystal according to claim 1 as an active ingredient, and a pharmaceutically acceptable carrier or diluent.

3. A pharmaceutical composition, comprising the crystal according to claim 1 in combination with at least one selected from an anticonvulsant, an acetylcholinesterase inhibitor, a neurotrophic factor, an aldose reductase inhibitor, an antithrombotic, an oral anticoagulant, a synthetic antithrombin drug, an antiplatelet drug, a thrombolytic agent, a Factor Xa inhibitor, a Factor VIIa inhibitor, a cerebral blood flow and metabolism improver, an antioxidant, a glycerin preparation, a β-secretase inhibitor, a β-amyloid protein aggregation inhibitor, a cerebral function activator, a dopamine receptor agonist, a monoamine oxidase inhibitor, an anticholinergic drug, a COMT inhibitor, a therapeutic agent for amyotrophic lateral sclerosis, a therapeutic agent for hyperlipidemia, an apoptosis inhibitor, a nerve differentiation and regeneration promoter, a non-steroidal anti-inflammatory drug, a steroid drug, and a sexual hormone or its derivative.

4. An isolated crystal consisting essentially of 2-propyloctanoic acid and dibenzylamine.

5. The isolated crystal according to claim 4, wherein the 2-propyloctanoic acid is (2R)-2-propyloctanoic acid.

6. The isolated crystal according to claim 5, which has an optical purity of 97% e.e. or more.

7. The isolated crystal according to claim 5, which has a specific rotation of −3.6°.

* * * * *